(12) United States Patent
Gray

(10) Patent No.: US 7,077,826 B1
(45) Date of Patent: Jul. 18, 2006

(54) SYRINGE AND METHOD OF USING

(76) Inventor: Robin Scott Gray, 3538 Split Rail La., Ellicott City, MD (US) 21042

( * ) Notice: Subject to any disclaimer, the term of this patent is extended or adjusted under 35 U.S.C. 154(b) by 441 days.

(21) Appl. No.: 10/349,707

(22) Filed: Jan. 23, 2003

Related U.S. Application Data

(63) Continuation-in-part of application No. 10/057,519, filed on Jan. 24, 2002, now Pat. No. 6,880,564.

(51) Int. Cl.
A61M 5/00 (2006.01)
A61M 5/178 (2006.01)

(52) U.S. Cl. ............................. 604/171; 604/212
(58) Field of Classification Search .............. 604/212, 604/216, 187, 162, 214, 191, 204, 263, 200, 604/110, 171
See application file for complete search history.

(56) References Cited

U.S. PATENT DOCUMENTS

| | | | |
|---|---|---|---|
| 2,950,717 A * | 5/1960 | Bonet | 604/214 |
| 3,134,380 A | 5/1964 | Armao | |
| 3,965,897 A * | 6/1976 | Lundquist | 604/246 |
| 4,068,662 A | 1/1978 | Sneider | |
| 4,753,638 A | 6/1988 | Peters | |
| 4,804,371 A | 2/1989 | Vaillancourt | |
| 4,911,694 A | 3/1990 | Dolan | |
| 4,915,697 A | 4/1990 | DuPont | |
| 4,927,416 A | 5/1990 | Tomkiel | |
| 4,932,947 A | 6/1990 | Cardwell | |
| 5,017,187 A | 5/1991 | Sullivan | |
| 5,219,338 A | 6/1993 | Haworth | |
| 5,419,766 A | 5/1995 | Chang et al. | |
| 5,419,773 A | 5/1995 | Rupp | |
| 5,527,297 A | 6/1996 | Paul | |
| 5,562,626 A * | 10/1996 | Sanpietro | 604/110 |
| 6,077,252 A * | 6/2000 | Siegel | 604/214 |
| 6,270,482 B1 * | 8/2001 | Rosoff et al. | 604/200 |
| 6,485,471 B1 * | 11/2002 | Zivitz et al. | 604/212 |
| 2003/0097115 A1* | 5/2003 | Gruenberg | 604/500 |

* cited by examiner

Primary Examiner—Sharon Kennedy
(74) Attorney, Agent, or Firm—Robin S. Gray

(57) ABSTRACT

Syringes and methods of using are described which protect the syringe barrel cavity from contaminants. A first syringe is formed with a corrugated sheath or non-corrugated sheath which is positioned internal or external to the syringe barrel cavity. A second syringe is formed with a syringe barrel having a straight segment and a corrugated segment having the forward face of the plunger handle member molded to the rearward terminus of the corrugated segment of the syringe barrel. A third syringe is formed from mating syringe barrel and plunger member walls. The walls of the mating syringe barrel and plunger member are concentric and slide relative to each other while maintaining an enclosure around the plunger shaft. A fourth syringe is formed from inner and outer concentric syringe barrel walls mating with the walls of a plunger member. The mating walls are concentric and slide relative to each other while maintaining an enclosure around the plunger shaft. A fifth syringe is formed with an end cap contaminant shield having an extension wall that is mated with the inner wall surfaces of the syringe barrel cavity, or outer wall surfaces of the syringe barrel. Alternatively, the end cap contaminant shield can be provided with a flat design without the extending wall and is bonded or molded to the rearward end terminus of the syringe barrel. The end cap contaminant shield designs are provided with an opening defining the shape of the cross-section of the plunger shaft.

22 Claims, 12 Drawing Sheets

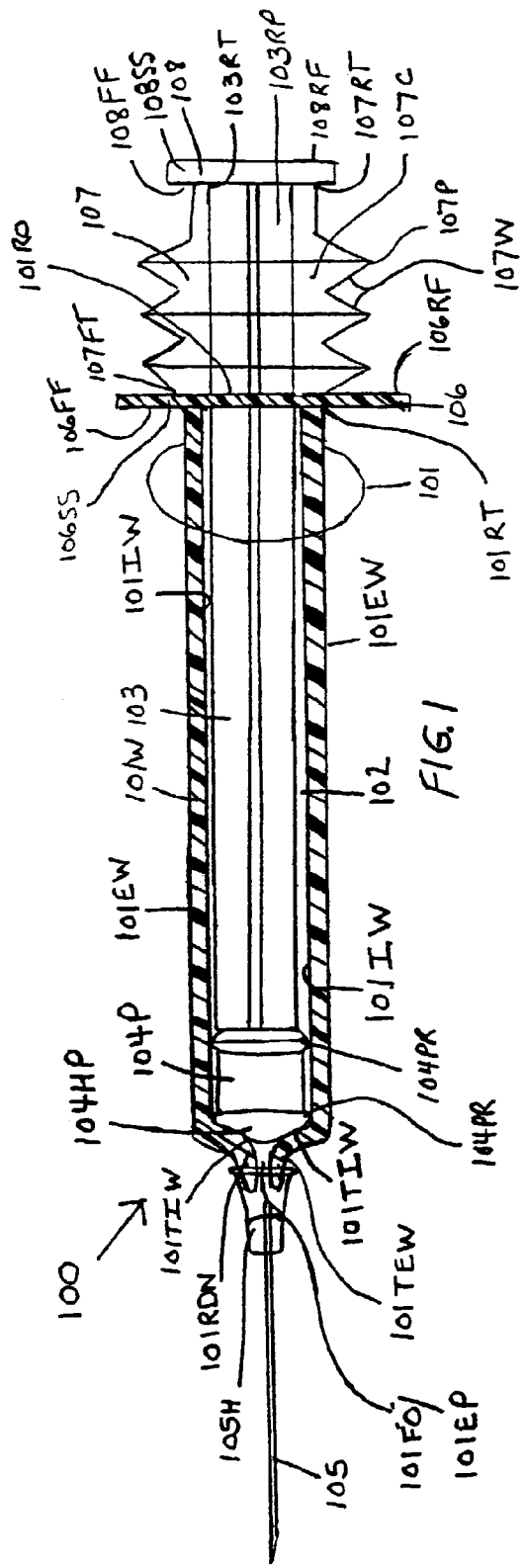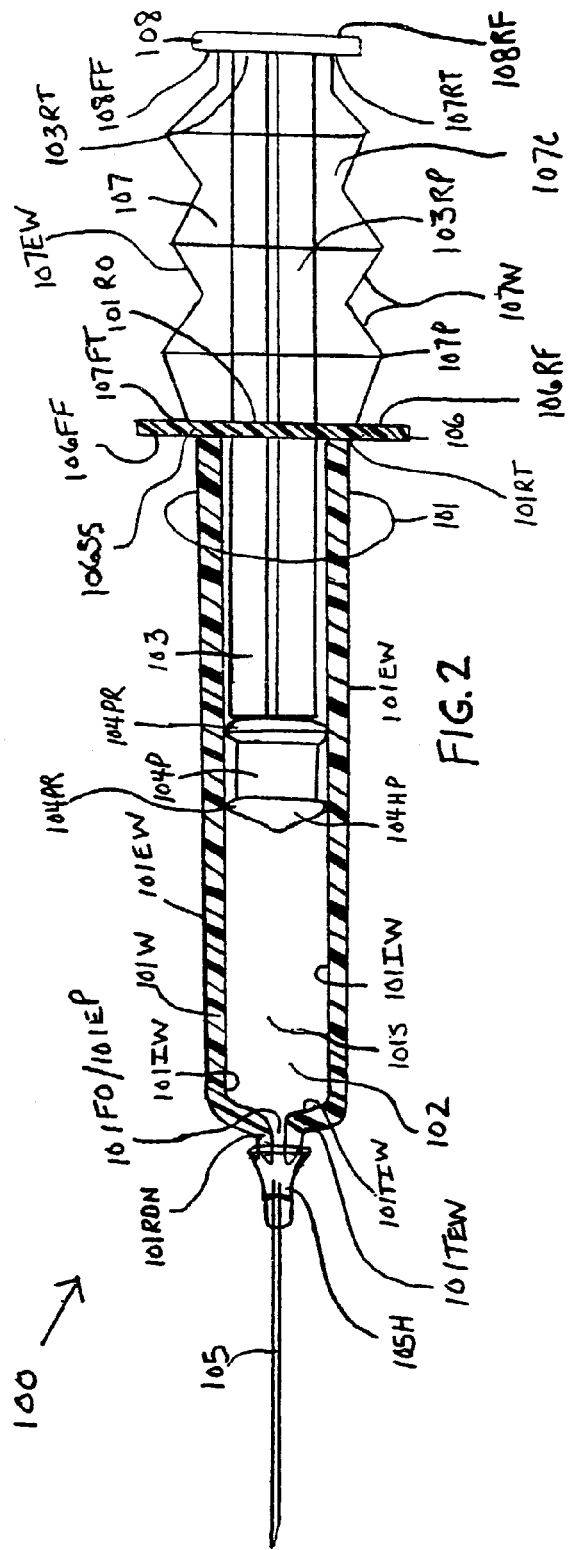

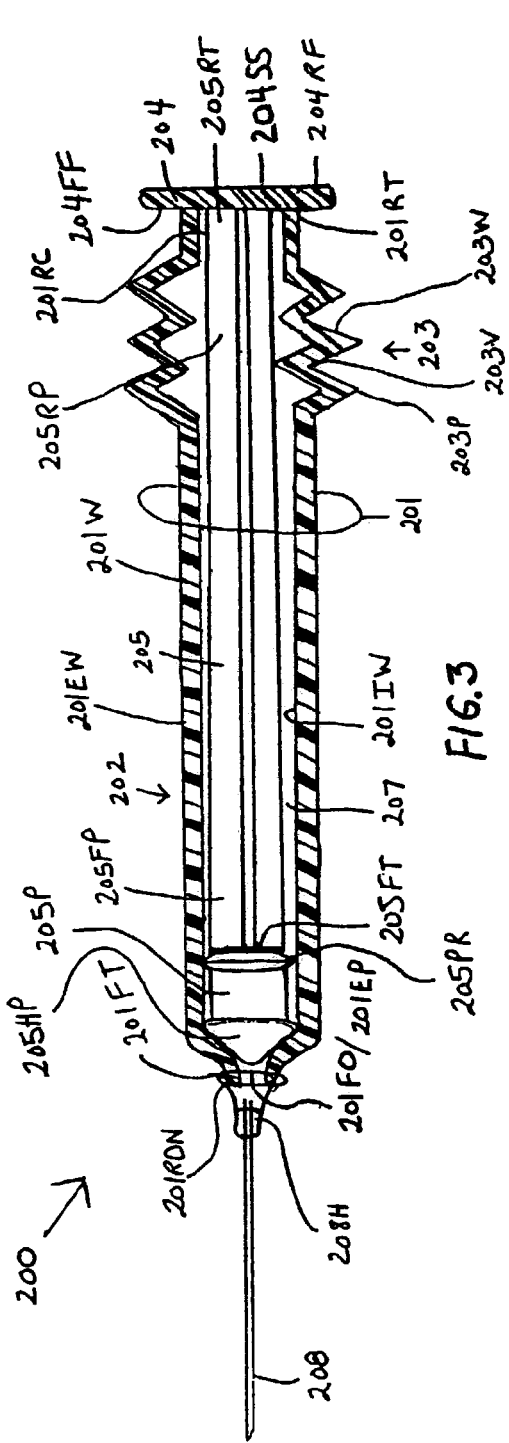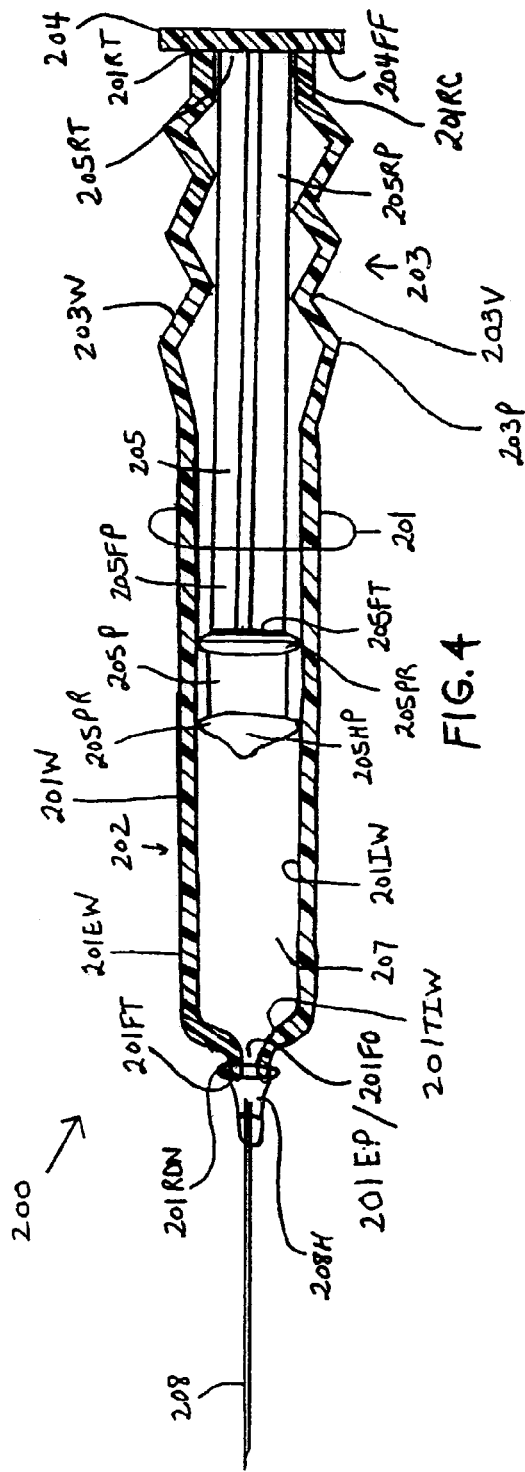

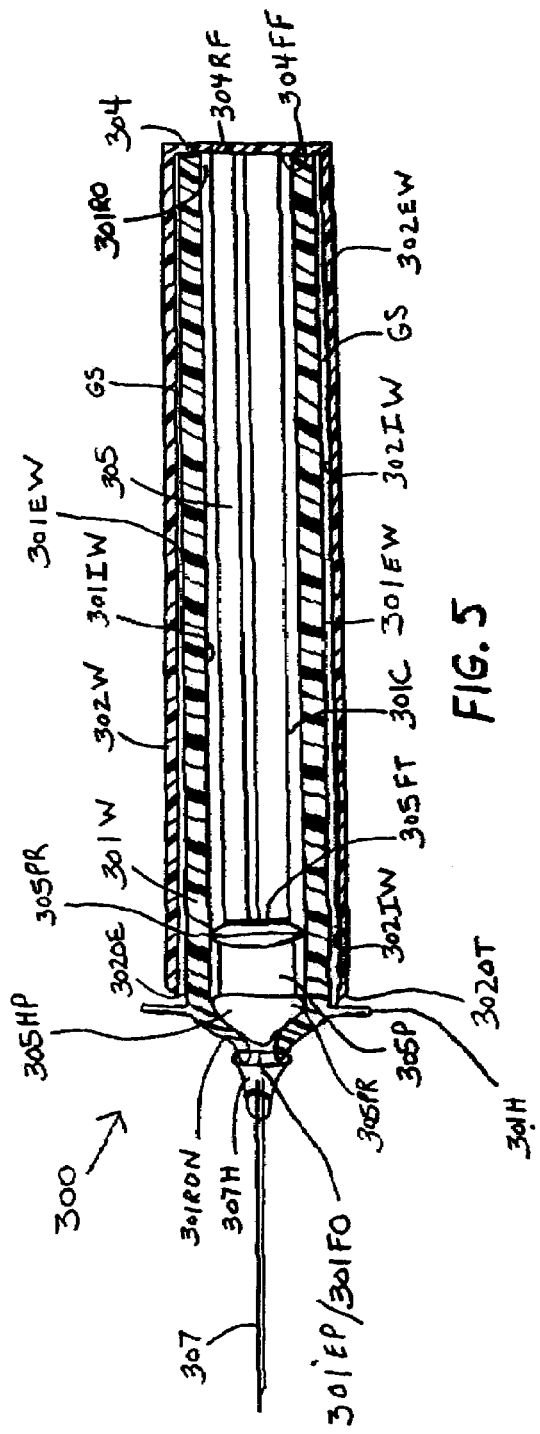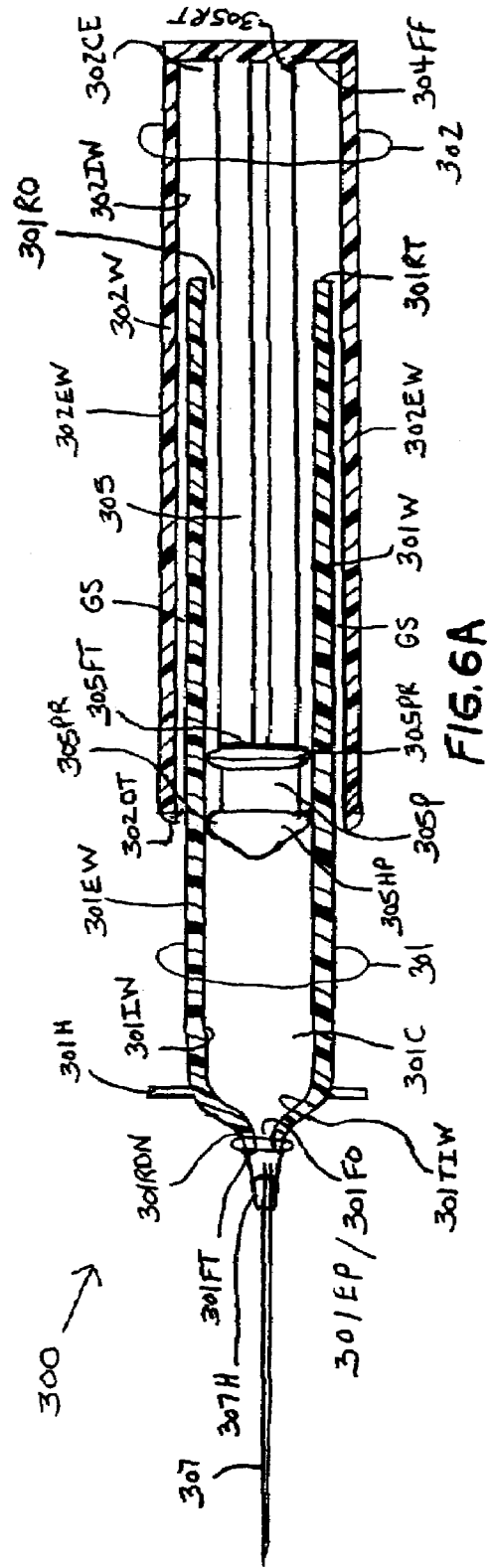
FIG. 5
FIG. 6A

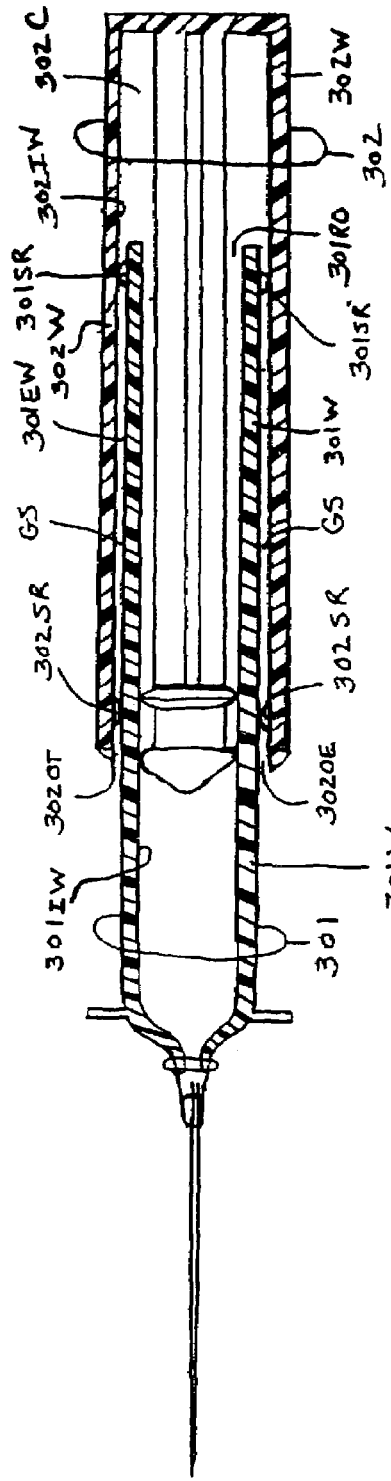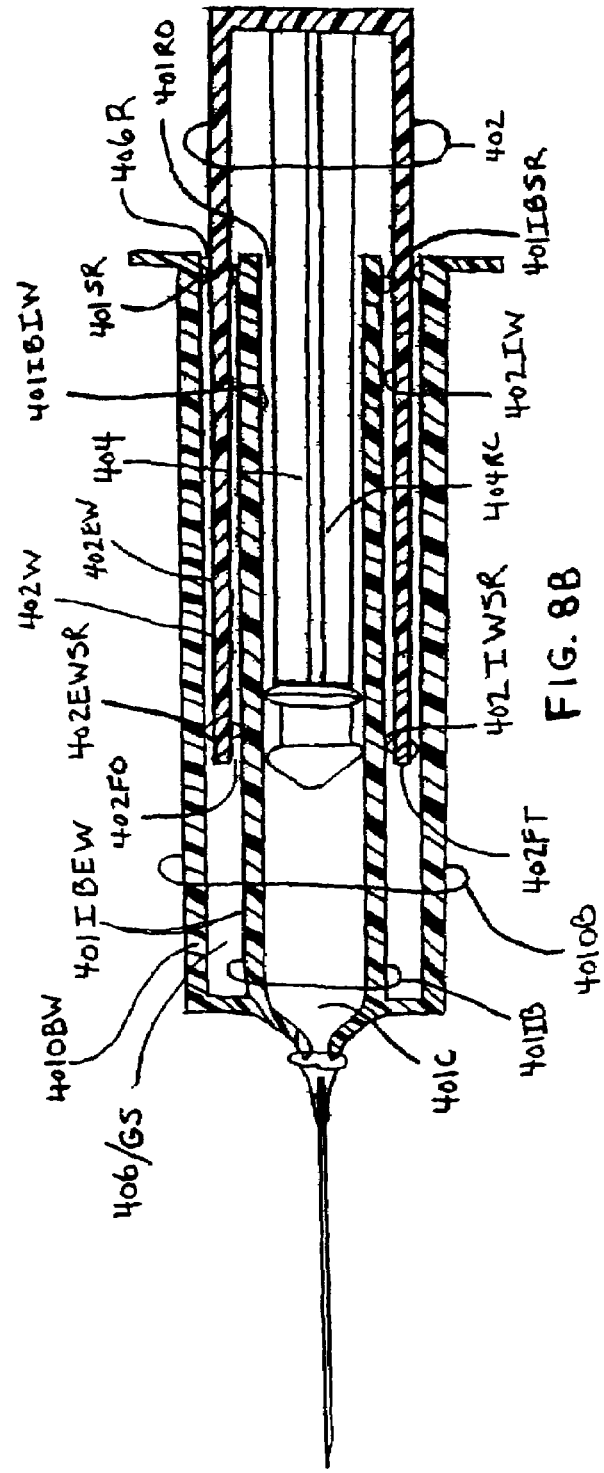

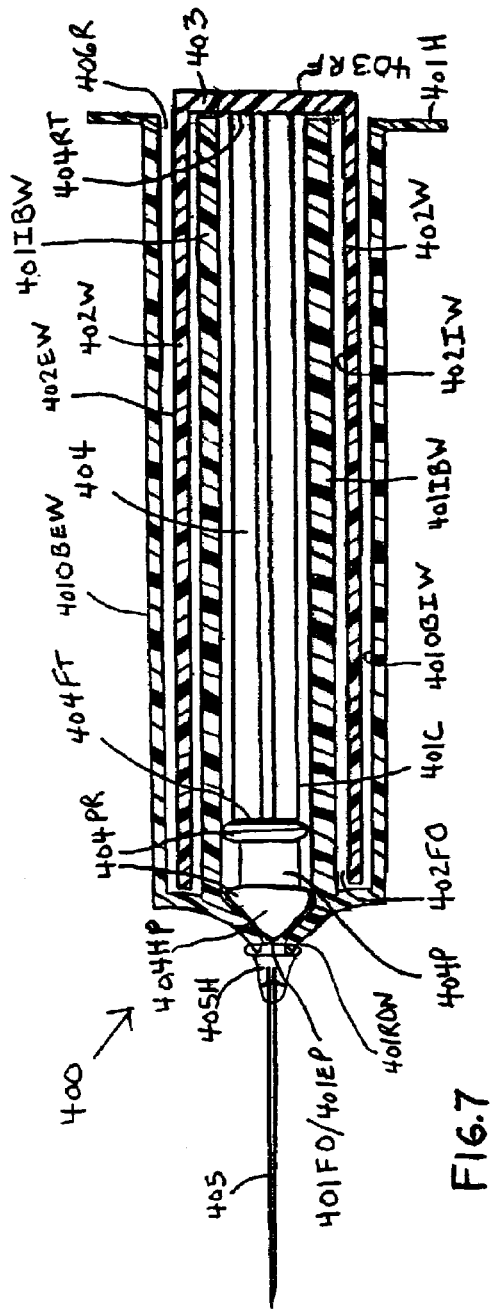
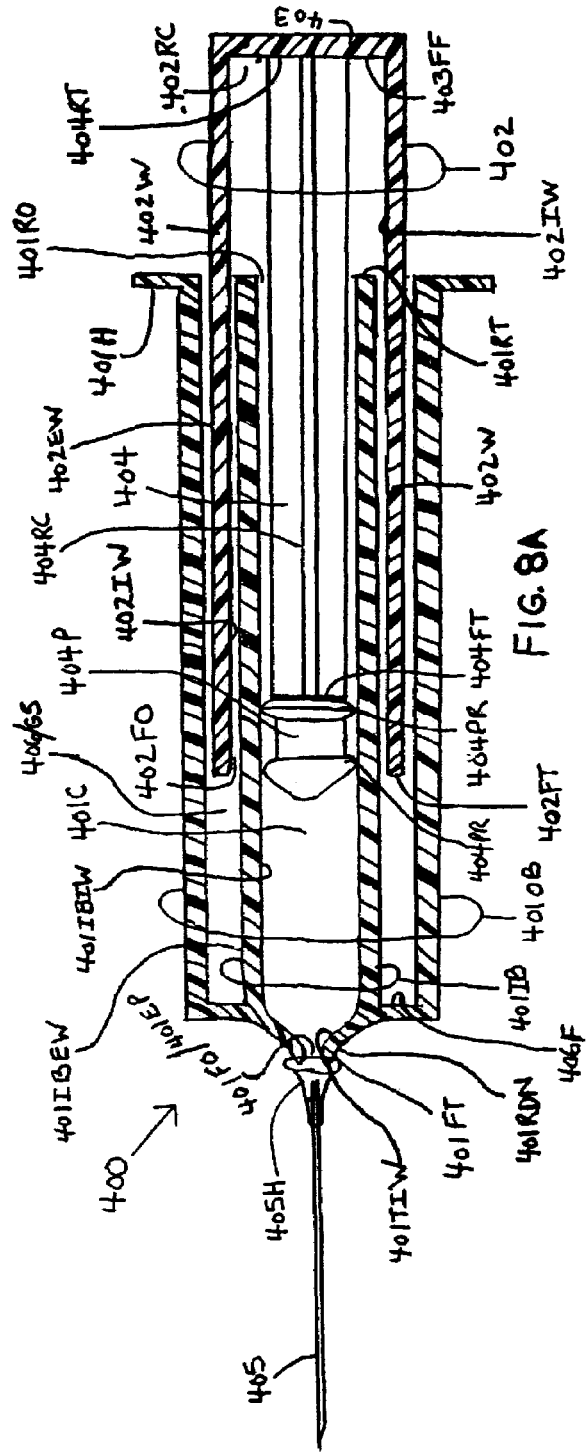

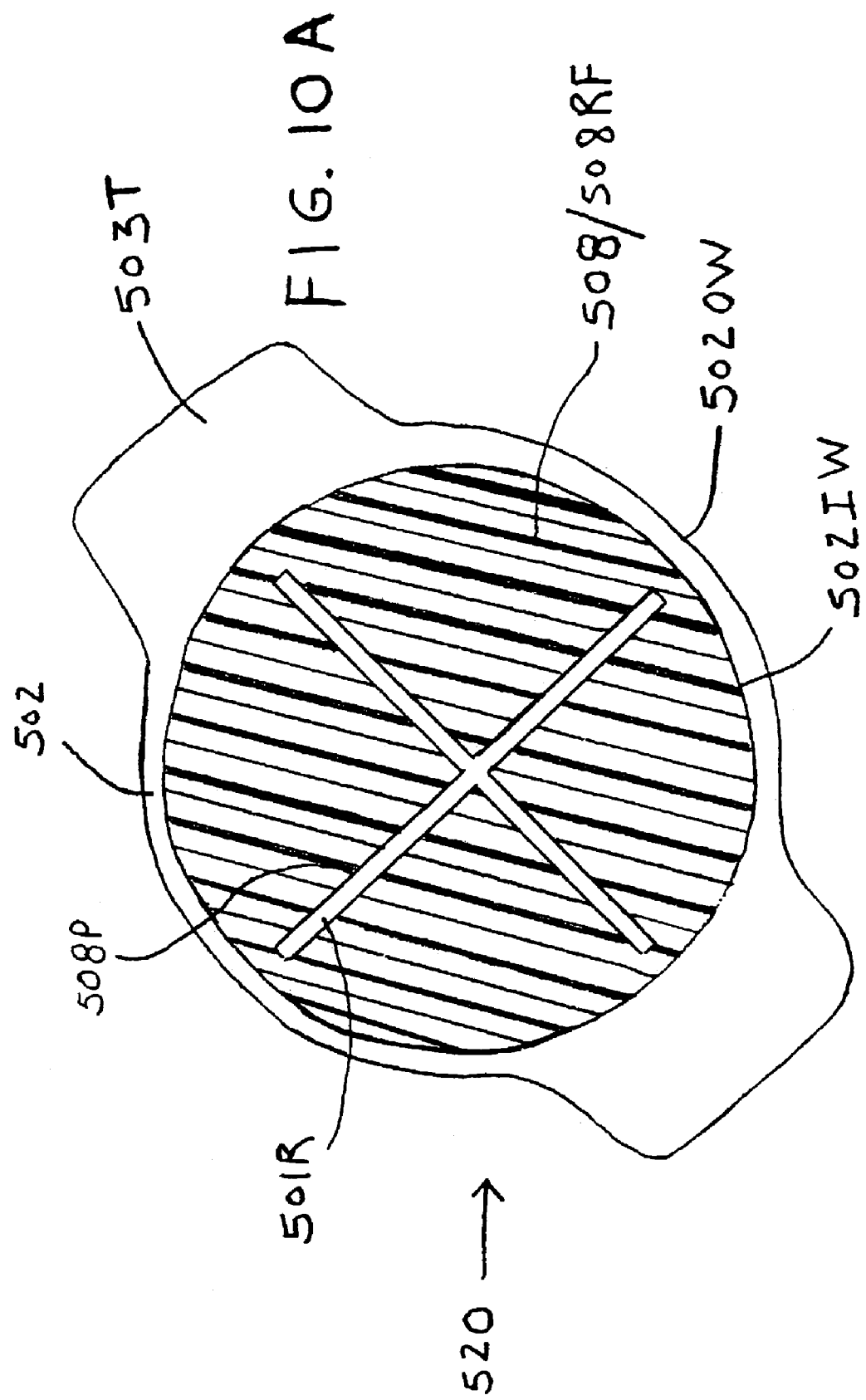

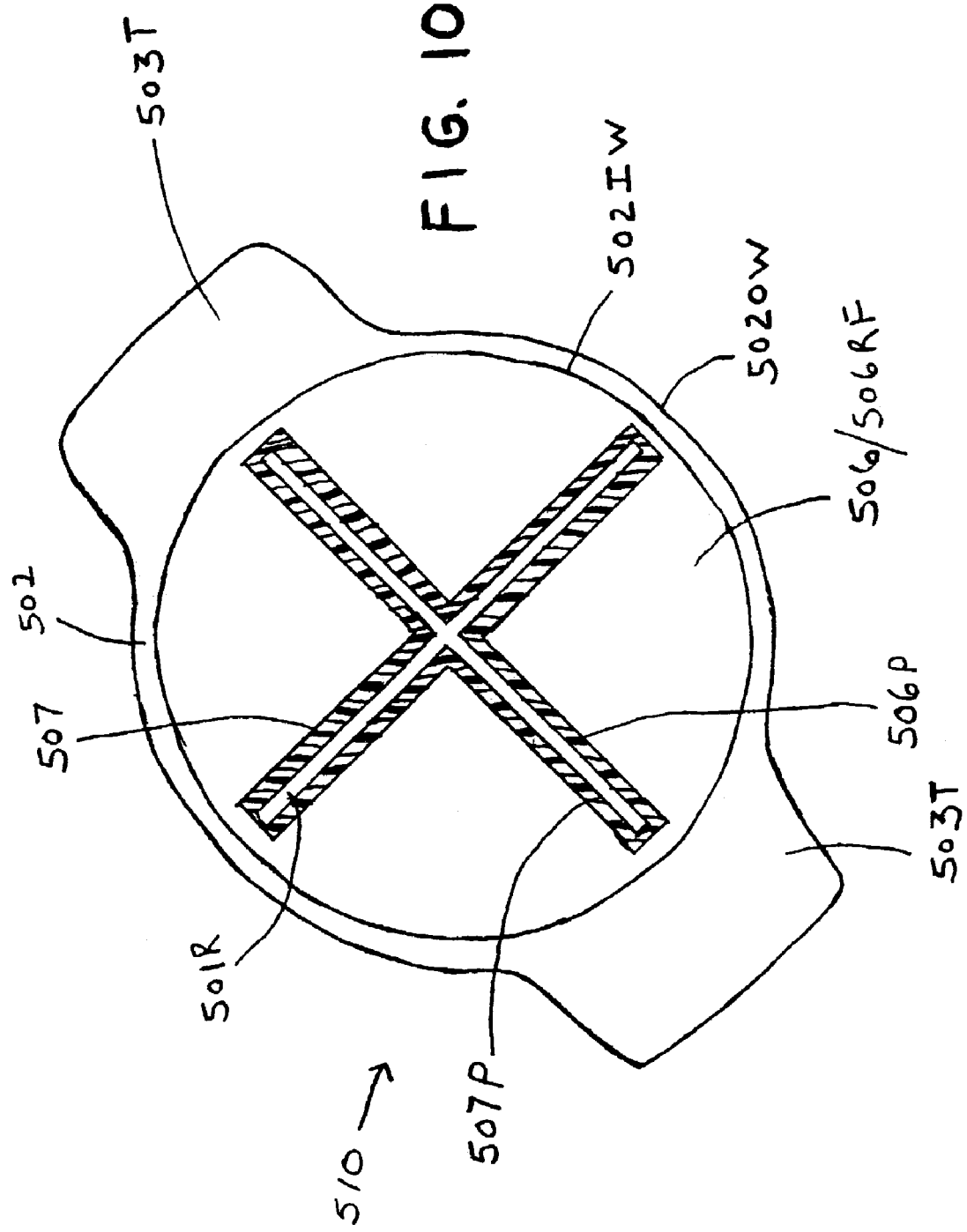

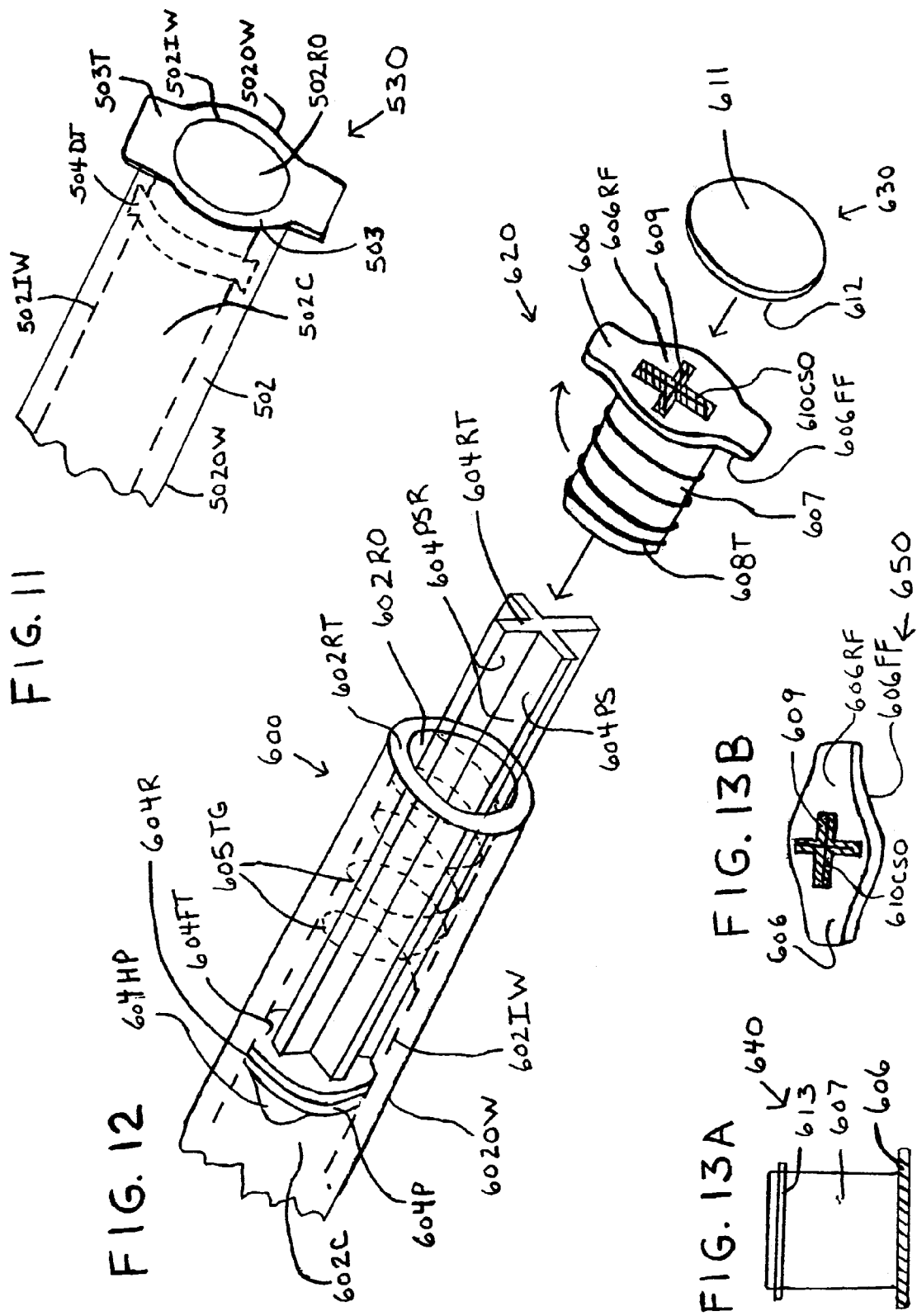

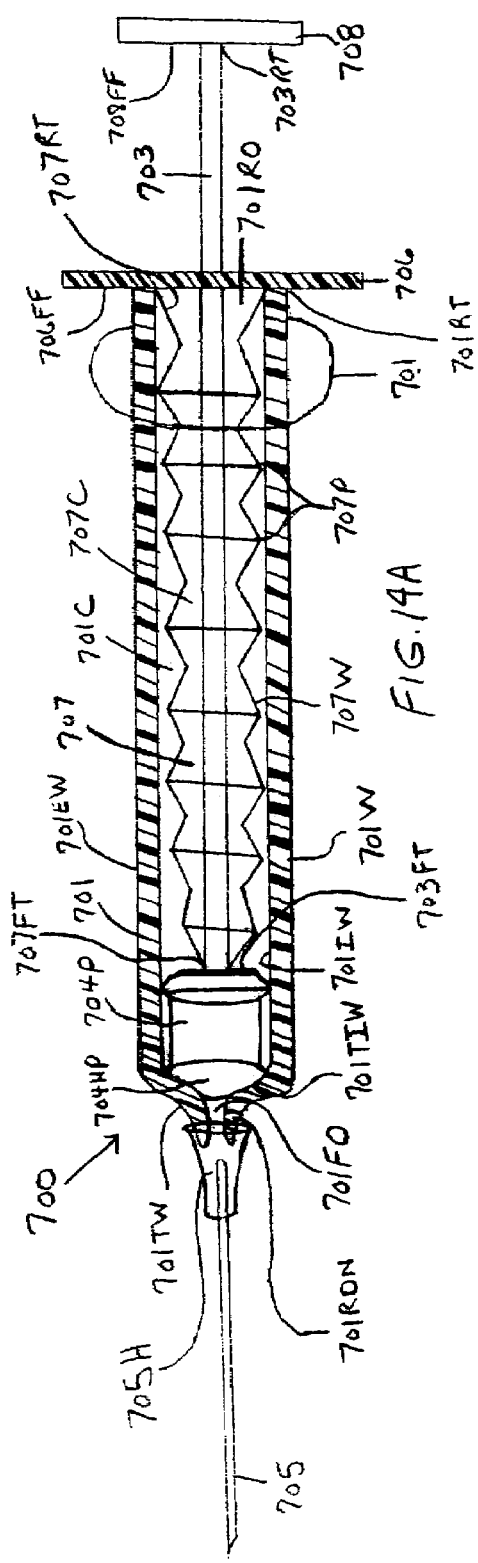
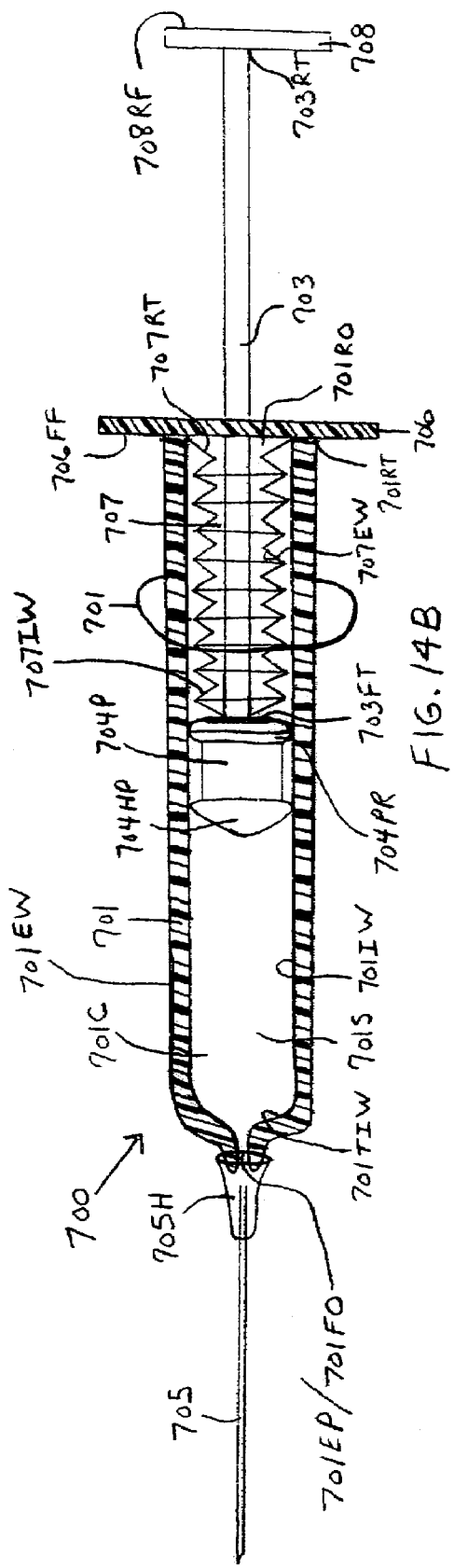
FIG. 14A
FIG. 14B

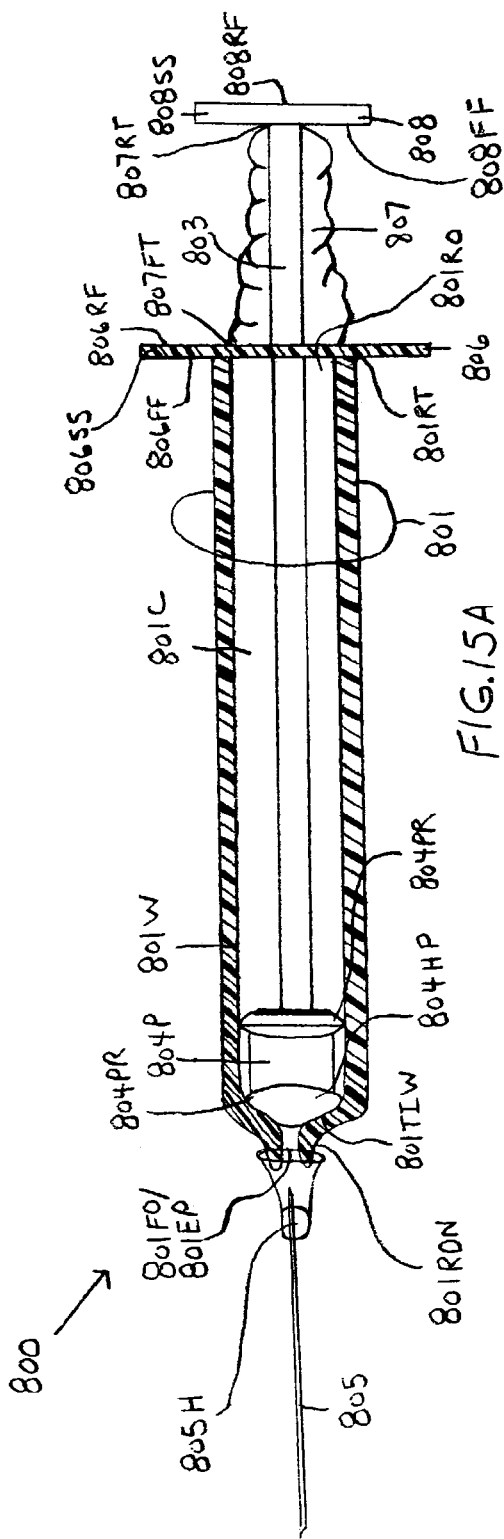
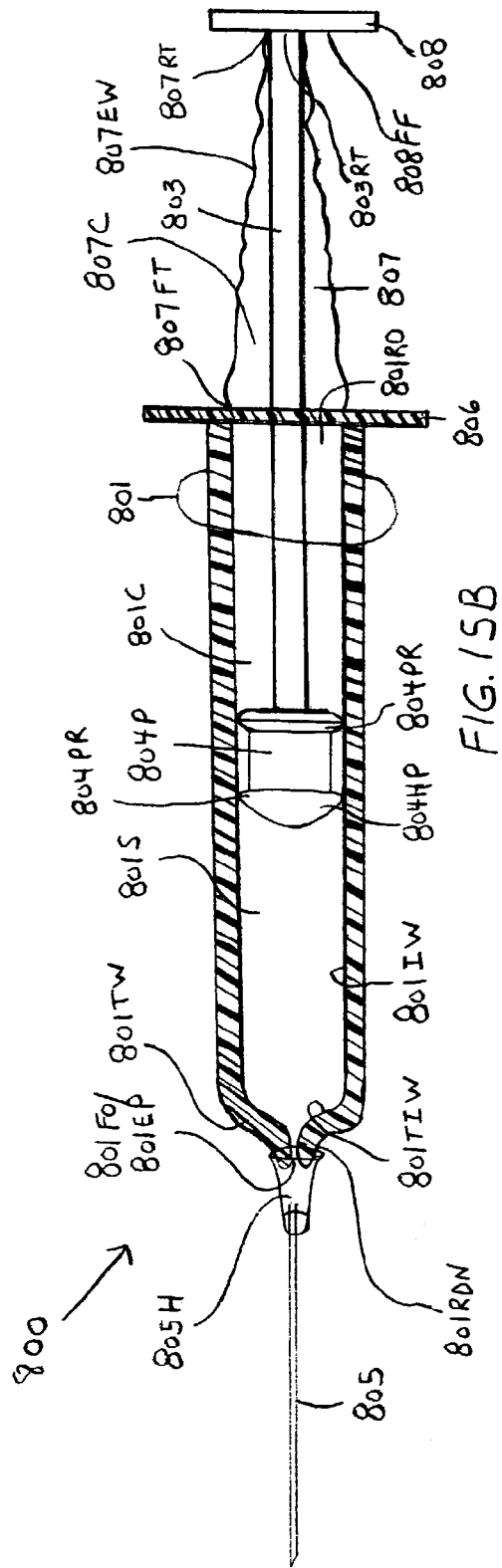
FIG. 15A
FIG. 15B

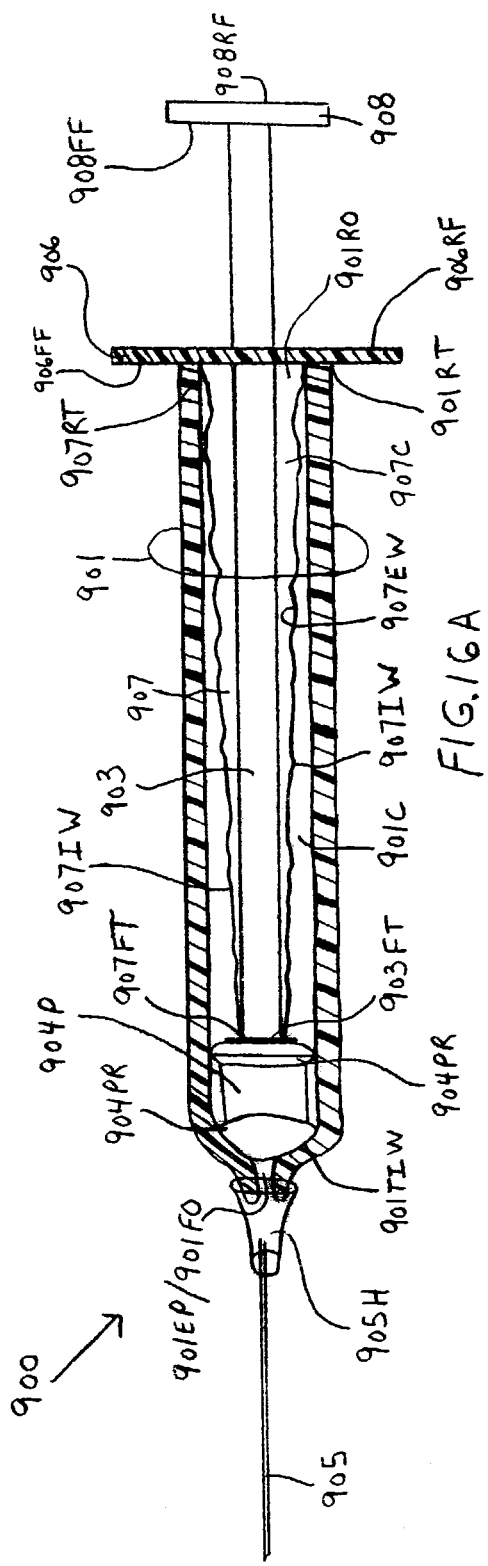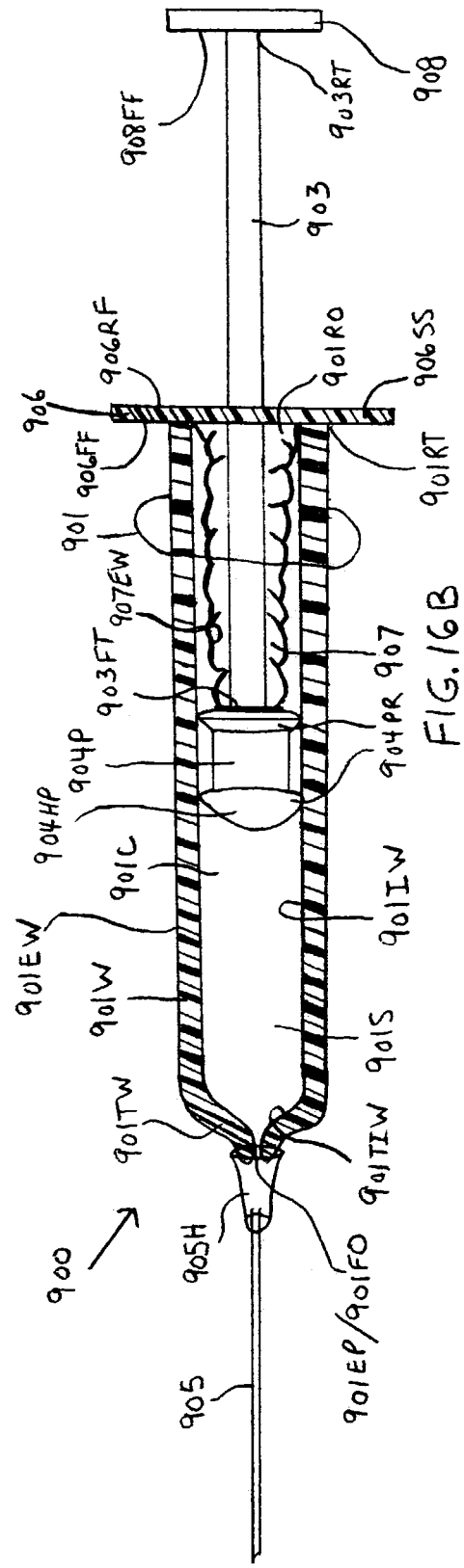

SYRINGE AND METHOD OF USING

This application is a Continuation-In-Part of U.S. application Ser. No. 10/057,519, filed on Jan. 24, 2002 now U.S. Pat. No. 6,880,564.

BACKGROUND OF THE INVENTION

Syringes are used by medical personnel to withdraw blood from patients, inject intravenous medications into patients, inject intramuscular medications into patients, prepare irrigation solutions, prepare dialysis fluids, prepare intravenous pushes, prepare bolus fluids, prepare intravenous fluids for parenteral injection, and prepare oral dose medications. Personnel trained to prepare solutions, pushes, or other fluids for injection prepare the solutions within a laminar flow hood or a vertical flow hood using aseptic technique. The hood provides a work area, which reduces the probability of contaminants being introduced into the intravenous admixtures or other solutions during their preparation, by providing clean, filtered air over the work area. Vertical flow hoods and biohazard hoods additionally reduce the probability of escape of biohazard materials being used from the work area and hood. Theses hoods are commonly found in hospital settings and used for both manufacture and incorporation of additives into parenteral and ophthalmic products. The intravenous fluids, admixtures, and other solutions are prepared by placing a bag or bottle of fluid for injection, along with a needle, syringe, and the injectable medication, into the delineated work area in the hood. The medication is drawn from an ampoule, ampul, ampule, or vial, for example, into the syringe using a needle and is then injected into the bag of intravenous fluid for injection. The fluid for injection can be a push bag, minibag, large volume parenteral, lipids or fat emulsion, etc. The bag or bottle of fluid for injection, apart from its therapeutic value, functions as a vehicle for delivering the medication, electrolytes, or other additives to the patient intravenously.

The individuals preparing the intravenous solutions are typically gowned, gloved, and use aseptic technique during the course of preparing the intravenous fluids. When preparing solutions for injection, it is necessary for the individual preparing the intravenous fluids to move their hands in and out of the laminar flow work area and also out of the laminar flow hood. Accordingly, while the hands are outside the work area and the hood, contaminants in the outside environment are introduced onto the hands or gloves of the individual preparing the intravenous solutions. In addition, the outer packaging used to hold the intravenous additives, ampoules, vials, syringes, needles, and other items used in preparing the solutions is not sterile and can carry contaminants which can be transferred or deposited onto the hands and fingers or gloves of the individual preparing the intravenous admixtures. While aseptic technique is used by the personnel preparing the solutions to reduce the tendency of introducing contaminants into the solutions being prepared, these contaminants can gain entry into the medication that has been drawn-up into the syringe barrel by their being deposited onto the inside surfaces of the syringe barrel by way of the barrel opening and/or plunger. Accordingly, care must be exercised to prevent the entry of dust, lint, dirt, hair, glass fragments, etc., and other contaminants into the syringe barrel. Although not encouraged, inadvertent contact of the plunger shaft—touch contamination—typically occurs with the hands, fingers, or gloves during the preparation of a solution. If the air, hands, fingers, hair, clothing, gloves, etc., are carrying contaminants such as dirt, lint, viruses, bacteria, microorganisms, dust, germs, pathogens, pyrogens, glass fragments, paper fibers, cloth fibers, foreign particles, hair, etc., then these contaminants can be deposited onto the plunger shaft surface and/or fall into the rearward barrel opening and subsequently be deposited onto the inner barrel walls. While a handle portion is usually located on the rearward end portion of the plunger to aid an individual in sliding the plunger into and out of the syringe barrel, larger syringes are typically difficult to handle using only one hand, or even both hands, because of the syringe size, plunger length, and friction created by surface area contact between the internal wall surfaces of the syringe barrel and the plunger piston surface. As a result, the plunger is often grasped by its shaft to gain leverage, for aiding the individual preparing the intravenous fluids, in pulling the plunger and piston along the hollow or cavity of the inner syringe barrel length to draw medication into the syringe cavity. Because the barrel end is open, grasping the plunger shaft allows contaminants present on the hands, fingers, hair, clothing, gloves, etc., to be deposited on the plunger shaft. These contaminants may also fall into the rearward end opening of the syringe barrel and come in contact with and deposit on the inner surfaces of the syringe barrel. The outside surfaces of the piston and the medication in contact with the inside syringe barrel surfaces can pick up these contaminants and ultimately deliver them to the solutions being prepared. Infusion of a pathogen or other contaminates into a patient has the potential to cause infection in the patient. Infusing or injecting solutions containing contaminate particulate matter into a patient has the potential of introducing thrombi and vessel blockage. Syringes and plungers currently in use do little to discourage the introduction of contaminants onto the plunger shaft and inner syringe barrel surface. The current syringes also suffer from problems of piston failure or detachment of the piston from the forward end of the plunger shaft causing loss of the seal between the piston and the inner surfaces of the syringe barrel. When this occurs, medication in the syringe barrel leaks or flows out of the syringe barrel rearward end opening and onto the hands, fingers, gloves, and work surface. When the material is blood or the medication or additive being used to prepare the solutions is a biohazard material such as certain chemotherapy drugs, acids, or radioactive pharmaceuticals or radiopharmaceuticals, the safety of the individual working with the material is compromised because of exposure to and contact with the hazardous material.

On occasion, nurses or other personnel are required to prepare intravenous admixtures because of a patient's immediate requirement for a medication. These admixtures are prepared in non-sterile environments and generally without the use of aseptic technique. Occasionally, it is necessary for syringes containing medication or other materials to be left at bedside in a patient's room or attached to intravenous or other types of tubing for intermittent dosing. During this time, the plunger shaft and rearward opening of the syringe barrel remain exposed to the environment increasing the probability of medication contamination. The syringes of the instant invention provide an added level of protection to the medication and patient when working in a non-sterile environment.

An additional problem which plagues current syringe designs is the problem resulting from pulling the forward end of the plunger and piston to close to the rearward end opening of the syringe barrel cavity leading to accidental separation of the plunger and piston from the barrel. Also, when the piston and forward end of the plunger are withdrawn along the syringe barrel cavity and positioned close to the rearward syringe barrel opening, the plunger shaft and medication in the syringe cavity is in increased jeopardy of contamination. Additionally, any rocking motion caused to the plunger shaft while in this position tends to compromise the seal between the piston and the syringe barrel inner surface causing leaking of the medication from the syringe barrel. The instant invention overcomes the drawbacks noted above.

SUMMARY OF THE INVENTION

This invention relates to a new and improved syringe for use in withdrawing blood from patients, injecting intravenous medications into patients, preparing pre-filled syringes with medications for injection, preparing irrigation solutions, preparing dialysis fluids, preparing intravenous pushes, preparing bolus fluids, preparing intravenous fluids, preparing sterile ophthalmics, otics, nasals, preparing large volume parenterals for intravenous injection, preparing oral dose medications, for use in automated syringe filling processes, and preparing medications requiring chemotherapy drugs, acids, radioactive pharmaceuticals or radiopharmaceuticals, for use in delivering chemicals, glue materials, food products, sauces, marinades, glazes, oils, seasonings, etc.

In a first embodiment of this invention, it is an object to provide a new and improved syringe having a corrugated or bellows sheath, cover, or shield concentrically enveloping a plunger shaft. The forward end terminus of the corrugated sheath, cover, or shield is attached or molded to at least one surface of the syringe barrel handle member. Such surfaces include but are not limited to the rearward end face surface, the forward end face surface, or the side surfaces of the syringe barrel handle member which is formed, or molded, onto the rearward end terminus of the syringe barrel. The syringe barrel handle member is attached to the rearward end terminus of the syringe barrel by one or more of the attachment methods of molding, fusing, adhesives, ultrasonic bonding or welding, thermal bonding, etc., or is molded continuous with the syringe barrel as a single unit during the forming or molding process. The rearward end terminus of the corrugated sheath, cover, or shield is attached to at least one surface of the plunger handle member, or at a position or surface along the plunger shaft. Such surfaces include but are not limited to the rearward face surface, the forward face surfaces, and the side surfaces. The plunger handle member is molded or attached to the rearward end terminus of the plunger shaft by one or more of the methods of molding, fusing, adhesives, ultrasonic bonding or welding, thermal bonding, etc., or is molded continuous with the plunger shaft as a single unit during the forming or molding process.

The rearward end terminus of the plunger shaft is centrally molded to the forward face surface of the plunger handle member with the forward end and body of the plunger shaft extending and movably fitted into the cavity, fluid reservoir, or hollow portion of the syringe barrel. The syringe barrel is formed with two open ends at opposite ends of the syringe bore or cavity—one end having a larger diameter opening than the opposite end. The larger diameter opening is located at the rearward end terminus of the syringe barrel. The smaller diameter opening functions as an entrance/exit port and is located at the forward end terminus of the syringe barrel. The forward end terminus has a reduced diameter neck at the entrance/exit port. The external surfaces of the reduced diameter neck mate with the hub of a needle. The corrugated sheath, cover, or shield encloses and surrounds the rearward end portion of the plunger shaft extending between the syringe barrel handle member and the plunger handle member. The sheath encloses and surrounds that portion of the longitudinal axis of the plunger shaft located and housed within the central cavity or hollow of the corrugated sheath and between the syringe barrel handle member or rearward end surface of the syringe barrel, and the plunger shaft handle member when the corrugated sheath is in a compressed state and in a lengthened state. Thus, the plunger shaft and rearward end syringe barrel opening are closed off from and not exposed to the outside environment. The plunger shaft can be manually withdrawn from the syringe barrel cavity or hollow by grasping the syringe barrel outer surface with one hand and the plunger shaft handle member and/or corrugated sheath outer surface with the other hand and pulling the plunger shaft handle member and/or corrugated sheath such that the plunger shaft emerges from the hollow or cavity of the syringe barrel through the rearward end opening of the syringe barrel. The peaks and walls of the corrugations, pleats, or folds in the sheath are caused to separate along the longitudinal axis of the sheath thereby lengthening the sheath along its longitudinal axis. The plunger shaft remains centrally located within the hollow of the corrugated sheath as the plunger shaft emerges from the cavity and rearward end opening of the syringe barrel. As the corrugations or folds in the sheath separate, the corrugated sheath lengthens enabling the plunger shaft to be withdrawn from the hollow or cavity of the syringe barrel. The corrugated sheath lengthens concentrically around and along the plunger shaft. That is, the corrugated sheath lengthens and encloses a greater length of the plunger shaft as the plunger shaft is further withdrawn from the syringe barrel hollow. The sheath remains in the lengthened or elongated position until a force is applied longitudinally to or along the plunger shaft to compress or collapse the folds or corrugations of the sheath together. That is, it is not necessary for an individual, or machinery when used to manipulate the syringe in an automation process, to hold the withdrawn plunger or lengthened corrugated sheath such that it remains in its lengthened state. The corrugated sheath is designed and manufactured such that it does not automatically recoil from the lengthened state to the compressed state or from the compressed state to the lengthened state. A force must be applied along the longitudinal axis of the syringe plunger shaft and/or corrugated sheath to cause the ends of the elongated corrugated walls of the sheath to be moved toward each other such that the corrugated sheath shortens. When the walls of the corrugated sheath are forced together, the sheath shortens. Shortening of the corrugated sheath can be performed by pressing or applying a force to the plunger handle member or along the corrugated sheath such that the plunger handle member advances toward the rearward end opening of the syringe barrel to cause the sheath to shorten and the plunger shaft and piston to slide along the longitudinal axis of the syringe barrel cavity toward the syringe entrance/exit port such that medication or other material in the syringe barrel cavity is ejected from the syringe through the entrance/exit port. The piston rim slidably engages and maintains a tight seal with the internal wall surfaces of the syringe barrel cavity as the piston advances. The liquid medication or other material drawn into the syringe barrel cavity remains forward of the piston head during advancement and withdrawal of the plunger and piston such that the medication or other material in the syringe barrel cavity is ejected from the syringe cavity through the entrance/exit port.

An advantage of using the corrugated sheath is the protection provided by the sheath to the plunger shaft and the internal cavity wall surfaces of the syringe barrel in that contaminants deposited onto the external wall surfaces of the corrugated sheath or syringe barrel will not jeopardize the sterility of the inner cavity of the syringe barrel because the contaminants cannot penetrate the corrugated sheath or syringe barrel. Additionally, the corrugated sheath is designed to elongate to a length that enables the piston rim to be substantially aligned with the maximum increment reading on the syringe barrel wall. This feature functions to prevent complete withdrawal and separation of the plunger shaft and piston from the syringe barrel cavity by way of the rearward end opening of the syringe barrel. The corrugated sheath may have any desired shape such as cylindrical, conical, triangular, square, etc.

A further modification using the corrugated sheath is to attach the forward end terminus of the corrugated sheath at or near the forward end terminus of the plunger shaft, and the rearward end terminus of the corrugated sheath at or near the rearward end terminus of the syringe barrel and/or syringe barrel handle member. This syringe design provides a corrugated sheath, cover, or shield positioned and housed within the syringe barrel cavity or hollow. The external surface of the corrugated sheath is exposed to the external or surrounding environment by way of the syringe barrel rearward end opening and forms a face-to-face relationship with the plunger shaft. The internal surface of the corrugated sheath is not exposed to the environment external to the syringe barrel and forms a face-to-face relationship with the internal wall surfaces of the syringe barrel cavity. The forward end terminus of the corrugated sheath, cover, or shield is attached at the forward end terminus of the plunger shaft or at a position along the longitudinal axis of the plunger shaft by one or more of the methods of molding, attachment, fusing, adhesives, ultrasonic bonding or welding, thermal bonding, etc. The rearward end terminus of the corrugated sheath, cover, or shield is attached at or near the rearward end terminus of the syringe barrel cavity opening by one or more of the methods of molding, fusing, adhesives, ultrasonic bonding or welding, thermal bonding, etc. This design eliminates contaminant entry into the syringe barrel cavity by way of the rearward end opening of the syringe barrel and eliminates the possibility of deposit of contaminants onto the internal wall surfaces of the syringe barrel or into the medication or other material contained therein.

The corrugated sheath, cover, or shield envelops or houses the portion of the plunger shaft located between the point of attachment of the forward end terminus of the corrugated sheath and the point of attachment of the rearward end terminus of the corrugated sheath. As the corrugated sheath is compressed or shortened by withdrawing the plunger shaft from the syringe barrel cavity, a shorter length of the plunger shaft is enveloped by the compressed or shortened corrugated sheath and walls of the syringe barrel cavity. As the compressed or shortened corrugated sheath is elongated or lengthened by advancing the plunger shaft into and along the syringe barrel cavity, the corrugated sheath lengthens and progressively envelopes a greater length of the plunger shaft. The forward end terminus of the corrugated sheath, cover, or shield is attached to the forward end terminus of the plunger shaft or at a position along its longitudinal length by one or more of the methods of molding, fusing, adhesives, ultrasonic bonding or welding, thermal bonding, etc. The rearward end terminus of the corrugated sheath, cover, or shield is attached at or near the rearward end terminus opening of the syringe barrel by one or more of the methods of molding, fusing, adhesives, ultrasonic bonding or welding, thermal bonding, etc. The rearward end terminus of the plunger shaft is centrally molded and normal to the forward face surface of the plunger handle member. The forward end of the body of the plunger shaft extends into the syringe barrel cavity or hollow portion of the syringe barrel. The corrugated sheath, cover, or shield houses and surrounds the portion of the plunger shaft extending between the point of attachment of the rearward end terminus of the corrugated sheath at or near the syringe barrel rearward end opening and the point of attachment of the forward end terminus of the corrugated sheath with the plunger shaft. The corrugated sheath houses, encloses, or surrounds less of the plunger shaft as the plunger shaft is withdrawn from the syringe barrel cavity while the corrugated sheath compresses at or near the syringe barrel rearward end opening. The corrugated sheath remains housed within the syringe barrel during use and operation of the syringe.

When using the syringe, the plunger shaft may be manually withdrawn from the syringe barrel cavity or hollow by grasping the external walls of the syringe barrel with one hand and the plunger shaft and/or plunger shaft handle member with the other hand and pulling the plunger shaft such that the longitudinal length of the plunger shaft traverses the cavity or hollow of the syringe barrel and progressively emerges from the rearward end opening of the syringe barrel cavity. It is noted here that the above manual operation can alternatively be performed by machinery and that touching of the plunger shaft with the hands, machinery, or other objects for this embodiment will not compromise the sterility of the inner walls of the syringe barrel because the corrugated sheath functions to impede entry of contaminants that are deposited onto the plunger shaft or external surfaces of the corrugated sheath. That is, the surfaces of the corrugated sheath that are exposed to the rearward end opening of the syringe barrel. As the plunger shaft is withdrawn from the syringe barrel cavity, the walls of the corrugated sheath surrounding the plunger shaft are caused to compress or shorten along the longitudinal axis of the corrugated sheath thereby shortening the corrugated sheath along its longitudinal axis in a direction toward the rearward end opening of the syringe barrel. This is caused by the forward terminus of the plunger shaft moving toward the rearward terminus opening of the syringe barrel and pushing the lengthened or elongated corrugated sheath toward the rearward terminus opening. The length of the plunger shaft enveloped or housed within the hollow or cavity of the corrugated sheath decreases as more of the plunger shaft emerges from the cavity and rearward end opening of the syringe barrel. As the corrugated sheath within the syringe barrel cavity compresses, the corrugated sheath shortens within the syringe barrel cavity enabling the plunger shaft to be withdrawn from the hollow or cavity of the syringe barrel. The corrugated sheath shortens and encloses, houses, or envelopes less of the plunger shaft as the plunger shaft is further withdrawn from the syringe barrel hollow. As the plunger shaft is withdrawn from the syringe barrel hollow, a space is formed between the piston head of the plunger piston and the tapered internal walls of the syringe barrel. The corrugated sheath compresses and remains in the shortened state until a force is applied along the longitudinal axis of the plunger shaft to cause the plunger shaft to advance into the syringe barrel cavity and cause the compressed corrugated sheath to lengthen or elongate. It is not necessary for an individual, or machinery when used to manipulate the syringe, to hold the withdrawn plunger shaft to ensure that the corrugated sheath remains in its shortened state. The corrugated sheath is designed and manufactured such that it does not automatically recoil or recover to its lengthened state after being compressed, or automatically recoil or recover to its compressed or shortened state after being elongated. A force must be applied along the longitudinal axis of the plunger shaft and/or corrugated sheath to cause the compressed or shortened corrugated sheath to elongate within the syringe barrel cavity. Lengthening of the corrugated sheath can be performed by applying pressure to the rearward end face surface of the plunger handle member or along the plunger shaft to advance the plunger shaft in the direction toward the forward end opening of the syringe barrel and cause the corrugated sheath to lengthen or elongate and the plunger shaft and the piston to traverse the syringe barrel cavity toward the tapered internal wall surfaces of the syringe barrel cavity and the syringe entrance/exit port. The corrugated sheath is manufactured such that it does not impede traversal of the plunger shaft and piston along the syringe barrel cavity. The piston rim slidably engages and maintains a tight seal with the internal wall surfaces of the syringe barrel cavity as the piston traverses the syringe barrel cavity. Liquid medication or other types of materials drawn into the syringe barrel cavity remain forward of the piston head during withdrawal and advancement of the plunger shaft and piston such that the medication or other types of materials drawn into the syringe barrel cavity can be ejected from the syringe barrel cavity through the entrance/exit port.

An advantage of using the corrugated sheath within the syringe barrel cavity is the protection provided by the sheath to the internal cavity wall surfaces of the syringe barrel in that contaminants deposited onto the external wall surfaces of the corrugated sheath, and/or external wall surfaces of the syringe barrel, and/or the plunger shaft will not jeopardize the sterility of the inner cavity of the syringe barrel because the contaminants cannot penetrate the walls of the corrugated sheath, the syringe barrel or shaft. Also, the design inhibits accidental or intentional separation of the plunger shaft from the rearward end opening of the syringe barrel. The corrugated sheath also functions as a dam or barrier to collect or accumulate medications, or other types of materials drawn into the syringe, that leak from the syringe barrel cavity due to piston failure.

As an alternative to the corrugated sheath, a non-corrugated or non-bellows, flexible, funnel- or taper-shaped, tubular-shaped film or lamina of one or more layers can be used. The opposite ends of the non-corrugated tubular film or lamina are molded or attached between the plunger handle member and the syringe barrel handle member in the same manner as previously described for the corrugated sheath. The non-corrugated tubular film or lamina can have any desired shape such as cylindrical, conical, square, triangular, etc. The non-corrugated film or lamina can be formed from any desired material or materials so long as the selected materials do not hinder the mechanical functioning of the syringe components. The non-corrugated tubular film functions as a sheath, cover, or shield to prevent the entry of contaminants into the syringe barrel cavity by way of the syringe barrel rearward end opening. The forward end terminus of the non-corrugated sheath can be attached to at least one surface of the syringe barrel handle member at the syringe barrel terminus. Such surfaces include, but are not limited to, the rearward end face surface, forward end face surface, or side surfaces of the syringe barrel handle member. The methods of attachment include one or more of the attachment methods of molding, fusing, adhesives, ultrasonic bonding or welding, thermal bonding, etc. The syringe barrel handle member is attached in a separate step to the rearward end terminus of the syringe barrel by one or more of the attachment methods of molding, fusing, adhesives, ultrasonic bonding or welding, thermal bonding, etc. or is molded continuous as a single unit with the syringe barrel walls during the forming and molding process. The rearward end terminus of the non-corrugated sheath is attached to at least one surface of the plunger handle member. Such surfaces include, but are not limited to, the forward end face surface, rearward end face surface, or side surfaces of the plunger shaft handle member. The methods of attachment include one or more of the attachment methods of molding, fusing, adhesives, ultrasonic bonding or welding, thermal bonding, etc. Thus, the plunger shaft and syringe barrel cavity are sealed from, and not exposed to, the external environment. The forward face surface of the plunger shaft handle member is centrally attached to the rearward end terminus of the plunger shaft in a separate step by one or more of the attachment methods of molding, fusing, adhesives, ultrasonic bonding or welding, thermal bonding, etc. or is molded continuous as a single unit with the plunger shaft during the its forming process. The non-corrugated sheath encloses and surrounds that portion of the plunger shaft extending from the syringe barrel rearward end opening. As the plunger shaft and piston are advanced further into the syringe barrel cavity toward the tapered internal walls of the syringe barrel cavity, the plunger shaft handle member advances toward the syringe barrel handle member resulting in a shorter length of the plunger shaft extending from the rearward end opening of the syringe barrel, causing the non-corrugated sheath to bunch, gather, accumulate, or collect between the syringe barrel handle member and the plunger shaft handle member while continuing to enclose and surround the length or segment of the plunger shaft extending from the rearward end opening of the syringe barrel.

Lengthening of the non-corrugated sheath is performed by withdrawing the plunger shaft from the syringe barrel cavity such that the plunger shaft and the piston traverse the syringe barrel cavity away from the tapered internal wall surfaces of the syringe barrel cavity. As the plunger shaft is withdrawn from the syringe barrel cavity, the plunger shaft handle member moves away from the syringe barrel handle member and more of the plunger shaft exits the rearward end opening of the syringe cavity causing more of the plunger shaft to extend from the rearward end opening of the syringe barrel cavity. The bunched or gathered non-corrugated sheath lengthens or elongates and ungathers or unbunches, as the plunger shaft is withdrawn, to enclose and surround the longer portion of the plunger shaft extending from the rearward end opening of the syringe barrel cavity. The length of the plunger shaft enveloped or housed within the hollow or cavity of the non-corrugated sheath increases as the plunger shaft continues to emerge from the rearward end opening of the syringe barrel. The non-corrugated sheath lengthens and longitudinally encloses or envelopes a longer length of the plunger shaft as the plunger shaft is further withdrawn from the syringe barrel hollow or cavity. As the plunger shaft is withdrawn from the syringe barrel hollow or cavity, a space is formed between the piston head of the plunger piston and the tapered internal walls of the syringe barrel. The non-corrugated sheath lengthens and remains in the elongated or lengthened state until a force is applied along the longitudinal axis of the plunger shaft to cause the plunger shaft and piston to advance into the syringe barrel cavity in a direction toward the tapered walls of the syringe barrel. It is not necessary for an individual, or machinery when used to manipulate the syringe components in an automation process, to hold the withdrawn plunger such that the non-corrugated sheath remains in its lengthened or elongated state. The non-corrugated sheath is designed and manufactured such that it does not automatically recoil or recover to its bunched or gathered state after being elongated and does not automatically recoil or recover to its elongated state after being bunched or gathered. A force must be applied along the longitudinal axis of the plunger shaft to cause the non-corrugated sheath to shorten by gathering, bunching, or accumulating the non-corrugated sheath material.

The non-corrugated sheath is manufactured such that it does not impede traversal of the plunger shaft and piston along the syringe barrel cavity. When manipulating the plunger, the piston rim slidably engages and maintains a tight seal with the internal wall surfaces of the syringe barrel cavity as the piston traverses the syringe barrel cavity. Liquid medication or other types of materials drawn into the syringe barrel cavity remain forward of the piston head during withdrawal and advancement of the plunger shaft and piston such that the medication or other types of materials drawn into the syringe barrel cavity can be ejected from the syringe barrel cavity through the entrance/exit port. In order to eject medication and other types of materials from the syringe barrel cavity, pressure can be applied to the rearward end face surface of the plunger handle member or along the plunger shaft to advance the plunger shaft and piston in the direction toward the tapered internal wall surfaces of the syringe barrel cavity. As the plunger shaft and piston advance along the syringe barrel cavity, the lengthened or elongated non-corrugated sheath gathers or accumulates. The non-corrugated sheath functions to protect the plunger shaft and the internal cavity wall surfaces from contaminants deposited onto the external wall surfaces of the non-corrugated sheath and/or syringe barrel.

An advantage of using the non-corrugated sheath is the protection provided by the sheath to the plunger shaft and the internal cavity wall surfaces of the syringe barrel in that contaminants deposited onto the external wall surfaces of the non-corrugated sheath or syringe barrel will not jeopardize the sterility of the inner cavity of the syringe barrel because the contaminants cannot penetrate the non-corrugated sheath or syringe barrel. Additionally, the non-corrugated sheath is designed to elongate to a length that enables the piston rim to be substantially aligned with the maximum increment reading on the syringe barrel wall. This feature functions to prevent complete withdrawal and separation of the plunger shaft and piston from the syringe barrel cavity by way of the rearward end opening of the syringe barrel. The non-corrugated sheath may have any desired shape such as cylindrical, conical, triangular, square, etc.

A further modification using the non-corrugated sheath is to attach the forward end terminus of the non-corrugated or non-bellows sheath at or near the forward end terminus of the plunger shaft, and the rearward end terminus of the non-corrugated sheath at or near the rearward end terminus of the syringe barrel and/or syringe barrel handle member. This syringe design provides a non-corrugated sheath, cover, or shield positioned and housed within the syringe barrel cavity or hollow. The external surface of the non-corrugated sheath is exposed to the external or surrounding environment by way of the syringe barrel rearward end opening and forms a face-to-face relationship with the plunger shaft. The internal surface of the non-corrugated sheath is not exposed to the surrounding environment external to the syringe barrel and forms a face-to-face relationship with the internal wall surfaces of the syringe barrel cavity. The forward end terminus of the non-corrugated sheath, cover, or shield is attached at the forward end terminus of the plunger shaft or at a position along the longitudinal axis of the plunger shaft by one or more of the methods of molding, attachment, fusing, adhesives, ultrasonic bonding or welding, thermal bonding, etc. The rearward end terminus of the non-corrugated sheath, cover, or shield is attached at or near the rearward end terminus of the syringe barrel cavity opening by one or more of the methods of molding, fusing, adhesives, ultrasonic bonding or welding, thermal bonding, etc. This design eliminates contaminant entry into the syringe barrel cavity by way of the rearward end opening of the syringe barrel and eliminates the possibility of deposit of contaminants onto the internal wall surfaces of the syringe barrel or into the medication or other material contained therein.

The non-corrugated sheath, cover, or shield envelops or houses the portion of the plunger shaft located between the point of attachment of the forward end terminus of the non-corrugated sheath and the point of attachment of the rearward end terminus of the non-corrugated sheath. As the non-corrugated sheath is bunched or gathered by withdrawing the plunger shaft from the syringe barrel cavity, a shorter length of the plunger shaft is enveloped by the bunched or gathered non-corrugated sheath and walls of the syringe barrel cavity. As the bunched or gathered non-corrugated sheath is elongated or lengthened by advancing the plunger shaft into and along the syringe barrel cavity, the non-corrugated sheath ungathers and progressively envelopes a greater length of the plunger shaft. The forward end terminus of the non-corrugated sheath, cover, or shield is attached to the forward end terminus of the plunger shaft or at a position along its longitudinal length by one or more of the methods of molding, fusing, adhesives, ultrasonic bonding or welding, thermal bonding, etc. The rearward end terminus of the non-corrugated sheath, cover, or shield is attached at or near the rearward end terminus opening of the syringe barrel by one or more of the methods of molding, fusing, adhesives, ultrasonic bonding or welding, thermal bonding, etc. The rearward end terminus of the plunger shaft is centrally molded and normal to the forward face surface of the plunger handle member. The forward end of the body of the plunger shaft extends into the syringe cavity or hollow portion of the syringe barrel. The non-corrugated sheath, cover, or shield houses and surrounds the portion of the plunger shaft extending between the point of attachment of the rearward end terminus of the non-corrugated sheath at or near the syringe barrel rearward end opening and the point of attachment of the forward end terminus of the non-corrugated sheath with the plunger shaft. The non-corrugated sheath houses, encloses, or surrounds less of the plunger shaft as the plunger shaft is withdrawn from the syringe barrel cavity while the non-corrugated sheath gathers or bunches at or near the syringe barrel rearward end opening. The non-corrugated sheath remains housed within the syringe barrel during use and operation of the syringe.

When using the syringe, the plunger shaft may be manually withdrawn from the syringe barrel cavity or hollow by grasping the external walls of the syringe barrel with one hand and the plunger shaft and/or plunger shaft handle member with the other hand and pulling the plunger shaft such that the longitudinal length of the plunger shaft traverses the cavity or hollow of the syringe barrel and progressively emerges from the rearward end opening of the syringe barrel cavity. It is noted here that the above manual operation can alternatively be performed by machinery and that touching of the plunger shaft with the hands, machinery, or other objects for this embodiment will not compromise the sterility of the inner walls of the syringe barrel because the non-corrugated sheath functions to impede entry of contaminants that are deposited onto the plunger shaft or external surfaces of the non-corrugated sheath. As the plunger shaft is withdrawn from the syringe barrel cavity, the walls of the non-corrugated sheath surrounding the plunger shaft are caused to bunch or gather along the longitudinal axis of the non-corrugated sheath thereby shortening the non-corrugated sheath along its longitudinal axis in a direction toward the rearward end opening of the syringe barrel. This is caused by the forward terminus of the plunger shaft moving toward the rearward terminus opening of the syringe barrel and pushing the non-corrugated sheath toward the rearward terminus opening. The length of the plunger shaft enveloped or housed within the hollow or cavity of the non-corrugated sheath decreases as more of the plunger shaft emerges from the cavity and rearward end opening of the syringe barrel. As the length of the non-corrugated sheath within the syringe barrel cavity bunches and/or gathers, the non-corrugated sheath shortens within the syringe barrel cavity enabling the plunger shaft to be withdrawn from the hollow or cavity of the syringe barrel. The non-corrugated sheath shortens and encloses or envelopes less of the plunger shaft as the plunger shaft is further withdrawn from the syringe barrel hollow. As the plunger shaft is withdrawn from the syringe barrel hollow, a space is formed between the piston head of the plunger piston and the tapered internal walls of the syringe barrel. The non-corrugated sheath bunches and/or gathers and remains in the shortened state until a force is applied along the longitudinal axis of the plunger shaft to cause the plunger shaft to advance into the syringe barrel cavity and cause the gathered and/or bunched non-corrugated sheath to lengthen. It is not necessary for an individual, or machinery when used to manipulate the syringe, to hold the withdrawn plunger shaft to ensure that the non-corrugated sheath remains in its shortened bunched and/or gathered state. The non-corrugated sheath is designed and manufactured such that it does not automatically recoil or recover to its lengthened state after being bunched and/or gathered, or automatically recoil or recover to its bunched or gathered state after being elongated. A force must be applied along the longitudinal axis of the plunger shaft and/or non-corrugated sheath to cause the bunched and/or gathered non-corrugated sheath to elongate within the syringe barrel cavity. Lengthening of the non-corrugated sheath can be performed by applying pressure to the rearward end face surface of the plunger handle member or along the plunger shaft to advance the plunger shaft in the direction toward the forward end opening of the syringe barrel and cause the non-corrugated sheath to lengthen or elongate and the plunger shaft and the piston to traverse the syringe barrel cavity toward the tapered internal wall surfaces of the syringe barrel cavity and the syringe entrance/exit port. The non-corrugated sheath is manufactured such that it does not impede traversal of the plunger shaft and piston along the syringe barrel cavity. The piston rim slidably engages and maintains a tight seal with the internal wall surfaces of the syringe barrel cavity as the piston traverses the syringe barrel cavity. Liquid medication or other types of materials drawn into the syringe barrel cavity remain forward of the piston head during withdrawal and advancement of the plunger shaft and piston such that the medication or other types of materials drawn into the syringe barrel cavity can be ejected from the syringe barrel cavity through the entrance/exit port.

An advantage of using the non-corrugated sheath within the syringe barrel cavity is the protection provided by the sheath to the internal cavity wall surfaces of the syringe barrel in that contaminants deposited onto the external wall surfaces of the non-corrugated sheath, and/or external wall surfaces of the syringe barrel, and/or the plunger shaft will not jeopardize the sterility of the inner cavity of the syringe barrel because the contaminants cannot penetrate the walls of the non-corrugated sheath, the syringe barrel or shaft. Also, the design inhibits accidental or intentional separation of the plunger shaft from the rearward end opening of the syringe barrel. The non-corrugated sheath also functions as a dam or barrier to collect or accumulate medications, or other types of materials drawn into the syringe, that leak from the syringe barrel cavity due to piston failure.

In a second embodiment of the instant invention, it is an object to provide a new and improved syringe having a corrugated barrel. The syringe barrel has a straight segment and a corrugated or bellows segment. The corrugations are molded into the syringe barrel to form the corrugated segment at a point on the barrel that is greater than the maximum volume increment reading on the straight segment of the syringe barrel. Thus, the syringe barrel has a straight segment and a corrugated segment. The straight segment is located on the forward end of the syringe barrel and the corrugated segment is located at the rearward end of the syringe barrel. The straight segment and the corrugated segment are continuous with each other. A plunger handle member is molded to rearward end of the syringe barrel at the terminus of the syringe barrel corrugated segment. The rearward end terminus of the plunger shaft is centrally molded to the forward face surface of the plunger handle member. A rearward portion of the plunger shaft body is enclosed or surrounded by the corrugated segment of the syringe barrel. The syringe barrel is formed with an open end and a closed end. The closed end is closed by the plunger handle member, which is molded to the rearward end of the syringe barrel at the terminus of the syringe barrel corrugated segment. Thus, the plunger handle member is attached to both the rear terminus of the plunger shaft and rear terminus of the syringe barrel corrugated segment. The open end is located at the forward end terminus of the syringe barrel and has a reduced diameter neck at the entrance/exit port. The external wall surface of the reduced diameter neck forms a mating surface for the hub of a needle, which can be attached frictionally to the reduced diameter neck. In addition, a circumferential wall can be formed around the external walls of the reduced diameter neck. The circumferential wall is concentric with the walls of the reduced diameter neck. Threads or grooves are formed on the inside surfaces of the circumferential wall such that the hub of the needle can be rotated or twisted on the threads or grooves and locked onto the external wall surfaces of the reduced diameter neck and within the circumferential wall. Alternatively, threads or grooves can be formed on the external wall surfaces of the reduced diameter neck and on the inner wall surfaces of the hub. The hub can then be twisted and locked onto the reduced diameter neck.

A forward end portion of the plunger shaft body and a piston located at the forward end terminus of the plunger shaft is movably fitted into and enclosed or surrounded by the straight segment of the syringe barrel. The piston and plunger shaft body can be caused to traverse the longitudinal axis of the syringe barrel cavity, fluid reservoir, or hollow by manually grasping the outer syringe barrel surface with one hand and the plunger shaft handle member and/or external walls of the corrugated segment with the other hand and pulling the plunger shaft handle member and/or corrugated segment such that the forward face surface of the plunger handle member moves away from the straight segment of the syringe barrel causing lengthening of the syringe barrel and elongation of the corrugated segment. Simultaneously, the plunger piston, mounted or attached by one or more of the methods of fusing; twisting, turning, rotating, or screwing onto threads located at the forward terminus of the plunger shaft; molding; adhesives; ultrasonic bonding or welding; thermal bonding; locking attachment; etc., to the forward end terminus of the plunger shaft, slidably engages the internal wall surfaces of the straight segment of the syringe barrel as the piston longitudinally traverses the cavity or hollow of the straight segment of the syringe barrel. In order to assist the user in lengthening of the syringe by pulling the plunger shaft handle member, a syringe barrel handle member can be molded to the external wall surface of the syringe barrel on the straight segment of the syringe barrel at a desired location. The syringe barrel handle member can be used as a wall for leverage to assist the user in lengthening or shortening the syringe barrel while pulling or pushing the plunger shaft handle and/or corrugated segment. The peaks and walls of the corrugations or folds in the corrugated segment of the syringe barrel are caused to separate or spread apart along the longitudinal axis of the syringe barrel as the plunger handle member is pulled thereby lengthening the syringe barrel along its longitudinal axis. At least a portion of the plunger shaft remains centrally located within, and the walls of the piston rim remain in contact with, the internal walls of the hollow or cavity of the syringe barrel straight segment during elongation or lengthening of the syringe barrel. The rearward end terminus of the plunger shaft and the corrugated segment rearward end terminus remain molded or attached to at least one surface of the plunger handle member or at a position or surface along the plunger shaft. Such handle member surfaces include, but are not limited to, the rearward face surface, the forward face surface, and side surfaces. The plunger handle member is molded or attached to the rearward end terminus of the plunger shaft by one or more of the methods of molding, fusing, adhesives, ultrasonic bonding or welding, thermal bonding, etc, or is molded with the plunger shaft as a single unit during the forming or molding process. It is noted that the plunger shaft handle member can be attached to the plunger shaft rearward end terminus by one or more of the methods of fusing, molding, adhesives, ultrasonic bonding or welding, thermal bonding, etc., or can be formed continuous with the plunger shaft during the molding process. After the rear terminus of the plunger shaft and plunger shaft handle member are joined or molded, the joined or molded unit can then be inserted into cavity of the straight and corrugated segments of the syringe barrel by way of an opening at the rear terminus of the corrugated segment of the syringe barrel such that the rear terminus of the corrugated segment of the syringe barrel abuts at least one surface of the plunger shaft handle member. At least one surface of the joined or molded plunger shaft/plunger shaft handle member unit is attached to the rearward terminus of the corrugated segment of the syringe barrel by one or more of the methods of fusing, molding, adhesives, ultrasonic bonding or welding, thermal bonding, etc. Alternatively, the plunger shaft with attached piston is first inserted into the cavity of the straight and corrugated segments of the syringe barrel. At least one surface of the plunger shaft handle member is then attached to the rear terminus of the corrugated segment while an additional surface can simultaneously be attached to the rear terminus of the plunger shaft using one or more of the methods of fusing, molding, adhesives, ultrasonic bonding or welding, thermal bonding, etc. for both methods.

As the corrugations or folds of the corrugated segment are caused to separate or spread apart, the corrugated segment of the syringe barrel lengthens causing the body of the plunger shaft and piston to slide along the straight segment of the syringe barrel cavity in the direction of the corrugated segment and away from the forward end of the syringe barrel. The piston rim is in contact with and forms a seal with the internal cavity walls of the syringe barrel. The corrugated segment encloses or houses and surrounds or encircles a greater length of the plunger shaft body as the plunger shaft and piston are drawn further along the syringe barrel hollow straight segment toward the corrugated segment. Once lengthened, the folds or corrugations of the corrugated segment remain in the lengthened and separated or spread apart position until a force is used to compress or collapse together the folds or corrugations of the corrugated segment. That is, it is not necessary for the individual pulling the plunger handle member and lengthening the corrugated segment to hold the plunger handle member or corrugated segment such that the corrugated segment remains in its lengthened position. The corrugated segment is designed and manufactured such that it does not automatically recoil. This design avoids automatic recoil action and maintains the corrugated segment in the desired lengthened position when drawing medications or other fluids or materials into the syringe barrel. Automatic recoil would force the medications or other fluids or materials out of the syringe barrel. An axial force must be applied to the syringe barrel along its longitudinal axis to cause the elongated corrugated segment walls to move toward each other such that the syringe barrel shortens along its longitudinal axis. When the walls of the lengthened corrugated segment are forced together, the syringe barrel shortens. Shortening of the corrugated segment can be performed by pressing against the rearward face surface of the plunger shaft handle member in a direction along the axial length of the syringe barrel to cause the corrugated segment to shorten and the plunger piston to slide along the internal side wall surfaces of the syringe barrel cavity toward the forward end and syringe entrance/exit port such that the medication or other materials in the syringe barrel cavity is ejected from the syringe through the entrance/exit port. Note that the plunger shaft remains housed within the syringe barrel during operation and non-operation. An advantage of using the straight segment and corrugated segment syringe barrel is the protection provided to the plunger shaft and the internal cavity wall surfaces in that contaminants deposited onto the external wall surfaces of the straight and corrugated segments of the syringe barrel will not jeopardize the sterility of the inner cavity of the syringe barrel because the contaminants cannot penetrate the closed walls of the syringe barrel. Additionally, the corrugated segment is designed to elongate to a length that enables the piston rim to substantially align with the maximum increment reading indicia formed on the syringe barrel straight segment. Because the rearward end terminus of the syringe barrel, at the terminus of the corrugated segment, is molded to at least one surface of the plunger handle member, and the forward face surface of the plunger handle member is also molded to the rearward end terminus of the plunger shaft, separation of the plunger from the syringe barrel is prevented.

In a third embodiment of the instant invention, it is an object to provide a new and improved syringe having mating concentric plunger member and syringe barrel walls. The plunger member has a cylindrical wall having an open end and a closed end. Shapes other than cylindrical can be used for the plunger member, syringe barrel, piston, plunger shaft, handle members, etc. The closed end of the plunger member has a flat bottom floor structure that forms a hollow cup shape with the plunger member cylindrical walls. It is noted that other shapes other than a flat shape can be provided to the bottom floor structure. The flat bottom floor structure has forward and rearward face surfaces. The flat bottom floor structure can be molded continuous with the plunger member cylindrical walls. The inside diameter of the plunger member is constant along its length. The forward face surface of the flat bottom floor structure has centrally molded thereto the rearward terminus end of a plunger shaft. The plunger shaft is concentrically surrounded by the internal wall surfaces of the plunger member. The plunger shaft extends normal from the forward face surface of the flat bottom floor structure parallel to the internal wall surfaces of the plunger member, which concentrically surround and enclose or house a desired length of the plunger shaft. The plunger shaft has a piston mounted, fused, molded, or attached to its forward end terminus by one or more of the methods of mounting; twisting, turning, rotating, or screwing onto threads located at the forward terminus of the plunger shaft; fusing; molding; adhesives; ultrasonic bonding or welding; thermal bonding; locking attachment, etc. The rim of the piston may coincide with the terminus of the plunger member walls at their open end. The syringe barrel is formed with two open ends at opposite ends of the syringe bore or cavity—one end having a larger diameter opening than the opposite end. The larger diameter opening is located at the rearward end terminus of the syringe barrel. The smaller diameter opening is located at the forward end terminus of the syringe barrel and has a reduced diameter neck at the entrance/exit port. In addition, a circumferential wall can be formed around the external walls of the reduced diameter neck. The circumferential wall is concentric with the walls of the reduced diameter neck. Threads or grooves are formed on the inside surfaces of the circumferential wall such that the hub of the needle can be rotated or twisted on the threads or grooves and locked onto the external wall surfaces of the reduced diameter neck and within the circumferential wall. Alternatively, threads or grooves can be formed on the external wall surfaces of the reduced diameter neck and on the inner wall surfaces of the hub. The hub can then be twisted and locked onto the reduced diameter neck.

The syringe barrel has an outside wall diameter less than the inside wall diameter of the plunger member along its entire length. The inside diameter of the syringe barrel is slightly less than or equal to the diameter of the rim portion of the piston. The piston is attached to the forward end terminus of the plunger shaft by one or more of the methods of mounting; twisting, turning, rotating, or screwing onto threads located at the forward terminus of the plunger shaft; fusing; molding; adhesives; ultrasonic bonding or welding; thermal bonding; locking attachment; etc, such that a tight seal is formed therebetween. The rim portion of the plunger piston mates with and forms a seal with the internal wall surfaces of the bore or cavity of the syringe barrel. The internal and external wall surfaces of the syringe barrel taper at its forward end forming the reduced diameter neck having the smaller diameter opening and an entrance/exit port through which fluid medications and/or other solutions, or other materials, enter and exit the cavity of the syringe barrel. The external wall surface of the reduced diameter neck forms a mating surface for the hub of a needle. At a point rearward of the reduced diameter neck and forward end opening of the syringe barrel, a handle member can be provided on the external syringe barrel wall for assisting the user in sliding of the plunger member relative to the syringe barrel. The plunger member is mated with the syringe barrel by movably fitting the plunger piston located at the forward end terminus of the plunger shaft into the central cavity, fluid reservoir, or bore of the syringe barrel. As the piston and plunger shaft are slid into the central cavity of the syringe barrel, the internal wall surfaces of the plunger member form a face-to-face relationship with the external wall surfaces of the syringe barrel. The plunger shaft and piston slide into the full length of the central cavity of the syringe barrel such that the head of the piston abuts the tapered internal forward end walls of the syringe barrel. The contour of the head of the piston matches and follows the contours of the tapered internal walls of the syringe barrel to form a seal at the passageway of the entrance/exit port. The terminus surfaces of the larger diameter opening of the syringe barrel can abut with the inner face surface of the flat bottom floor structure of the plunger member. In operation the walls of the outer plunger member walls concentrically surround the syringe barrel walls. In operation, medication, or other materials, is drawn up from a vial or ampoule, ampul, or ampule for example, by first introducing the needle attached to the external walls of the reduced diameter neck into the vial containing the medication or other material. Next, the internal wall surface of the plunger member is concentrically slid alongside the length of the external wall surface of the syringe barrel while maintaining a concentric glide space between the internal wall surface of the plunger member and the external wall surface of the syringe barrel. The distance between the internal wall surface of the plunger member and the external wall surface of the syringe barrel can be any desired distance. Simultaneously, as the plunger member wall is slid along the length of the syringe barrel wall, the piston attached at the forward end terminus of the plunger shaft slidably engages and maintains a tight seal with the internal wall surfaces of the syringe barrel cavity while moving along the syringe barrel cavity and away from the internal tapered walls of the syringe barrel. This causes the air column in the bore or cavity located behind the piston and along the plunger shaft to be expelled or pushed out of the cavity creating a vacuum in the space located between the forward end of the piston head and the internal tapered wall surfaces of the syringe barrel. The vacuum causes the liquid medication or other materials in the vial or ampoule, ampul, ampule, to be drawn into the syringe barrel cavity through the needle and the entrance/exit port passageway. The needle is then removed from the medication vial or ampoule, ampul, ampule, and positioned in the needle port of an appropriate bag or bottle of intravenous solution, for example. The liquid medication or other materials can then be injected into the bag or bottle of intravenous solution by applying pressure to the rearward face surface of the flat bottom floor structure. This pressure causes the longitudinal length of the plunger shaft and the plunger piston to advance along the cavity of the syringe barrel toward the tapered internal wall surfaces of the syringe cavity. The piston rim slidably engages and maintains a tight seal with the internal wall surfaces of the syringe cavity as the piston advances and withdraws. The liquid medication or other materials remain forward of the piston head during advancement and withdrawal of the plunger and piston. The liquid medication or other materials is ejected out of the entrance/exit port of the syringe barrel as the plunger and piston are advanced. An advantage of using the syringe having mating concentric plunger and syringe barrel walls is the protection provided to the plunger shaft and the internal cavity wall surfaces of the syringe barrel in that contaminants deposited onto the external wall surfaces of the plunger member or syringe barrel will not jeopardize the sterility of the inner cavity of the syringe barrel because the design discourages entry of contaminants into the syringe barrel cavity.

An added feature for the third embodiment is to provide a first sealing ring to the inner wall surface of the plunger member at or near its open-end terminus. A second sealing ring is formed on the external wall surface of the syringe barrel at or near its large diameter terminus. The sealing rings traverse the entire circumference or perimeter of the surface to which they are formed, molded, or attached. The sealing rings are preferably formed of a flexible material and extend from their surface origin a distance less than or equal to the distance to the opposing surface. The sealing rings can have any desired cross-sectional shape such as triangular, square, circular, apexed, etc. The sealing rings provide several benefits and advantages. First, the sealing rings seal the glide space existing between the internal wall surface of the plunger member and the external wall surface of the syringe barrel. This discourages entry of contaminants such as dirt, dust, microorganisms, pyrogens, glass fragments, and pathogens, etc., and any other type of contaminant carried by the air, hands, fingers, gloves, clothing, hair, etc., that may become deposited onto the external surfaces of the syringe barrel and plunger member from entering the syringe and becoming deposited on the internal walls of the syringe cavity or in the medication or other materials in the syringe barrel. Second, the sealing rings function to prevent accidental separation of the plunger member from the syringe barrel through abutment of the sealing rings as the walls of the plunger are moved relative to the walls of the syringe barrel. Third, the sealing rings function as a dam or barrier to medications or other materials and fluids that leak from the syringe cavity and collect or accumulate in the cup of the plunger member due to piston failure.

It is noted that the walls of the plunger member and syringe barrel may be any desired length. Also, the plunger shaft may be of any desired length.

In a fourth embodiment of the instant invention, it is an object to provide a new and improved syringe having concentric syringe barrels and a plunger member. The plunger member has a wall having an open end and a closed end. Any desired shape can be used for the plunger member, piston, plunger shaft, handle members, syringe barrel, etc. The closed end of the plunger member has a flat bottom floor structure that forms a hollow cup shape with the plunger member cylindrical walls. It is noted that other shapes other than a flat shape can be provided to the bottom floor structure. The flat bottom floor structure has forward end and rearward end face surfaces. The flat bottom floor structure can be molded continuous with the walls of the plunger member. The inside diameter of the plunger member walls is constant along their length. The forward end face surface of the flat bottom floor structure has centrally molded thereto the rearward terminus end of a plunger shaft. The plunger shaft can also be molded continuous with the flat bottom floor structure during the forming and molding process. The plunger shaft is centrally located within and surrounded by the internal wall surfaces of the plunger member. The plunger shaft extends centrally and normal from the forward face surface of the flat bottom floor structure parallel to the plunger member walls. The walls of the plunger member extend normal from the plane of the forward end face surface of the flat bottom floor structure and concentrically surround a desired length of the plunger shaft. The plunger shaft has a piston attached by one or more of the methods of mounting; twisting, turning, rotating, or screwing onto threads located at the forward terminus of the plunger shaft; fusing; molding; adhesives; ultrasonic bonding or welding; thermal bonding; locking attachment, etc., to its forward end terminus. The rim of the plunger piston may coincide with the terminus of the walls of the plunger member at its open end. The concentric syringe barrel is formed with inner and outer syringe barrels. An inner concentric syringe barrel is formed with two open ends located at opposite ends of the inner concentric syringe barrel cavity—one end having a larger diameter opening than the opposite end. The larger diameter opening is located at the rearward end terminus of the inner concentric syringe barrel. The smaller diameter opening is located at the forward end terminus of the concentric syringe barrel and has a reduced diameter neck at the entrance/exit port. The inner syringe barrel has an outside diameter less than the inside diameter of the plunger member walls along the entire length of the inner syringe barrel. The inside diameter of the inner syringe barrel is equal to or slightly less than the diameter of the rim portion of the plunger piston which is attached by one or more of the methods of mounting; twisting, turning, rotating, or screwing onto threads located at the forward terminus of the plunger shaft; fusing; molding, adhesives; ultrasonic bonding or welding; thermal bonding; locking attachment; etc., to the forward end terminus of the plunger shaft. The rim portion of the plunger piston mates with and forms a seal with the internal wall surfaces of the bore or cavity of the inner syringe barrel. The internal and external wall surfaces of the inner syringe barrel taper at their forward ends forming the reduced diameter neck having the smaller diameter opening and an entrance/exit port through which fluid medications and other solutions or fluids or other materials enter and exit the cavity of the inner syringe barrel. The external wall surface of the reduced diameter neck forms a mating surface for the hub of a needle. In addition, a circumferential wall can be formed around the external walls of the reduced diameter neck. The circumferential wall is concentric with the walls of the reduced diameter neck. Threads or grooves are formed on the inside surfaces of the circumferential wall such that the hub of the needle can be rotated or twisted on the threads or grooves and locked onto the external wall surfaces of the reduced diameter neck and within the circumferential wall. Alternatively, threads or grooves can be formed on the external wall surfaces of the reduced diameter neck and on the inner wall surfaces of the hub. The hub can then be twisted and locked onto the reduced diameter neck.

An outer syringe barrel concentrically encircles the inner syringe barrel forming concentric syringe barrels. The internal wall surfaces of the outer syringe barrel are in face-to-face relationship with the external wall surfaces of the inner syringe barrel and are separated by a distance, which forms a second cavity or space between the inner syringe barrel wall and the outer syringe barrel wall. This second cavity or space is open at its rearward end and closed at its forward end forming a cup shape. The open end of the second cavity receives the walls of the plunger member. This second cavity or space functions as a glide space for the walls of the plunger member. At a point located at or near the rear terminus opening on the external wall surface of the outer syringe barrel, a handle member can be provided for assisting the user in sliding the plunger member relative to the inner and outer syringe barrels.

The plunger member is mated with the concentric syringe barrel member by movably fitting the plunger piston, located at the forward end terminus of the plunger shaft, into the central cavity, fluid reservoir, or bore formed by the inner syringe barrel walls. As the piston and plunger shaft are slid into the central cavity of the inner syringe barrel, the internal wall surfaces of the plunger member form a face-to-face relationship with the external wall surfaces of the inner syringe barrel. Also, the external wall surfaces of the plunger member form a face-to-face relationship with the internal wall surfaces of the outer syringe barrel. The plunger shaft and piston slide into the full length of the central cavity of the inner syringe barrel such that the head of the piston abuts the tapered internal walls of the inner syringe barrel. The contour of the head of the piston matches and follows the contours of the tapered internal walls of the inner syringe barrel to form a seal at the passageway of the entrance/exit port. The terminus surfaces of the larger diameter opening of the inner syringe barrel can abut with the inner face surface of the flat bottom floor structure of the plunger member. In operation, the walls of the concentric syringe barrels concentrically surround the plunger member walls. Medication or other material is drawn up from a vial or ampoule, ampul, ampule, for example, by first introducing the needle, attached to the external walls of the reduced diameter neck of the entrance/exit port, into the vial or ampoule, ampul, ampule, containing the medication. Next, the longitudinal wall surfaces of the plunger member are concentrically slid within the glide space existing between and along the length of the external wall surface of the inner syringe barrel and the internal wall surface of the outer syringe barrel. Simultaneously, as the plunger member wall is slid within the glide space along the length of the external wall surface of the inner syringe barrel and the inner wall surface of the outer syringe barrel, the piston attached at the forward end terminus of the plunger shaft slidably engages and maintains a tight seal with the internal wall surfaces of the inner syringe barrel cavity while moving along the inner syringe barrel cavity and away from the internal tapered walls of the inner syringe barrel. This causes the air column in the bore or cavity located behind the piston and along the plunger shaft to be pushed out of the cavity creating a vacuum in the space located between the forward end of the piston head and the tapered internal wall surfaces of the inner syringe barrel. The vacuum causes the liquid medication or other materials in the vial or ampoule, ampul, ampule, to be drawn into the inner syringe barrel cavity through the needle and the entrance/exit port passageway. The needle is then removed from the medication vial or ampoule, ampul, ampule, and positioned in the needle port of an appropriate bag or bottle of intravenous solution. The liquid medication or other material can then be injected into the bag or bottle of intravenous solution by applying pressure to the rearward face surface of the flat bottom floor structure. This pressure causes the longitudinal length of the plunger shaft and the plunger piston to advance along the cavity of the inner barrel of the syringe toward the tapered internal wall surfaces of the inner barrel syringe cavity. The piston rim slidably engages and maintains a tight seal with the internal wall surfaces of the inner syringe barrel cavity as the piston advances. The liquid medication or other material remains forward of the piston head during advancement and withdrawal of the plunger and piston. The liquid medication or other materials is ejected out of the entrance/exit port of the syringe cavity of the inner barrel as the plunger is advanced.

An advantage of using a syringe having concentric inner and outer syringe barrels which mate concentrically with a plunger member is the protection provided to the plunger shaft and the internal cavity wall surfaces of the syringe in that contaminants deposited onto the external wall surfaces of the plunger member or syringe barrel will not jeopardize the sterility of the cavity of the inner syringe barrel because the design discourages entry of contaminants into the inner syringe barrel cavity.

An added feature for the fourth embodiment is to provide a first sealing ring to the internal wall surface of the outer syringe barrel at or near its open-end terminus. A second sealing ring can be formed on the external wall surface of the plunger member at or near the terminus of its open end. A third sealing ring can be formed on the internal wall surface of the plunger member at or near the terminus of its open end. Fourth and fifth sealing rings can be formed on the internal and external surfaces of the inner syringe barrel at or near the terminus of its open end. One or more of the above sealing rings can be formed or provided on the wall surfaces of the concentric syringe barrels or plunger member. The sealing rings traverse the entire circumference or perimeter of the surface to which they are formed or molded. The sealing rings provide several advantages. The sealing rings are preferably formed of a flexible material and extend from their surface origin a distance less than or equal to the distance to the opposing surface. The sealing rings can have any desired cross-sectional shape such as triangular, square, circular, apexed, etc. The sealing rings provide several benefits. First the sealing rings function as a barrier by sealing the glide space existing between the internal wall surface of the outer syringe barrel and the external wall surface of the inner syringe barrel. This discourages entry of contaminants such as dirt, microorganisms, dust, pathogens, pyrogens, glass fragments, etc., and other types of contaminants, carried by air, hands, fingers, gloves, hair, clothing, etc., which may become deposited onto the internal surfaces of the inner syringe barrel cavity. Second, the sealing rings function to prevent separation of the plunger member from the concentric syringe barrels through abutment of the sealing rings on the syringe barrels with the sealing rings of the plunger member as the walls of the plunger member are moved relative to the walls of the inner and outer concentric syringe barrels. Third, the sealing rings function as a dam or barrier to fluids that leak from the syringe barrel cavity and collect or accumulate in the cup of the plunger member due to piston failure.

It is noted that the inner and outer walls of the syringe barrel and plunger member may be of any desired length. Also, the plunger shaft may be of any desired length.

In a fifth embodiment of the instant invention, it is an object to provide a new and improved syringe having a contaminant shield positioned at the rearward end opening of the syringe barrel. The contaminant shield is formed on the rearward end syringe barrel inner wall surface using a semi-rigid and flexible material. The contaminant shield projects perpendicularly from the circumference or perimeter of the syringe barrel inner wall surfaces into the syringe barrel cavity and surrounds and abuts the surfaces and walls of the ribs which form the spine of the plunger shaft. Alternatively, the plunger shaft can have a shape or design features other and ribs. The contaminant shield is designed and molded to surround and abut the shaped surfaces and walls of the plunger shaft. The contaminant shield can be formed from a single material or a mixture or combination of materials, which will provide a semi-rigid and flexible characteristic to the shield. To facilitate attachment of the contaminant shield to the inner wall surface of the syringe barrel cavity, a dovetail groove, or similar locking groove, can be formed in the surface of the syringe barrel inner wall along the circumference or perimeter at or near the rearward end opening of the syringe barrel during the forming process for the syringe barrel. During the molding process of the contaminant shield, the dovetail groove receives and anchors the material used to form the contaminant shield. The contaminant shield has a forward end face surface facing the cavity of the syringe barrel and a rearward end face surface facing the plunger handle member.

Alternatively, the shield can be formed of two parts. The first part is formed of a material providing a rigid or hard characteristic or quality to the contaminant shield. The first part can be formed of the same material and molded continuous with the circumference of the inner wall surface of the syringe barrel at or near the rearward end opening of the syringe barrel. The first part, when formed, projects into the syringe barrel cavity perpendicularly from the circumference or perimeter of the inner wall surface of the syringe barrel. The first part has a forward face surface and a rearward face surface. The first part has centrally formed therethrough an opening having the shape of the cross-section of the plunger shaft used in conjunction with the syringe barrel. If the contaminant shield is formed separately, or with a different material than that used to form the syringe barrel cavity, then a dovetail groove, or similar locking groove, can be formed on the inner wall surface of the syringe barrel along the circumference or perimeter of the syringe barrel inner wall surface at or near the rearward end opening of the syringe barrel. During the molding process, the dovetail groove receives and anchors the material used to form the first part of the contaminant shield.

The second part of the contaminant shield is formed from a soft, flexible material that has a bendable characteristic. The second part is formed within the cross-sectional opening on the periphery of the first part. The second part projects from the periphery or edges of the first part and into the cross-sectional opening. The second part terminates as a flexible lip, edge, or periphery that defines the plunger shaft cross-sectional opening. During operation or use, the lip, edge, or periphery of the second part is in contact with the surfaces of the plunger shaft, which fits within the cross-sectional opening and traverses the opening as the plunger shaft exits and enters the syringe barrel cavity. The second part is formed on the cross-sectional periphery of the first part. This can be accomplished by providing the external surface of the first part, at its edge or periphery, with a dovetailed shape, or other surface shapes such as slits or holes, which would provide a locking function to the cross-sectional periphery of the first part during its forming operation to which the second part can be formed about. Alternatively, a dovetailed groove or similar locking groove can be provided at and within the cross-sectional periphery or edge of the first part to receive and anchor the material used to form the second part of the contaminant shield. Thus, the material used to form the second part can be molded directly to the periphery of the first part or the first part and second part can be molded separately and then interlocked together. The rearward end terminus of the plunger shaft is centrally molded to the forward face surface of a plunger handle member with the body of the plunger shaft extending through the cross-sectional opening formed in the contaminant shield. The forward end terminus of the plunger shaft has a piston that is attached or formed thereto by one or more of the methods of mounting: twisting, turning, rotating, or screwing onto threads located at the forward terminus of the plunger shaft; fusing; molding; adhesives; ultrasonic bonding or welding; thermal bonding; locking attachment; etc, and, along with the plunger shaft, is movably fitted into the cavity, fluid reservoir, or hollow portion of the syringe barrel. The syringe barrel is formed with two open ends located at opposite ends of the syringe cavity. The rearward end of the syringe barrel has a plunger shaft cross-sectional opening as described above and the forward end terminus has a small diameter opening. The small diameter opening has a reduced diameter neck at the entrance/exit port. The external wall surface of the reduced diameter neck forms a mating surface for the hub of a needle to which the hub of a needle can be attached with a frictional fit. Alternatively, a circumferential wall can be formed around the external walls of the reduced diameter neck. The circumferential wall is concentric with the walls of the reduced diameter neck. Threads or grooves are formed on the inside surfaces of the circumferential wall such that the hub of the needle can be rotated or twisted on the threads or grooves and locked onto the external wall surfaces of the reduced diameter neck and within the circumferential wall. Alternatively, threads or grooves can be formed on the external wall surfaces of the reduced diameter neck and on the inner wall surfaces of the hub. The hub can then be twisted and locked onto the reduced diameter neck.

In operation, the plunger shaft can be manually withdrawn from the syringe barrel cavity by grasping the outer syringe barrel surface with one hand and the plunger shaft handle member with the other hand and pulling the plunger shaft handle member such that the plunger shaft emerges from the hollow or cavity of the syringe barrel through the rearward end plunger shaft cross-sectional opening formed in the contaminant shield exposing the plunger shaft previously housed within the syringe barrel cavity to the external environment. During withdrawal, the piston at the forward end terminus of the plunger shaft slidably engages and maintains a tight seal with the internal wall surfaces of the syringe barrel cavity while moving along the syringe barrel cavity and away from the internal tapered walls of the syringe barrel located at the forward end of the syringe barrel. This causes the air column in the bore or cavity behind the piston head and along the plunger shaft to be expelled or pushed out of the syringe cavity through the plunger shaft cross-sectional opening creating a vacuum in the space located between the forward end of the piston head and the internal tapered wall surfaces of the syringe barrel. The plunger shaft remains in a withdrawn position until a force is applied along the longitudinal axis of the plunger shaft in a direction toward the forward end terminus of the plunger shaft to cause the plunger shaft to progressively pass through the plunger shaft cross-sectional opening formed in the contaminant shield and cause the plunger shaft and piston to advance along the longitudinal axis of the syringe barrel cavity toward the tapered internal wall surfaces and entrance/exit port of the syringe barrel. The inside diameter of the syringe barrel is equal to or slightly less than the diameter of the rim portion of the piston such that the piston rim slidably engages and maintains a tight seal with the internal wall surfaces of the syringe barrel cavity as the piston is advanced and withdrawn. This functions to maintain liquid medication or other fluid or material in the syringe barrel cavity forward of the piston head during advancement and withdrawal of the plunger and piston such that the medication or other liquid or materials in the syringe barrel cavity is ejected from the syringe cavity through the entrance/exit port or forward end opening as the plunger is advanced. As the plunger shaft and piston advance along the internal wall surfaces of the syringe barrel cavity, the semi-rigid flexible material or the flexible second part, depending on which contaminant shield design is used, contacts the surfaces of the plunger shaft while it is advanced through the plunger shaft cross-section of the contaminant shield providing a wiping and sweeping action to the surfaces of the plunger shaft in a direction away from the forward end terminus of the plunger shaft as the plunger shaft and piston are caused to traverse the syringe cavity toward the forward end terminus of the syringe barrel thereby aiding in preventing entry of contaminants into the syringe barrel cavity. The sweeping and wiping action functions to push contaminants such as dirt, dust, microorganisms, pyrogens, fibers, glass fragments, hair, foreign particles, etc., and pathogens, and any other type of contaminant carried by the air, hands, fingers, gloves, hair, clothing, etc, that is subsequently deposited onto the exposed portion of the plunger shaft, in a direction away from the forward end of the plunger shaft and ultimately from entering the syringe barrel cavity by way of the plunger shaft. The contaminant shield also functions to prevent deposition of dirt, lint, viral components, bacteria, germs, dust, microorganisms, pathogens, pyrogens, glass fragments, paper fibers, cloth fibers, hair, foreign particles, and any other type of contaminant carried by the air, hands, fingers, gloves, hair, clothing, etc., from falling into the rearward end opening of the syringe barrel and becoming deposited onto the internal surfaces of the syringe barrel cavity. The contaminant shield of the instant invention provides protection to the plunger shaft and the internal cavity wall surfaces of the syringe barrel in that contaminants deposited onto the outer surfaces of the contaminant cover, guard, or shield will not jeopardize the sterility of the inner cavity of the syringe barrel holding the medication or other fluid or materials because the contaminants cannot penetrate the walls of the contaminant guard or shield.

As an alternative to forming or molding the contaminant shield onto the inner wall surface of the syringe barrel, the contaminant shield can be formed separately from the syringe barrel and attached in a separate operation. For example, the contaminant shield could be formed with a wall extending perpendicularly from the forward face surface of the shield with the outer surface of the perpendicularly extending wall having grooves and/or threads formed thereon which mate with grooves and/or threads formed on the inner wall surfaces at the rearward end opening of the syringe barrel by screwing, turning, twisting, or rotating the threaded end cap contaminant shield into the grooved rearward end opening of the syringe barrel. Additionally, the shield portion of the end cap contaminant shield is formed with either the semi-rigid, flexible material or as the two-part material structure.

A further alternative includes providing a contaminant shield having walls extending perpendicularly from the forward face surface of the shield such that the outer surface of the perpendicularly extending walls have a flange or lip that mates with the inner wall surfaces of the syringe barrel at the rearward end opening through frictional fitting, snap fitting, locking, or a combination thereof. The extending walls can have a shape corresponding to the shape of the walls of the syringe barrel.

Still further, the end cap contaminant shield can be manufactured as a flat or plate design without extending walls and having only the forward and rearward end face surfaces comprising first and second parts and an opening in the shape of the plunger shaft cross section. The forward face surface of the end cap contaminant shield is attached by one or more of the methods of bonding by adhesives; ultrasonic bonding or welding; thermal bonding; etc., to the rearward end terminus of the syringe barrel. The plunger shaft functions and operates with the flat or plate end cap contaminant shield in the manner as previously described with the other end cap contaminant shield designs.

An advantage of using the shield is the protection provided by the shield to the internal cavity wall surfaces of the syringe in that contaminants deposited onto the rearward end wall surfaces of the shield will not jeopardize the sterility of the inner cavity of the syringe barrel because the contaminants are blocked by and cannot penetrate the shield.

An added function and benefit of the fifth embodiment is that the shield functions to prevent accidental separation of the plunger member from the syringe barrel by abutment of the forward face surface of the shield with forward end terminus of the plunger shaft or piston. Second, the shield functions as a temporary dam or barrier to fluids that may escape the syringe cavity due to piston failure.

When the end cap contaminant shield is used, the forward end terminus of the end cap walls function to prevent accidental separation of the plunger member and syringe barrel by abutment of the forward end terminus of the end cap perpendicularly extending walls with the forward end terminus of the plunger shaft or piston.

The syringes and the components forming the syringes of the instant embodiments can be formed by injection molding, blow molding, extrusion, compression molding, or any other molding process or combination of molding processes that will accomplish the molding objective of forming the syringe components, such that the molded syringe components mechanically operate together to perform the desired function and achieve the desired results. The components used to form the syringes of the instant invention as set forth above in the foregoing embodiments can be formed of plastic materials, polymers, rubber materials, metals, alloys, glass materials, ceramics, porcelain, fabrics, fiberglass, etc., or combinations thereof. The materials used to mold the syringe components will depend on the capacity in which the syringe will be used and the type of solution or fluid or other materials with which the syringe will be used. That is, some materials are more stable and safer to work with or store when in glass syringes; while syringes formed with other materials is sufficient for working with other solutions or fluids or other materials. The syringe barrels should be substantially transparent so the solutions or fluids or other materials in the barrel cavity can be monitored with regard to the volume measuring indicia formed and depicted on the syringe barrel. However, the syringes of the instant invention may also be tinted or colored to protect the material in the syringe from light exposure and prevent subsequent degradation.

The syringes of the instant invention can be used for prepacking medications, which will be used orally, for injection, for irrigations, for preparation of other solutions, etc. The syringes of the instant invention can also be used for manufacturing injectable or oral medications as pre-filled or pre-dosed syringes. The syringe can also be pre-filled with other materials including food products such as sauces, marinades, glazes, jellies, etc. The materials used to form the syringe components of the instant invention should be compatible with the ingredients of the pre-filled or pre-dosed medication, solution, other substances, etc., contained in the syringe during its storage so as to provide stability and a suitable shelf-life to the medication, solution, other substance, etc. Also, while shelved, the medications, solutions, other substances, etc., pre-filled and pre-dosed in the syringes of the instant invention should be protected in the syringes from adverse effects of moisture, atmospheric oxygen, and/or light, humidity, etc., when required.

In the case of single-dose, pre-dosed, or pre-filled syringes carrying an injectable, otic, nasal, ophthalmic, or oral medication, etc., a syringe of the instant invention can be manufactured, assembled, and filled with medication or other desired substance. The pre-filled syringe can be manufactured and assembled without a needle. A removable closure cap can be provided for the entrance/exit port at the reduced diameter neck. The user can remove the closure cap and attach a needle to the syringe when the medication or other materials is ready to use. Alternatively, the syringe of the instant invention can be manufactured and assembled with the needle as a unit wherein the needle or cannula can be permanently attached by one or more of the methods of molding; twisting, turning, rotating, or screwing onto threads located on external surface of the reduced diameter neck; fusing; adhesives; ultrasonic bonding or welding; thermal bonding; locking attachment; etc., to the reduced neck at the forward end of the syringe barrel. A removable needle cap or sheath is provided and can be attached by a tamper-resistant means such that the needle cap or sheath houses or covers the needle and ensures the integrity of the contents of the syringe prior to use and during storage. Alternatively, the needle or cannula with needle cap or sheath can be removably attached to the reduced neck at the forward end of the syringe barrel by screwing, frictional fit, etc. Also, a tamper-resistant means can be provided with the removably attached needle or cannula and needle cap or sheath. The medication pre-filled or pre-dosed in the syringe of the instant invention by the manufacturer, with or without a needle, is packaged for use. The medication, or other material, pre-filled or pre-dosed in the syringe of the instant invention by the manufacturer can be delivered to an individual as a single dose or as multiple doses. Because of the design of the syringes of the instant invention, the likelihood of contamination to the medications, solutions, fluids, or other materials, etc., of the pre-filled or pre-dosed syringes is reduced compared to existing syringe designs. That is, an added protective barrier is present protecting the pre-dosed or pre-filled medication in the syringe while shelved.

In order to maintain the plunger shaft in a withdrawn position and protect the pre-filled or pre-dosed medication, solution, or other substance, etc., from being inadvertently expelled or ejected from the syringe cavity due to impact or forces to the plunger shaft or other components of the syringe during shipping or storage, a brace means can be incorporated which functions to restrict the plunger shaft from traversing the syringe cavity. As an example, a brace means such as a shrink film or tape, tube, cage, etc., can be applied over the corrugated sheath, non-corrugated sheath, plunger member, syringe barrel, plunger shaft handle member, syringe barrel handle member, or combination thereof, in a manner to restrict longitudinal movement of the plunger shaft or plunger member until the brace means is removed. This functions to prevent advancement of the plunger shaft and piston along the syringe barrel cavity, which will eject the pre-filled or pre-dosed medication or other fluid or material from the syringe barrel. It also functions as a tamper resistant means. As an example, a cup-shaped tube or cage of appropriate height, length, diameter, etc., can be formed or molded, or manufactured, which fits over one or more of the withdrawn plunger shaft, plunger shaft handle member, plunger handle member, and any external corrugated or non-corrugated sheath. One or more shoulders can be provided at the rearward end opening of the syringe barrel or rear face surface of the syringe barrel handle member to provide a tamper resistant mating or locking surface with the open-end of the cup-shaped tube or cage for retaining the cage over one or more of the withdrawn or extended plunger shaft, plunger handle member, plunger shaft handle member, corrugated sheath, non-corrugated sheath, etc., during shipping and storage of the pre-dosed or pre-filled syringes to prevent the plunger shaft from being inadvertently advanced causing expulsion or ejection the material from the syringe barrel cavity. Alternatively, the shoulder and open-end of the cage can be threaded such that the tube or cage can be screwed, rotated, twisted, etc., onto the shoulder. A further alternative includes providing a pair of extending tabs positioned on opposite sides of the syringe barrel rearward end terminus. The extending tabs have holes therethrough, which are in face-to-face relationship with the plunger shaft. The body of the plunger shaft has successive holes formed therethrough along the longitudinal axis of the plunger shaft. Before or after the syringe is pre-filled with medication or other material, the holes formed in the tabs are aligned with one of the holes formed through the plunger shaft. A bar is then fed or inserted or molded through the aligned holes and locked in position protecting the medication or other material in the pre-filled syringe from inadvertent expulsion from the syringe. The bar prevents movement of the plunger shaft relative to the syringe barrel and maintains the pre-filled medication or other material from being ejected from the syringe barrel cavity.

The syringes of the instant invention can be used for pre-packing or prepackaging medications, or other materials, which will be delivered or taken orally by the individuals. The syringes of the instant invention can be used as containers for holding medications such as antibiotics, etc., which will later be given orally to a patient. The pre-packing or prepackaging of the oral unit dose syringes can be performed or accomplished by a manufacturer which can provide pre-dosed or pre-filled unit dose oral medication syringes containing a desired medication, or the syringes can be used by pharmacy or other personnel or individuals to pre-dose and package oral medications. Because of the design of the syringes of the instant invention, the likelihood of contamination to the medications of the pre-filled or pre-dosed syringes is reduced when compared with existing syringe designs. That is, the added protective barriers of corrugated and non-corrugated sheaths, end caps, shields, sealing rings, etc. are present and protecting the pre-filled or prepackaged or pre-dosed medication or other material in the syringe while shelved or refrigerated.

The syringes of the instant invention may also be provided with syringe caps, which fit or screw onto the reduced diameter neck portion of the forward end opening and function as closures. The syringe caps also function to preserve sterility of the outer surface of the reduced diameter neck and the inner cavity of the syringe barrel. The syringe cap may have any desired design. The syringe caps may also be tamper resistant.

The syringes of the instant invention can also be used advantageously by personnel working in labs, working with radioactive pharmaceuticals or radiopharmaceuticals, performing tests in hospital labs, doing research in pharmaceutical companies, universities, and any other type of research facility performing research in any capacity such as biological, pharmaceutical, genetic, etc., that require the use of syringes.

Trained personnel, such as those working in hospitals, compounding establishments, etc., can also use the syringes of the instant invention to pre-fill or pre-dose the syringes of the instant invention with injectable, topicals, otics, nasals, ophthalmics, or other materials, etc., or oral medications for delivery to a patient, nursing unit, doctor's office, other ordering establishment, etc.

Trained personnel can also use the syringes of the instant invention to prepare intravenous admixtures, withdraw blood from patients, inject intravenous medications into patients, inject intramuscular medications into patients, prepare irrigation solutions, prepare dialysis fluids, prepare intravenous pushes, prepare bolus fluids, prepare intravenous fluids for parenteral injection, prepare immunizations for any route of administration, prepare oral dose medications, etc.

Syringes of the instant invention can also be used in automated processes or operations in which machines are used to prepare syringes to be used in injectable, oral, intramuscular, intravenous, subcutaneous, intradermal, immunizations, dialysis, automatic dosing pumps, etc.

Also, syringes of the instant invention can be used for carrying and dispensing glues, adhesives, and other materials used in bonding operations, etc.

Syringes of the instant invention can also be used as carrying and dispensing means for food products such as cheeses, sauces, marinades, glazes, jellies, ketchup or catsup, mustard, mayonnaise, barbecue sauce, dips, toppings, icings, gravies, syrups, butters, honey, peanut butter, sandwich and cracker spreads, whipped creams, etc.

BRIEF DESCRIPTION OF THE DRAWINGS

Throughout the drawing figures, like reference numerals refer to like parts. The design features of the embodiments represented in the drawings are not intended to be restrictive to the inventive concept and other variations or modifications to the design features shown may be applied.

FIG. 1 is a cross-sectional view of a syringe of the instant invention having a corrugated sheath, cover, or shield concentrically enveloping a plunger shaft. The plunger is shown fully inserted into the syringe barrel cavity.

FIG. 2 is a view of the syringe of FIG. 1 with a greater length of the plunger member extending from the large rearward end opening of the syringe barrel while the corrugated sheath is shown in an elongated state maintaining the envelopment of the plunger shaft. The plunger and piston are shown displaced from their original positions having been moved down the syringe cavity.

FIG. 3 is a cross-sectional view of a second embodiment of the instant invention showing a syringe having a straight barrel segment and a corrugated barrel segment. The plunger is shown fully inserted into the syringe barrel cavity.

FIG. 4 is a view of the syringe of FIG. 3 with the corrugated segment in an elongated state enveloping the plunger shaft. The plunger and piston are shown displaced from their original positions having been moved down the syringe cavity.

FIG. 5 is a cross-sectional view of a third embodiment of the instant invention showing a syringe having mating concentric plunger and syringe barrel walls.

FIG. 6A is a view of the syringe of FIG. 5 with the plunger member displaced from its original position having been moved along the glide space that is located between the external wall surface of the syringe barrel and the internal wall surface of the plunger member. The piston and plunger shaft are shown displaced from their original positions having been moved down the syringe barrel cavity and away from the tapered internal walls of the syringe barrel cavity in cooperation with the plunger member displacement.

FIG. 6B is a view of FIG. 6A with sealing rings positioned on the syringe barrel and plunger member walls.

FIG. 7 is a cross-sectional view of a fourth embodiment of the instant invention showing a syringe having concentric syringe barrels and a mating plunger member. The plunger shaft and piston are shown fully inserted into the syringe barrel cavity.

FIG. 8A is a view of the syringe of FIG. 7 with the plunger member displaced from its original position having been moved along the glide space that is located between the external wall surface of the inner syringe barrel and the internal wall surface of the outer syringe barrel. The piston and plunger are shown displaced from their original positions having been moved down the inner syringe barrel cavity and away from the tapered internal walls of the inner syringe barrel cavity in cooperation with the plunger member displacement.

FIG. 8B is a view of FIG. 8A with sealing rings positioned on the concentric syringe barrel walls and the plunger member walls.

FIG. 10A is a view down the longitudinal axis of the syringe of FIG. 9 as viewed from the cross-section taken along 10—10 showing the semi-rigid, flexible material encircling the ribs of the plunger shaft.

FIG. 10B is a view down the longitudinal axis of the syringe of FIG. 9 as viewed from the cross-section taken along 10—10 showing the rigid or hard first part with the second part attached to its periphery or edge.

FIG. 11 is a view of a syringe barrel of the fifth embodiment depicting a dovetail groove formed in the inner wall of the syringe barrel cavity.

FIG. 12 is a view of a fifth embodiment of the instant invention wherein a syringe barrel section is formed with grooves at its rearward end for receiving the end cap contaminant shield walls having threads. A plunger shaft and piston are shown positioned within the syringe barrel cavity.

FIG. 13A is a cross-sectional view of an end cap contaminant shield of the fifth embodiment formed with a lip or flange for mating with a groove formed on the inner wall surface of the syringe barrel to lock the end cap within the rearward end opening of the syringe barrel.

FIG. 13B is a view of an end cap contaminant shield member of the fifth embodiment without the extending wall surface as shown in FIGS. 12 and 13A. The contaminant shield member is formed of a first part with an opening, the opening having the shape of the cross-section of the plunger member. A second part is molded to the periphery of the first part at the cross-sectional opening.

FIG. 14A is a cross-sectional view of a modification of the first embodiment of the instant invention showing a corrugated sheath, cover, or shield positioned on the inside of the syringe barrel enveloping a plunger shaft. The plunger shaft is shown fully inserted into the syringe barrel cavity.

FIG. 14B shows the syringe of FIG. 14A with the plunger shaft withdrawn and the corrugated sheath in a compressed state.

FIG. 15A is a cross-sectional view of a modification of the first embodiment of the instant invention showing a syringe having a non-corrugated sheath, cover, or shield enveloping the plunger shaft and positioned between the syringe barrel handle member and the plunger shaft handle member. The plunger shaft is fully inserted in the syringe barrel cavity and shows gathering or bunching of the non-corrugated sheath between the plunger shaft handle member and syringe barrel handle member.

FIG. 15B shows the syringe of FIG. 15A with the plunger shaft withdrawn and the non-corrugated sheath in a non-gathered or extended state between the plunger shaft handle member and the syringe barrel handle member.

FIG. 16A is a cross-sectional view of a modification of the first embodiment of the instant invention showing a syringe having a non-corrugated sheath, cover, or shield positioned on the inside of the syringe barrel enveloping a plunger shaft. The plunger shaft is shown fully inserted into the syringe barrel cavity FIG. 16B shows the syringe of FIG. 16A with the plunger shaft withdrawn and the non-corrugated sheath gathering or bunching along the plunger shaft between the rearward end opening of the syringe barrel and the forward end of the plunger shaft.

DETAILED DESCRIPTION OF THE INVENTION

Figure 9:
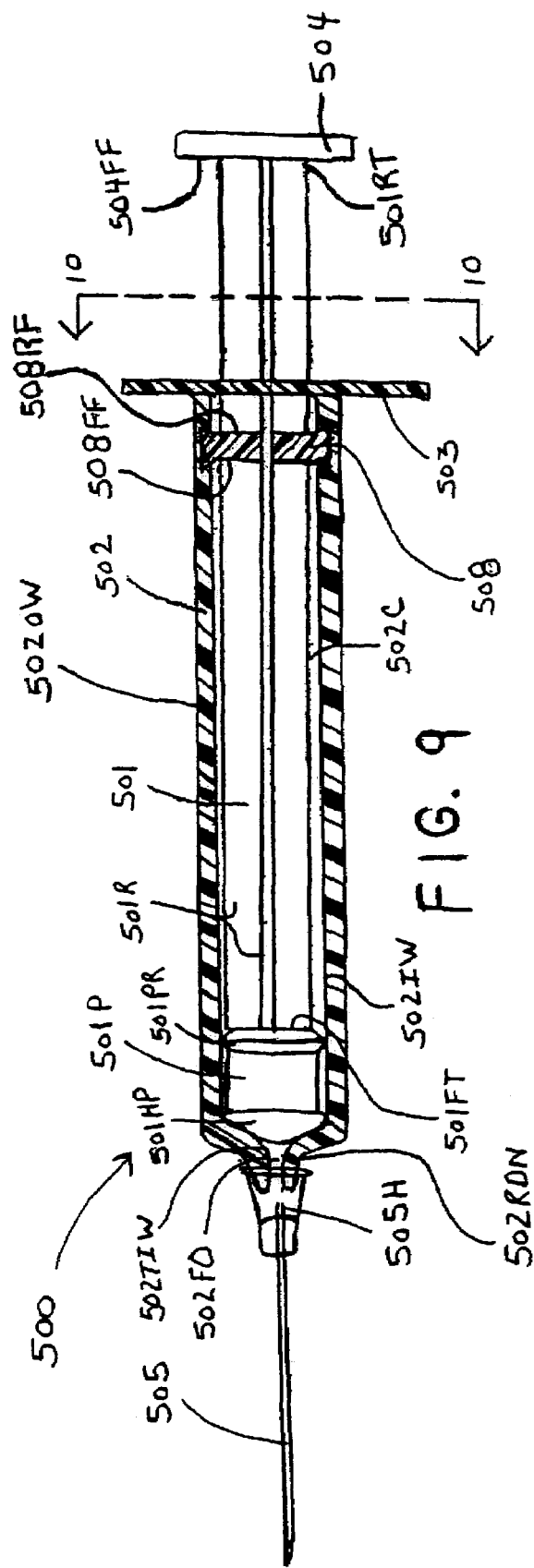
FIG. 9 is a longitudinal cross-sectional view of a fifth embodiment showing the contaminant shield molded in the syringe barrel cavity.

The following descriptions are presented to enable any person skilled in the art to make and use the invention, and are provided in the context of a particular application and its requirements. Various modifications to the disclosed embodiments will be readily apparent to those skilled in the art, and the general principles defined herein may be applied to other embodiments and applications without departing from the spirit and scope of the invention. The present invention is not intended to be limited to the embodiments described, but to be accorded the widest scope consistent with the principles and features disclosed herein.

For the purpose of describing how to use the syringes of each of the following embodiments, all of the embodiments will be described in accordance with the invention by making reference only to drawing liquid medication into the syringe and ejecting it out of the syringe. It is noted, however, that the syringes of the instant embodiments are compatible with performing other tasks requiring the use of a syringe, such as: withdrawing blood from patients, performing irrigations, injecting intravenous medications into patients, preparing and administering irrigation solutions, preparing and administering dialysis fluids, preparing intravenous pushes, preparing and administering bolus fluids, preparing and administering intravenous fluids for parenteral injection, drawing up oral medications for oral dispensing, prepacking or prefilling the syringe with medication or other fluids for oral or intravenous or intramuscular or subcutaneous uses, etc., for use in automated syringe filling processes; for use in preparing, holding, delivering or administering chemicals and glue materials or glue components or curing agents; for use as a dispensing means for food products, sauces, oils, butters, margarines, marinades, glazes, seasonings, gravies, etc.; preparing and administering dental solutions; preparing pre-filled syringes with medications for injection; preparing and administering sterile ophthalmics; preparing and administering otics, nasals; preparing large volume parenterals for intravenous injection; preparing and administering oral dose medications; preparing and administering chemotherapy medications; preparing and administering acids or bases; preparing and administering radioactive pharmaceuticals or radiopharmaceuticals; for use in preparing and delivering chemicals, glue materials; etc.

Syringe Having a Corrugated Sheath, Cover, or Shield

A new and improved syringe of the instant invention, as shown by FIG. 1, provides a syringe 100 formed of a cylindrical syringe barrel 101 and a cylindrical plunger shaft 103 having ribs. It is noted, however, that ribs are not required and the plunger shaft 103 can have any desired geometrical or other type of shape for its external surfaces or cross-section such as cylindrical, square, triangular, etc. The syringe barrel 101 has external wall surfaces 101EW, internal wall surfaces 101IW, and a syringe cavity 102 in which a plunger shaft 103 and a plunger piston 104P, attached to the forward end terminus of the plunger shaft 103, are positioned. The head 104HP of the plunger piston 104P is in contact with the tapered forward end internal walls 101TIW of the syringe barrel 101. The tapered forward end walls 101TIW of the syringe barrel 101 taper to form a reduced diameter neck 101RDN with a forward end opening 101FO at the forward end terminus of the syringe barrel 101. The tapered forward end external walls 101TEW of the reduced diameter neck 101RDN mate with the hub 105H of a needle 105 through frictional engagement. A circumferential wall can be formed around the external walls of the reduced diameter neck 101RDN. Threads or grooves are formed on the inside surfaces of the encircling circumferential wall such that the hub 105H of the needle 105 can be rotated or twisted on the threads or grooves and locked onto the tapered external wall surfaces 101TEW of the reduced diameter neck 101RDN and within the circumferential wall. Alternatively, threads or grooves can be formed on the tapered external wall surfaces 101TEW and on the inner wall surfaces of the hub 105H. The rearward end terminus 101RT of the walls 101W of the syringe barrel 101 is molded to the forward face surface 106FF of an annular syringe barrel handle member 106. The syringe barrel handle member 106 can alternatively be formed continuously with the syringe barrel walls 101W during the syringe barrel molding process. Molded to at least one of the surfaces of the syringe barrel handle member 106, at the rearward end terminus 107RT of the syringe barrel 101, is a forward end terminus 107FT of a corrugated sheath 107. Such surfaces include, but are not limited to, the rearward face surface 106RF, the forward face surface 106FF, or the side surfaces 106SS. The rearward end terminus surface 107RT of the corrugated sheath 107 is molded to at least one of the surfaces of the plunger handle member 108. Such surfaces include but are not limited to, the rearward face surface 108RF, the forward face surface 108FF, or the side surfaces 108SS. The corrugated sheath, cover, or shield 107 concentrically envelops the rearward end portion of the plunger shaft 103RP when the plunger shaft 103 and piston 104P are fully inserted into the syringe barrel, as shown in FIG. 1. The forward end terminus 107FT of the corrugated sheath, cover, or shield 107 is attached by one or more of the methods of molding, fusing, adhesives, ultrasonic bonding or welding, thermal bonding, etc., to at least one of the surfaces of the syringe barrel handle member 106. The syringe barrel handle member 106 is formed or molded on the rearward end terminus 101RT of the walls 10W of the syringe barrel 101. The rearward end terminus 107RT of the corrugated sheath, cover, or shield 107 is attached by one or more of the attachment methods of molding, fusing, adhesives, ultrasonic bonding or welding, thermal bonding, etc., to at least one surface of the plunger handle member 108 which is molded, or formed, on the rearward end terminus 103RT of the plunger shaft 103. The rearward end terminus 103RT of the plunger shaft 103 is centrally molded and normal to the forward face surface 108FF of the plunger handle member 108. The forward end of the body of the plunger shaft 103 extends into the syringe cavity or hollow portion 102 of the syringe barrel 101. The corrugated sheath, cover, or shield 107 encloses and surrounds the rearward end portion 103RP of the plunger shaft 103 along the longitudinal axis of the portion of the plunger shaft 103 extending between the syringe barrel handle member 106 and the plunger handle member 108. The sheath 107 houses, encloses, or surrounds the portion of the plunger shaft 103 within the central cavity or hollow 107C of the corrugated sheath 107 when the corrugated sheath 107 is in a compressed state and in a lengthened state. The plunger shaft 103 can be manually withdrawn from the syringe barrel cavity or hollow 102 by grasping the external walls of the syringe barrel 101EW with one hand and the plunger shaft handle member 108 and/or the outer surface of the corrugated sheath 107EW with the other hand and pulling the plunger shaft handle member 108 and/or corrugated sheath 107 such that the longitudinal length of the plunger shaft 103 traverses the cavity or hollow 102 of the syringe barrel 101 and progressively emerges from the rearward end opening 101RO of the syringe barrel 101. The peaks 107P and walls 107W of the pleats, corrugations, or folds in the sheath 107 are caused to separate along the longitudinal axis of the sheath 107 thereby lengthening the sheath 107 along its longitudinal axis. The plunger shaft 103 remains centrally located within the hollow or cavity 107C of the corrugated sheath 107 as the plunger shaft 103 emerges from the cavity 102 and rearward end opening 101RO of the syringe barrel 101. As the corrugations or folds separate, the corrugated sheath 107 lengthens enabling the plunger shaft 103 to be withdrawn from the hollow or cavity 102 of the syringe barrel 101, as depicted in FIG. 2. The corrugated sheath 107 lengthens and encloses a greater length of the plunger shaft 103 as the plunger shaft 103 is further withdrawn from the syringe barrel hollow 102. As the plunger shaft 103 is withdrawn from the syringe barrel hollow 102, a space 101S is formed between the piston head 104HP of the plunger piston 104P and the tapered internal walls 101TIW of the syringe barrel 101. The sheath 107 remains in the lengthened or elongated position until a force is used to compress or collapse the walls 107W of the folds or corrugations of the sheath 107 together. That is, it is not necessary for an individual, or machinery when used to manipulate the syringe in an automation process, to hold the withdrawn plunger 103 or lengthened corrugated sheath 107 such that it remains in its withdrawn and lengthened state. The corrugated sheath 107 is designed and manufactured such that it does not automatically recoil to its compressed or shortened state after being elongated or to its elongated state after being compressed. A force must be applied along the longitudinal axis of the syringe to cause the ends of the elongated corrugated walls 107W to be moved toward each other such that the corrugated sheath 107 compresses and shortens. When the walls 107W of the corrugated sheath 107 are forced together, the sheath 107 shortens. Shortening of the corrugated sheath 107 can be performed by applying pressure to the rearward end face surface 108RF of the plunger handle member 108 or along the corrugated sheath 107 in the direction toward the rearward end opening 101RO of the syringe barrel 101 to cause the sheath 107 to shorten and the plunger shaft 103 and the piston 104P to traverse the syringe barrel cavity 102 toward the tapered internal wall 101TIW surfaces of the syringe cavity 102 and the syringe entrance/exit port 101EP such that the medication or other materials can be ejected from the syringe barrel cavity 102 through the entrance/exit port 101EP. The piston rim 104PR slidably engages and maintains a tight seal with the internal wall surfaces 101IW of the syringe barrel cavity 102 as the piston 104P advances. The diameter of the syringe barrel cavity 102 is equal to or slightly less than the diameter of the piston rim 104PR. Liquid medication or other material in the cavity 102 remains forward of the piston head 104IP during advancement and withdrawal of the plunger 103 and piston 104P such that the medication or other material in the syringe barrel cavity 102 is ejected from the syringe cavity 102 through the entrance/exit port 101EP. An advantage of using the corrugated sheath 107 is the protection provided by the sheath 107 to the plunger shaft 103 and the internal cavity wall surfaces 101IW of the syringe barrel 101 in that contaminants deposited onto the external wall surface 107EW of the corrugated sheath 107 or the external wall surface 101EW of the syringe barrel 101 will not jeopardize the sterility of the inner cavity 102 of the syringe barrel 101 because the contaminants cannot penetrate the walls of the corrugated sheath 107 or the syringe barrel 101. It is also noted that the peaks, pleats, valleys, and walls of the corrugations can have any desired shape such as curved, triangular, square, apexed, etc, so long as the desired mechanical functioning of the corrugated sheath 107 as set forth above is not compromised.

In operation, medication or other material is drawn up from a vial or ampoule, ampul, ampule, for example, by first introducing the needle 105, which is attached to the reduced diameter neck 101RDN of the entrance/exit port 101EP, into the vial or ampoule, ampul, ampule, containing the medication or other material. Next, the corrugations or folds of the corrugated sheath 107 are caused to separate by pulling the plunger handle member 108. This also causes the plunger shaft 103 and piston 104P to traverse the syringe barrel cavity 102 away from the tapered internal walls 101TIW of the syringe barrel cavity 102 and toward the rearward end opening 101RO. As the plunger piston 104P traverses the syringe barrel cavity 102, the piston rim 104PR slidably engages and maintains a tight seal with the internal wall surfaces 101IW of the syringe barrel cavity 102. This causes the air column in the syringe bore or cavity 102 located behind the plunger piston 104P and adjacent the body of the plunger shaft 103 to be pushed out of the syringe barrel 101. A vacuum is created in the space located between the forward end of the piston head 104HP and the tapered internal wall surface 101TIW of the syringe barrel 101 as the piston head 104HP is pulled away from the tapered internal walls 101TIW. The vacuum created causes the liquid medication or other material in the vial, or ampul, ampoule, ampule to be drawn into the syringe barrel cavity 102 through the needle 105, which is frictionally attached to the outer walls of the reduced diameter neck 101RDN, and the entrance/exit port 101EP. The needle 105 is then removed from the vial, or ampul, ampoule, ampule of medication or other material and positioned in the needle port of an appropriate bag or bottle of intravenous solution. The liquid medication is then injected into the bag or bottle of intravenous solution. The reduced diameter neck 101RDN can be manufactured or molded to operate with any existing line of hypodermic needles, tubing, caps, closures, etc.

Also, the peaks, pleats, valleys, and walls of the corrugated sheaths may have any desired thickness depending on the desired or needed flexibility for the sheath. The formed sheaths may be rigid to flexible.

An alternative to this embodiment, as shown by FIGS. 14A and 14B, provides a syringe 700 formed of a syringe barrel 701, a plunger shaft 703, a piston 704P, and a corrugated sheath 707 that is positioned within the syringe barrel cavity 701C. It is noted that the syringe barrel 701, corrugated sheath 707, plunger shaft 703, plunger piston 704P, handle members 706 and 708, and other components of the syringe 700 can have any desired shape or cross-section such as cylindrical, square, triangular, etc. The plunger shaft 703 may also be formed with ribs or fins, if desired or warranted. The syringe barrel 701 has external wall surfaces 701EW, internal wall surfaces 701IW, and a syringe cavity 701C in which a plunger shaft 703 and a plunger piston 704P, attached to the forward end terminus 703FT of the plunger shaft 703, are positioned. The head 704HP of the plunger piston 704P is in contact with the tapered forward end internal walls 701TIW of the syringe barrel 701. The tapered forward end walls 701TW of the syringe barrel 701 form a reduced diameter neck 701RDN with a forward end opening 701FO at the forward end terminus of the syringe barrel 701. The reduced diameter neck 701RDN mates with the hub 705H of a needle 705, through frictional engagement. As an alternative, a circumferential wall can be formed around the external walls of the reduced diameter neck 701RDN. Threads or grooves are formed on the inside surfaces of the encircling circumferential wall such that the hub 705H of the needle 705 can be rotated or twisted on the threads or grooves and locked onto the reduced diameter neck 701RDN and within the circumferential wall. Alternatively, threads or grooves can be formed on the reduced diameter neck 701RDN and on the inner wall surfaces of the hub 705H such that the hub 705H can be directly turned, rotated, twisted, or screwed onto the reduced diameter neck 701RDN. The rearward end terminus 701RT of the walls 701W of the syringe barrel 701 is molded to the forward face surface 706FF of an annular syringe barrel handle member 706, or the syringe barrel handle member 706 can be molded or formed continuously with the syringe barrel walls 701W during the syringe barrel molding process. The corrugated sheath 707 is housed within the syringe barrel cavity 701C. The rearward end terminus 707RT of the corrugated sheath, cover, or shield 707 is attached at or near the rearward end terminus opening 701RO of the syringe barrel 701. The forward end terminus 707FT of the corrugated sheath, cover, or shield 707 is attached or molded to the forward end terminus of the plunger shaft 703FT or attached or molded at a different position located along the longitudinal length of the plunger shaft 703. This design seals the internal walls of the syringe barrel from exposure to the external environment and eliminates entry of contaminants into the syringe barrel cavity, by way of the rearward end opening. The corrugated sheath, cover, or shield 707 envelops and/or houses the portion of the plunger shaft 703 located between the point of attachment of the forward end terminus 707FT of the corrugated sheath 707 and the point of attachment of the rearward end terminus 707RT of the corrugated sheath 707.

The rearward end terminus 707RT of the corrugated sheath 707 is formed with a shape, cross-section, radius, or diameter such that its rearward end terminus 707RT edges substantially align with the attachment surfaces of the syringe barrel at or near the rearward end terminus opening 701RO of the syringe barrel 701. The forward end terminus 707FT of the corrugated sheath 707 is formed with a shape, cross-section, radius, or diameter, such that its forward end terminus 707FT edges substantially align with the attachment surfaces of the plunger shaft 703 at or near the forward end terminus of the plunger shaft 703FT.

As the corrugated sheath 707 is elongated or lengthened by advancing the plunger shaft 703 into and along the syringe barrel cavity 701C, the corrugated sheath 707 and walls of the syringe barrel 701W envelope a greater length of the plunger shaft 703, as shown in FIG. 14A. As the corrugated sheath is compressed, or shortened by withdrawing the plunger shaft 703 from the syringe barrel cavity 701C, a shorter length of the plunger shaft 703 is enveloped by the corrugated sheath 707 and walls 701W of the syringe barrel 701, as shown in FIG. 14B. The forward end terminus 707FT of the corrugated sheath, cover, or shield 707 is attached to the forward end terminus of the plunger shaft 703FT or at a position along its longitudinal length by one or more of the methods of molding, fusing, adhesives, ultrasonic bonding or welding, thermal bonding, etc. The forward end terminus 707FT of the corrugated sheath 707 is formed with a shape, cross-section, radius, or diameter, such that its forward end terminus 707FT edges substantially align with the attachment surfaces of the plunger shaft 703 at or near the forward end terminus of the plunger shaft 703FT. The rearward end terminus 707RT of the corrugated sheath, cover, or shield 707 is attached at or near the rearward end terminus opening 701RO of the syringe barrel 701 by one or more of the methods of molding, fusing, adhesives, ultrasonic bonding or welding, thermal bonding, etc The rearward end terminus 703RT of the plunger shaft 703 is molded and normal to the forward face surface 708FF of the plunger handle member 708. The forward end of the body of the plunger shaft 703 extends into the syringe barrel cavity or hollow 701C. The corrugated sheath, cover, or shield 707 encloses and surrounds the portion of the plunger shaft 703 extending between the point of attachment of the rearward end terminus 707RT of the corrugated sheath 707 at or near the syringe barrel rearward end opening 701RO and the point of attachment of the forward end terminus 707FT of the corrugated sheath 707 with the plunger shaft 703. As the plunger shaft 703 is withdrawn from the syringe barrel cavity 701C, the forward end terminus of the plunger shaft 703FT approaches the rearward end opening 701RO of the syringe barrel 701 causing compression of the corrugated sheath 707 along its longitudinal axis. As a result, the compressed corrugated sheath 707 houses, encloses, or surrounds less of the plunger shaft 703 as the plunger shaft 703 is withdrawn from the syringe barrel cavity 701C. The corrugated sheath 707 remains housed within the syringe barrel 701 during use and operation of the syringe 700.

When manually manipulating the syringe 700, the plunger shaft 703 can be withdrawn from the syringe barrel cavity or hollow 701C by grasping the external walls of the syringe barrel 701EW with one hand and the plunger shaft 703 and/or plunger shaft handle member 708 with the other hand and pulling the plunger shaft 703 such that the longitudinal length of the plunger shaft 703 traverses the cavity or hollow 701C of the syringe barrel 701 and progressively emerges from the rearward end opening 701RO of the syringe barrel cavity 701C. The above manual operation can also be performed with one hand. It is noted here that the above manual operation can alternatively be performed by machinery, such as syringe filling automated processes, and that touching of the plunger shaft 703 with the hands, machinery, or other objects will not compromise the sterility of the inner walls of the syringe barrel 701IW because the corrugated sheath 707 functions to impede entry of contaminants by forming a barrier. As the plunger shaft 703 is withdrawn from the syringe barrel cavity 701C, the walls 707W of the pleats, corrugations, or folds in the corrugated sheath 707, surrounding the plunger shaft 703, become closer and are caused to compress along the longitudinal axis of the corrugated sheath 707 thereby shortening the corrugated sheath 707 along its longitudinal axis in a direction toward the rearward end opening 701RO of the syringe barrel 701. The length of the plunger shaft 703 enveloped or housed within the hollow or cavity 707C of the corrugated sheath 707 decreases as the plunger shaft 703 emerges from the syringe barrel cavity 701C and rearward end opening 701RO of the syringe barrel 701. As the corrugations or folds of the corrugated sheath 707 within the syringe barrel cavity 701C compress, the corrugated sheath 707 shortens within the syringe barrel cavity 701C enabling the plunger shaft 703 to be withdrawn from the hollow or cavity 701C of the syringe barrel 701, as depicted in FIG. 14B. The corrugated sheath 707 shortens and encloses or envelopes less of the plunger shaft 703 as the plunger shaft 703 is withdrawn from the syringe barrel hollow 701C. As the plunger shaft 703 is withdrawn from the syringe barrel hollow 701C, a space 701S is formed between the piston head 704HP of the plunger piston 704P and the tapered internal walls 701TIW of the syringe barrel 701. It is not necessary for an individual, or machinery when used to manipulate the syringe, to hold the withdrawn plunger shaft 703 or plunger handle member 708 to ensure that the corrugated sheath 707 remains in its compressed state. The corrugated sheath 707 is designed and manufactured such that it does not automatically recoil or recover to its lengthened state after being compressed or recoil to its compressed state after being lengthened. A force must be applied along the longitudinal axis of the plunger shaft 703 and/or corrugated sheath 707 to cause the adjacent compressed walls 707W of the corrugated sheath 707 to be moved away from each other such that the corrugated sheath 707 lengthens or elongates within the syringe barrel cavity 701C. That is, the corrugated sheath 707 remains in the compressed state until a force is applied in a direction along the longitudinal axis of the plunger shaft 703 to cause the plunger shaft 703 to advance into the syringe barrel cavity 701C and cause separation of the walls 707W of the folds or corrugations of the compressed corrugated sheath 707. When the walls 707W of the corrugated sheath 707 are caused to separate, the corrugated sheath 707 lengthens. Lengthening of the corrugated sheath 707 can be performed by applying pressure to the rearward end face surface 708RF of the plunger handle member 708 or by applying a force in a direction along the longitudinal axis of the plunger shaft 703 to advance the plunger shaft 703 and piston 704P in the direction toward the forward end opening 701FO and tapered internal walls 701TIW of the syringe barrel cavity 701C thereby causing the corrugated sheath 707 to lengthen or elongate. The corrugated sheath 707 is manufactured such that it does not impede traversal of the plunger shaft 703 and piston 704P along the syringe barrel cavity 701C. The piston rim 704PR slidably engages and maintains a tight seal with the internal wall surfaces 701IW of the syringe barrel cavity 701C as the piston 704P traverses the syringe barrel cavity 701C. Medication or other types of materials drawn into the syringe barrel cavity 701C remain forward of the piston head 704HP during withdrawal and advancement of the plunger shaft 703 and piston 704P such that the medication or other types of materials drawn into the syringe barrel cavity 701C can be ejected from the syringe barrel cavity 701C through the entrance/exit port 701EP. The external wall surfaces of the corrugated sheath 707EW are exposed to the external environment and form a face-to-face relationship with the plunger shaft 703, while the internal wall surface 7071W of the corrugated sheath 707 is not exposed to the external environment and forms a face-to-face relationship with the internal wall surfaces 701IW of the syringe barrel cavity 701C. An advantage of using the corrugated sheath 707 within the syringe barrel cavity 701C is the protection provided by the sheath 707 to the internal cavity wall surfaces 701IW of the syringe barrel cavity 701C in that contaminants deposited onto the external wall surface 707EW of the corrugated sheath 707, and/or external wall surfaces 701EW of the syringe barrel 701, and/or the surfaces of the plunger shaft 703 will not jeopardize the sterility of the inner cavity 701C of the syringe barrel 701 because the contaminants cannot penetrate the walls of the corrugated sheath 707, syringe barrel 701, or plunger shaft 703. For this embodiment, the external wall surfaces 707EW of the corrugated sheath 707 are exposed to the external environment by way of the rearward end opening 701RO of the syringe barrel 701. Also, the syringe design inhibits separation of the plunger shaft 703 from the rearward end opening 701RO of the syringe barrel 701. The syringe design also functions as a dam or barrier to collect or accumulate drawn-up medications, or other types of materials being used, that leak from the syringe cavity and piston due to piston failure. In operation, medication or other material is drawn up from a vial or ampoule, ampul, ampule, for example, by first introducing the needle 705, which is attached to the reduced diameter neck 701RDN of the entrance/exit port 701EP, into the vial or ampoule, ampul, ampoule, containing the medication or other material. Next, the corrugations or folds of the corrugated sheath 707 are caused to compress by pulling the plunger handle member 708. This also causes the plunger shaft 703 and piston 704P to traverse the syringe barrel cavity 701C away from the tapered internal walls 701TIW of the syringe barrel cavity 701C and toward the rearward end opening 701RO. As the plunger piston 704P traverses the syringe barrel cavity 701C, the piston rim 704PR slidably engages and maintains a tight seal with the internal wall surfaces 701IW of the syringe barrel cavity 701C. A vacuum is created in the space located between the forward end of the piston head 704HP and the tapered internal wall surface 701TIW of the syringe barrel 701 as the piston head 704HP is pulled away from the tapered internal walls 701TIW. The vacuum created causes the liquid medication or other material in the vial, or ampul, ampoule, ampule to be drawn into the syringe barrel cavity 701C through the needle 705, which is frictionally attached by a hub 705H to the outer walls of the reduced diameter neck 701RDN, and the entrance/exit port 701EP. The needle 705 is then removed from the vial, or ampul, ampoule, ampule of medication or other material and positioned in the needle port of an appropriate bag or bottle of intravenous solution. The liquid medication is then injected into the bag or bottle of intravenous solution. The reduced diameter neck 701RDN can be manufactured or molded to operate with any existing line of hypodermic needles, tubing, caps, closures, etc.

It is also noted that the peaks, pleats, valleys, and walls 707W of the corrugations can have any desired shape, curvature, and cross-section—such as curved, triangular, square, etc, so long as the desired mechanical functioning of the corrugated sheath 707 as set forth above is not compromised. The corrugated sheath 707 may be tapered from one end to the other end such that each successive neighboring corrugated peaks 707P along the corrugated sheath 707 has a smaller diameter than the previous corrugated peak 707P. The taper can run from the forward or rearward end of the corrugated sheath 707 to its opposite end. Alternatively, the taper can run from the central or middle of the corrugated sheath 707 simultaneously toward both the forward and rearward ends of the corrugated sheath 707. Alternatively, the diameters of each successive peak of the corrugated sheath 707 may be substantially identical. Also, the peaks, pleats, valleys, and walls of the corrugated sheaths 707 may have any desired thickness depending on the desired, needed, or required flexibility of the sheath. The formed corrugated sheaths may be rigid to flexible.

Syringe Having a Non-Corrugated Sheath, Cover, or Shield

A modification to the corrugated sheath embodiment provides a syringe 800 having a non-corrugated flexible, tubular-shaped film or lamina sheath 807 of one or more layers, as shown in FIGS. 15A and 15B. The rearward end of the non-corrugated tubular film or lamina sheath 807 is molded or attached to the plunger shaft handle member 808 and the forward end 807FT of the non-corrugated sheath 807 is molded or attached to the annular syringe barrel handle member 806 in the same manner as previously described for the corrugated sheath. The non-corrugated tubular film or lamina sheath 807 can have any desired shape, cross-section, curvature—such as cylindrical, square, triangular, etc. The film or lamina can be formed from any desired material or materials so long as the selected materials do not hinder the mechanical functioning of the syringe components. The non-corrugated tubular film 807 functions as a sheath, cover, or shield to prevent the entry of contaminants into the syringe barrel cavity 801C by way of the syringe barrel rearward end opening 801RO. The forward end terminus 807FT of the non-corrugated sheath 807 can be attached to at least one surface of the syringe barrel handle member 806 at the syringe barrel rearward end terminus opening 801RO. Such surfaces include, but are not limited to, the rearward end face surface 806RF, forward end face surface 806FF, or side surface 806SS of the syringe barrel handle member 806. The non-corrugated sheath 807 is attached to the syringe barrel handle member 806 by one or more of the attachment methods of molding, fusing, adhesives, ultrasonic bonding or welding, thermal bonding, etc. The annular syringe barrel handle member 806 is attached in a separate step to the rearward end terminus of the syringe barrel 801RT by one or more of the attachment methods of molding, fusing, adhesives, ultrasonic bonding or welding, thermal bonding, etc. or is molded continuous as a single unit with the syringe barrel walls 801W during the forming and molding process. The rearward end terminus 807RT of the non-corrugated sheath 807 is attached to at least one surface of the plunger shaft handle member 808. Such surfaces include, but are not limited to, the forward end face surface 808FF, rearward end face surface 808RF, or side surface 808SS of the plunger shaft handle member 808. The non-corrugated sheath 807 is attached to the plunger handle member 808 by one or more of the attachment methods of molding, fusing, adhesives, ultrasonic bonding or welding, thermal bonding, etc. Thus, the plunger shaft 803 and rearward end syringe barrel opening 801RO are sealed from, and not exposed to, the outside environment. Alternatively, the non-corrugated sheath 807 can be attached to the plunger shaft 803 at or near the plunger shaft handle member 808. The forward face surface 808FF of the plunger shaft handle member 808 is centrally attached to the rearward end terminus 803RT of the plunger shaft 803 by one or more of the attachment methods of molding, fusing, adhesives, ultrasonic bonding or welding, thermal bonding, etc. or is molded continuous as a single unit with the plunger shaft 803 during the forming process. The non-corrugated sheath 807 encloses and surrounds that portion of the longitudinal axis of the plunger shaft 803 extending from the syringe barrel rearward end opening 801RO. As the plunger shaft 803 and piston 804P are advanced further into the syringe barrel cavity 801C toward the tapered internal walls 801TIW of the syringe barrel cavity 801C, the plunger shaft handle member 808 advances toward the syringe barrel handle member 806 resulting in a shorter length of the plunger shaft 803 extending from the rearward end opening 801RO of the syringe barrel 801, causing the non-corrugated sheath 807 to bunch, gather, accumulate, or collect between the syringe barrel handle member 806 and the plunger shaft handle member 808 while enclosing and surrounding the length or segment of the plunger shaft 803 extending from the rearward end opening 801RO of the syringe barrel 801, as shown in FIG. 15A.

Lengthening of the non-corrugated sheath 807 is performed by withdrawing the plunger shaft 803 from the syringe barrel cavity 801C such that the plunger shaft 803 and the piston 804P traverse the syringe barrel cavity 801C away from the tapered internal wall 801TIW surfaces of the syringe barrel cavity 801C. As the plunger shaft 803 is withdrawn from the syringe barrel cavity 801C, the plunger shaft handle member 808 moves away from the syringe barrel handle member 806 and more of the plunger shaft 803 exits the rearward end opening 801RO of the syringe barrel 801 causing a longer length of plunger shaft 803 to extend from the rearward end opening 801RO of the syringe barrel cavity 801C. As the plunger shaft 803 exits the syringe barrel cavity 801C, the bunched or gathered non-corrugated sheath 807 lengthens or elongates to enclose and surround a longer portion or more of the plunger shaft 803 extending from the rearward end opening 801RO of the syringe barrel cavity 801C, as shown in FIG. 151B. The length of the plunger shaft 803 enveloped or housed within the hollow or cavity 807C of the non-corrugated sheath 807 increases as more of the plunger shaft 803 continues to emerge from the rearward end opening 801RO of the syringe barrel 801 because the plunger shaft handle member 808 and syringe barrel handle member 806 progressively separate. The non-corrugated sheath 807 lengthens and longitudinally encloses or envelopes a greater or longer length of the plunger shaft 803 as the plunger shaft 803 is further withdrawn from the syringe barrel hollow 801C. As the plunger shaft 803 is withdrawn from the syringe barrel hollow 801C, a space 801S is formed between the piston head 804HP of the plunger piston 804P and the tapered internal walls 801TIW of the syringe barrel 801. The non-corrugated sheath 807 lengthens and remains in the elongated or lengthened state until a force is applied along the longitudinal axis of the plunger shaft 803 to cause the plunger shaft 803 and piston 804P to advance into the syringe barrel cavity 801C in a direction toward the tapered walls 801TW of the syringe barrel 801. It is not necessary for an individual, or machinery when used to manipulate the syringe components, to hold the withdrawn plunger shaft 803 such that the non-corrugated sheath 807 remains in its lengthened or elongated state. The non-corrugated sheath 807 is designed and manufactured such that it does not automatically recoil or recover to its bunched or gathered state after being elongated and does not automatically recoil or recover to its elongated state after being bunched or gathered. A force must be applied along the longitudinal axis of the plunger shaft 803 to cause the non-corrugated sheath 807 to shorten by gathering, bunching, or accumulating the non-corrugated sheath material.

The non-corrugated sheath 807 is manufactured such that it does impede traversal of the plunger shaft 803 and piston 804P along the syringe barrel cavity 801C. When manipulating the plunger, the piston rim 804PR slidably engages and maintains a tight seal with the internal wall surfaces 801IW of the syringe barrel cavity 801C as the piston 804P traverses the syringe barrel cavity 801C. Medication or other types of materials drawn into the syringe barrel cavity 801C remain forward of the piston head 804HP during withdrawal and advancement of the plunger shaft 803 and piston 804P such that the medication or other types of materials drawn into the syringe barrel cavity 801C can be ejected from the syringe barrel cavity 801C through the entrance/exit port 801EP/801FO. In order to eject medication and other types of materials from the syringe barrel cavity 801C, pressure can be applied to the rearward end face surface 808RF of the plunger shaft handle member 808 or along the plunger shaft 803 to advance the plunger shaft 803 and piston 804P in the direction toward the tapered internal wall 801TIW surfaces of the syringe barrel cavity 801C. As the plunger shaft 803 and piston 804P advance along the syringe barrel cavity 801C, the lengthened or elongated non-corrugated sheath 807 gathers or accumulates. The non-corrugated sheath 807 functions to protect the plunger shaft 803 and the internal cavity wall surfaces 801IW from contaminants deposited onto the external wall surfaces 807EW of the non-corrugated sheath 807 and syringe barrel 801. The tapered forward end walls 801TW of the syringe barrel 801 form a reduced diameter neck 801RDN with a forward end opening 801FO/entrance-exit port 801EP at the forward end terminus of the syringe barrel 801. The reduced diameter neck 801RDN mates with the hub 805H of needle 805 through frictional engagement. As an alternative, a circumferential wall can be formed around the external walls of the reduced diameter neck 801RDN. Threads or grooves are formed on the inside surfaces of the encircling circumferential wall such that the hub 805H of the needle 805 can be rotated or twisted on the threads or grooves and locked onto the outer walls of the reduced diameter neck 801RDN and within the circumferential wall. Alternatively, threads or grooves can be formed on the reduced diameter neck 801RDN and on the inner wall surfaces of the hub 805H such that the hub 805H can be directly rotated or twisted onto the reduced diameter neck 801RDN. In operation, medication or other material is drawn up from a vial or ampoule, ampul, ampule, for example, by first introducing the needle 805, which is attached to the reduced diameter neck 801RDN of the entrance/exit port 801EP, into the vial or ampoule, ampul, ampule, containing the medication or other material. Next, the non-corrugated sheath 807 is caused to ungather or lengthen by pulling the plunger handle member 808. This also causes the plunger shaft 803 and piston 804P to traverse the syringe barrel cavity 801C away from the tapered internal walls 801TIW of the syringe barrel cavity 801C and toward the rearward end opening 801RO. As the plunger piston 804P traverses the syringe barrel cavity 801C, the piston rim 804PR slidably engages and maintains a tight seal with the internal wall surfaces 801IW of the syringe barrel cavity 801C. A vacuum is created in the space located between the forward end of the piston head 804HP and the tapered internal wall surface 801TIW of the syringe barrel 801 as the piston head 804HP is pulled away from the tapered internal walls 801TIW. The vacuum created causes the liquid medication or other material in the vial, or ampul, ampoule, ampule to be drawn into the syringe barrel cavity 801C through the needle 805, which is frictionally attached by a hub 805H to the outer walls of the reduced diameter neck 801RDN, and the entrance/exit port 801EP. The needle 805 is then removed from the vial, or ampul, ampoule, ampule of medication or other material and positioned in the needle port of an appropriate bag or bottle of intravenous solution. The liquid medication is then injected into the bag or bottle of intravenous solution. The reduced diameter neck 801RDN can be manufactured or molded to operate with any existing line of hypodermic needles, tubing, caps, closures, etc.

A further modification is using the non-corrugated sheath 907, as shown in FIGS. 16A and 16B. The forward end terminus 907FT of the non-corrugated sheath 907 is attached at or near the forward end terminus 903FT of the plunger shaft 903, and the rearward end terminus 907RT of the non-corrugated sheath 907 is attached at or near the rearward end terminus 901RT of the syringe barrel 901. This syringe design provides a non-corrugated sheath, cover, or shield 907 positioned and housed within the syringe barrel cavity or hollow 901C. The non-corrugated sheath 907 forms a separating barrier within the syringe barrel cavity 901C between the external and internal environments. The external wall surface of the non-corrugated tubular sheath 907EW is exposed to the external environment and forms a face-to-face relationship with the plunger shaft 903, while the internal wall surface 907IW of the non-corrugated tubular sheath 907 is not exposed to the external environment and forms a face-to-face relationship with the internal wall surface 901IW of the syringe barrel cavity 901C. The forward end terminus of the non-corrugated sheath, cover, or shield 907FT is attached to at least one surface at the forward end terminus 903FT of the plunger shaft 903 or at a position along the longitudinal axis of the plunger shaft 903. The non-corrugated sheath 907 is attached to the forward terminus of the plunger shaft 903FT by one or more of the methods of molding, fusing, adhesives, ultrasonic bonding or welding, thermal bonding, etc. The rearward end terminus 907RT of the non-corrugated sheath, cover, or shield 907 is attached at or near the rearward end terminus 901RT of the syringe barrel cavity opening 901RO or to at least one surface the syringe barrel handle member 906 by one or more of the methods of molding, fusing, adhesives, ultrasonic bonding or welding, thermal bonding, etc. Such syringe barrel handle member surfaces include, but are not limited to, the rearward end face surface 906RF, forward end face surface 906FF, or side surface 906SS of the syringe barrel handle member 906. The syringe barrel handle member 906 is attached in a separate step to the rearward end terminus of the syringe barrel 901RT by one or more of the attachment methods of molding, fusing, adhesives, ultrasonic bonding or welding, thermal bonding, etc. or is molded continuous as a single unit with the syringe barrel walls 901W during the forming and molding process. The rearward end terminus 907RT of the non-corrugated sheath 907 is formed with a shape, taper, cross-section, radius, or diameter such that the rearward end terminus 907RT edges of the non-corrugated sheath 907 substantially align with the attachment surfaces of the syringe barrel 901 at or near the rearward end opening 901RO of the syringe barrel 901. This design completely seals the syringe barrel cavity 901C, by way of the rearward end opening 901RO, from the external environment and eliminates deposit of contaminants into the syringe barrel cavity 901C and onto the inner wall surfaces 901IW by way of the rearward end opening 901RO. The attachment and seals made with the forward terminus 907FT of the non-corrugated sheath 907 at the forward terminus 903FT of the plunger shaft 903 and the rearward end terminus 907RT of the of the non-corrugated sheath 907 with the syringe barrel 901 rear terminus 901RT completely seals the external environment located on the external wall 907EW side of the non-corrugated sheath 907 from the environment located on the internal wall 907IW side of the non-corrugated sheath 907.

The non-corrugated sheath, cover, or shield 907 envelops or houses the portion of the plunger shaft 903 located between the point of attachment of the forward end terminus 907FT of the non-corrugated sheath 907 and the point of attachment of the rearward end terminus 907RT of the non-corrugated sheath 907. As the non-corrugated sheath 907 is bunched or gathered by withdrawing the plunger shaft 903 from the syringe barrel cavity 901C, a shorter length of the plunger shaft 903 is enveloped by the bunched or gathered non-corrugated sheath 907 and walls 901W of the syringe barrel 901, as shown in FIG. 16B. As the bunched or gathered non-corrugated sheath is elongated or lengthened by advancing the plunger shaft 903 into and along the syringe barrel cavity 901C, the non-corrugated sheath 907 ungathers and progressively envelopes a greater length of the plunger shaft 903, as shown in FIG. 16A. The forward end terminus 907FT of the non-corrugated sheath, cover, or shield 907 is attached to at least one surface of the forward end terminus 903FT of the plunger shaft 903 or at a position along its longitudinal length by one or more of the methods of molding, fusing, adhesives, ultrasonic bonding or welding, thermal bonding, etc. The rearward end terminus 907RT of the non-corrugated sheath, cover, or shield 907 is attached at or near the rearward end opening 901RO of the syringe barrel 901 by one or more of the methods of molding, fusing, adhesives, ultrasonic bonding or welding, thermal bonding, etc. The rearward end terminus 903RT of the plunger shaft 903 is centrally molded and normal to the forward face surface 908FF of the plunger handle member 908. The plunger shaft 903 is normal to and extends from the forward face surface 908FF of the plunger handle member 908. The forward end of the body of the plunger shaft 903 extends into the syringe cavity or hollow portion 901C of the syringe barrel 901. The non-corrugated sheath, cover, or shield 907 encloses and surrounds the portion of the plunger shaft 903 extending between the point of attachment of the rearward end terminus 907RT of the non-corrugated sheath 907 at or near the syringe barrel rearward end opening 901RO and the point of attachment of the forward end terminus 907FT of the non-corrugated sheath 907 with the plunger shaft 903. The non-corrugated sheath 907 houses, encloses, or surrounds less of the plunger shaft 903 as the plunger shaft 903 is withdrawn from the syringe barrel cavity 901C. As the plunger shaft 903 is withdrawn, the non-corrugated sheath 907 gathers or bunches at or near the rearward end opening 901RO of the syringe barrel 901. The non-corrugated sheath 907 remains housed within the syringe barrel cavity 901C during use and operation of the syringe 900. When using the syringe 900, the plunger shaft 903 can be manually withdrawn from the syringe barrel cavity or hollow 901C by grasping the external walls of the syringe barrel 901EW with one hand and the plunger shaft 903 and/or plunger shaft handle member 908 with the other hand and pulling the plunger shaft 903 such that the longitudinal length of the plunger shaft 903 traverses the cavity or hollow 901C of the syringe barrel 901 and progressively emerges from the rearward end opening 901RO of the syringe barrel cavity 901C. It is noted here that the above manual operation can alternatively be performed with one hand or by machinery. It is noted that touching of the plunger shaft 903 with the hands, machinery, or other objects will not compromise the sterility of the inner walls of the syringe barrel 901IW because the non-corrugated sheath 907 functions to impede entry of contaminants. As the plunger shaft 903 is withdrawn from the syringe barrel cavity 901C, the walls of the non-corrugated sheath 907 surrounding the plunger shaft 903 are caused to bunch or gather along the longitudinal axis of the non-corrugated sheath 907 thereby shortening the non-corrugated sheath 907 along its longitudinal axis in a direction toward the rearward end opening 901RO of the syringe barrel 901. The length of the plunger shaft 903 enveloped or housed within the hollow or cavity 907C of the non-corrugated sheath 907 decreases as more of the plunger shaft 903 emerges from the cavity 901C and rearward end opening 901RO of the syringe barrel 901. As the length of the non-corrugated sheath 907 within the syringe barrel cavity 901C bunches or gathers, the non-corrugated sheath 907 shortens within the syringe barrel cavity 901C enabling the plunger shaft 903 to be withdrawn from the hollow or cavity 901C of the syringe barrel 901, as depicted in FIG. 16B. The non-corrugated sheath 907 shortens and encloses or envelopes less of the plunger shaft 903 as more of the plunger shaft 903 is further withdrawn from the syringe barrel hollow 901C. As the plunger shaft 903 is withdrawn from the syringe barrel hollow 901C, a space 901S is formed between the piston head 904HP of the plunger piston 904P and the tapered internal walls 901TIW of the syringe barrel 901. The non-corrugated sheath 907 bunches or gathers and remains in the shortened state until a force is applied along the longitudinal axis of the plunger shaft 903 to cause the plunger shaft 903 to advance into the syringe barrel cavity 901C and cause the gathered or bunched non-corrugated sheath 907 to lengthen. It is not necessary for an individual, or machinery when used to manipulate the syringe 900, to hold the withdrawn plunger shaft 903 to ensure that the non-corrugated sheath 907 remains in its shortened, bunched, or gathered state. The non-corrugated sheath 907 is designed and manufactured such that it does not automatically recoil or recover to its lengthened state after being bunched or gathered, or automatically recoil or recover to its bunched or gathered state after being elongated or lengthened. A force must be applied along the longitudinal axis of the plunger shaft 903 to cause the bunched or gathered non-corrugated sheath 907 to elongate within the syringe barrel cavity 901C. Lengthening of the non-corrugated sheath 907 can be performed by applying pressure to the rearward end face surface 908RF of the plunger handle member 908 or along the plunger shaft 903 to advance the plunger shaft 903 in the direction toward the forward end opening 901FO of the syringe barrel 901 and cause the non-corrugated sheath 907 to lengthen or elongate and the plunger shaft 903 and the piston 904P to traverse the syringe barrel cavity 901C toward the tapered internal wall 901TIW surfaces of the syringe barrel cavity 901C and the syringe entrance/exit port 901EP. The non-corrugated sheath 907 is manufactured such that it does not impede traversal of the plunger shaft 903 and piston 904P along the syringe barrel cavity 901C. The piston rim 904PR slidably engages and maintains a tight seal with the internal wall surfaces 901IW of the syringe barrel cavity 901C as the piston 904P traverses the syringe barrel cavity 901C. Medication or other types of materials drawn into the syringe barrel cavity 901C remain forward of the piston head 904HP during withdrawal and advancement of the plunger shaft 903 and piston 904P such that the medication or other types of materials drawn into the syringe barrel cavity 901C can be ejected from the syringe barrel cavity 901C through the entrance/exit port 901EP. The tapered forward end walls 901TW of the syringe barrel 901 form a reduced diameter neck 901RDN with a forward end opening 901FO/entrance-exit port 901EP at the forward end terminus of the syringe barrel 901. The reduced diameter neck 901RDN mates with the hub 905H of a needle 905, through frictional engagement. As an alternative, a circumferential wall can be formed around the external walls of the reduced diameter neck 901RDN. Threads or grooves are formed on the inside surfaces of the encircling circumferential wall such that the hub 905H of the needle 905 can be rotated or twisted on the threads or grooves and locked onto the reduced diameter neck 901RDN and within the circumferential wall. Alternatively, threads or grooves can be formed on the reduced diameter neck 901RDN and on the inner wall surfaces of the hub 905H such that the hub 905H can be directly rotated or twisted onto the reduced diameter neck 901RDN. In operation, medication or other material is drawn up from a vial or ampoule, ampul, ampule, for example, by first introducing the needle 905, which is attached to the reduced diameter neck 901RDN of the entrance/exit port 901EP, into the vial or ampoule, ampul, ampule, containing the medication or other material. Next, the non-corrugated sheath 907 is caused to gather and/or bunch by pulling the plunger handle member 908. This also causes the plunger shaft 903 and piston 904P to traverse the syringe barrel cavity 901C away from the tapered internal walls 901TIW of the syringe barrel cavity 901C and toward the rearward end opening 901RO. As the plunger piston 904P traverses the syringe barrel cavity 901C, the piston rim 904PR slidably engages and maintains a tight seal with the internal wall surfaces 901IW of the syringe barrel cavity 901C. A vacuum is created in the space located between the forward end of the piston head 904HP and the tapered internal wall surface 901TIW of the syringe barrel 901 as the piston head 904HP is pulled away from the tapered internal walls 901TIW. The vacuum created causes the liquid medication or other material in the vial, or ampul, ampoule, ampule to be drawn into the syringe barrel cavity 901C through the needle 905, which is frictionally attached by a hub 905H to the outer walls of the reduced diameter neck 901RDN, and the entrance/exit port 901EP. The needle 905 is then removed from the vial, or ampul, ampoule, ampule of medication or other material and positioned in the needle port of an appropriate bag or bottle of intravenous solution. The liquid medication is then injected into the bag or bottle of intravenous solution. The reduced diameter neck 901RDN can be manufactured or molded to operate with any existing line of hypodermic needles, tubing, caps, closures, etc.

An advantage of using the non-corrugated sheath 907 within the syringe barrel cavity 901C is the protection provided by the sheath 907 to the internal cavity wall surfaces 901IW of the syringe barrel 901 in that contaminants deposited onto the external wall surface 907EW of the non-corrugated sheath 907, and/or external wall surfaces 901EW of the syringe barrel 901, and/or the plunger shaft 903 or handle members will not jeopardize the sterility of the inner cavity 901C of the syringe barrel 901 because the contaminants cannot penetrate the walls of the non-corrugated sheath 907 or the syringe barrel 901 or shaft 903. Also, the design inhibits separation of the plunger shaft 903 from the rearward end opening 901RO of the syringe barrel 901. The syringe design also functions as a dam or barrier to collect or accumulate, within the syringe barrel cavity, medications or other types of materials drawn into the syringe that leak past the piston due to piston failure.

Syringe Having a Straight Segment and Corrugated Segment Syringe Barrel

A second embodiment of the instant invention, as shown by FIG. 3, illustrates a new and improved syringe 200 formed of a cylindrical syringe barrel 201 and a cylindrical plunger member 205. The syringe barrel 201 is formed with a straight segment 202 and a corrugated segment 203. The straight segment 202 is located on the forward end section of the syringe barrel 201 and the corrugated segment 203 is located at the rearward end section of the syringe barrel 201. The rearward end terminus 201RT of the syringe barrel 201 is molded to at least one surface of a plunger handle member 204. The at least one surface includes, but is not limited to, the forward face surface 204FF, the rearward face surface 204RF, and the side surface 204SS. The rearward end terminus 205RT of the plunger shaft 205 is centrally molded to the forward face surface 204FF of the plunger handle member 204. A rearward end portion 205RP of the plunger shaft body 205 is enclosed or surrounded by the corrugated segment 203 of the syringe barrel 201. The syringe barrel 201 has a forward open-end 201FO/entrance exit port 201EP and a rearward closed end 201RC. The rearward closed end 201RC is closed by the plunger shaft handle member 204, which is molded to the rearward end terminus 201RT of the syringe barrel 201. The open-end 201FO is located at the forward end terminus 201FT of the syringe barrel 201. The forward end of the syringe barrel 201 tapers to a reduced diameter neck 201RDN at the entrance/exit port 201EP and forms a mating surface for the hub 208H of a needle 208. A forward end portion 205FP of the plunger shaft body 205, and a plunger piston 205P located at the forward end terminus 205FT of the plunger shaft 205, is enclosed or surrounded by the straight segment 202 of the syringe barrel 201. The plunger piston 205P and plunger shaft body 205 can be caused to traverse the syringe barrel cavity or hollow 207 by manually grasping the syringe barrel external wall surface 201EW along the straight segment 202 with one hand and the plunger shaft handle member 204 and/or corrugated segment 203 with the other hand and pulling the plunger shaft handle member 204 and/or corrugated segment 203 such that the rearward end terminus 205RT of the plunger shaft 205 and the forward face surface 204FF of the handle member 204 move away from the straight segment 202 of the syringe barrel 201 causing lengthening of the syringe barrel 201 and elongation of the corrugated segment 203, as shown in FIG. 4. It is also noted that the above manual operation can be performed with one hand. Simultaneously, the plunger piston rim 205PR slidably engages the internal wall surfaces 201IW of the straight segment 202 of the syringe barrel 201 as it traverses the cavity or hollow 207 of the syringe barrel 201. In order to assist the user in lengthening of the syringe 200, a syringe barrel handle member (not shown) can be molded to the external surface of the syringe barrel wall surface 201EW along the straight segment 202. The syringe barrel handle member (not shown) can be used as a wall for leverage to assist the user in lengthening or shortening the syringe barrel 201 while pulling or pushing the plunger shaft handle member 204. The syringe barrel handle member can take any desired shape such as flat wall or plate, curved, or finger grip design, as examples. The peaks 203P, valleys 203V, and walls 203W of the corrugations, pleats, or folds in the corrugated segment 203 of the syringe barrel 201 are caused to separate along the longitudinal axis of the syringe barrel 201 as the plunger handle member 204 is pulled thereby lengthening the syringe barrel 201 along its longitudinal axis, as shown in FIG. 4. At least a portion of the plunger shaft 205 remains centrally located within, and the rim 205PR of the piston 205P remains in contact with, the internal wall surfaces 201IW of the hollow or cavity 207 of the syringe barrel straight segment 202 during elongation or lengthening of the syringe barrel 201. The rearward end terminus 205RT of the plunger shaft 205 and the syringe barrel rearward end terminus 201RT of the corrugated segment 203 remains molded to the forward end face surface 204FF of the plunger handle member 204. The rearward end terminus 207RT of the corrugated segment 203 can alternatively be molded to the rear face surface 204RF and side surface 204SS, or a combination thereof. As the corrugations or folds of the corrugated segment 203 are caused to separate, the corrugated segment 203 of the syringe barrel 201 lengthens causing the forward portion of the plunger shaft 205FP to traverse the straight segment 202 of the syringe barrel cavity 207, and the plunger piston 205P attached to the forward end terminus 205FT of the plunger shaft 205 to slide along the straight segment 202 of the syringe barrel cavity 207 in the direction of the corrugated segment 203. This is because the rearward end terminus 205RT of the plunger shaft 205 is centrally molded to the forward face surface 204FF of the plunger handle member 204 which moves in a direction away from the straight segment 202 of the syringe barrel 201 during lengthening causing the plunger 205 and piston 205P to traverse the syringe barrel cavity 207 toward the corrugated segment 203. The plunger piston rim 205PR is in contact and forms a seal with the internal cavity walls 201IW of the syringe barrel 201. The corrugated segment 203 encloses or encircles a greater length of the plunger shaft body 205 as the plunger is drawn further along the syringe barrel hollow or cavity 207, as shown in FIG. 4. The corrugated segment 203 remains in the lengthened or elongated state until a force is used to compress or collapse together the folds or corrugations of the corrugated segment 203, which shortens the syringe barrel 201. That is, it is not necessary for the individual pulling the plunger handle member 204 and lengthening the corrugated segment 203 to hold the plunger handle member 204 or corrugated segment 203 such that the corrugated segment 203 remains in its lengthened position or elongated state. The corrugated segment 203 is designed and manufactured such that it does not automatically recoil from an elongated or shortened position. An axial force must be applied to the syringe barrel 201 to cause the corrugated walls of the elongated corrugated segment 203 to move toward each other or together such that the syringe barrel 201 shortens along its longitudinal axis. Also, a force must be applied to cause the corrugated segment 203 to lengthen. As the walls of the corrugated segment 203 are forced together, the syringe barrel 201 shortens. Shortening of the corrugated segment 203 and syringe barrel 201 can be performed by pressing the rearward end face surface 204RF of the plunger shaft handle member 204 along the longitudinal axis of the syringe barrel 201 to cause the corrugated segment 203 to shorten and the plunger piston 205P to slide along the internal cavity walls 201IW of the syringe barrel cavity 207 toward the forward end terminus 201 FT and toward the syringe barrel entrance/exit port 201EP such that medication or other materials in the syringe barrel cavity 207 is ejected from the syringe 200 through the entrance/exit port 201EP.

In operation, medication or other material is drawn up from a vial or ampoule, ampul, ampule, for example, by first introducing the needle 208, which is attached to the reduced diameter neck 201RDN of the entrance/exit port 201EP, into the vial or ampoule, ampul, ampule, containing the medication or other material. Next, the corrugations or folds of the corrugated segment 203 of the syringe barrel 201 are caused to separate by pulling the plunger handle member 204. This also causes the plunger shaft 205 and piston 205P to traverse the syringe barrel cavity 207 along the straight segment 202 and away from the tapered internal walls 201TIW of the syringe barrel cavity 207 and toward the corrugated segment 203. As the plunger piston 205P traverses the syringe barrel cavity 207, the plunger piston rim 205PR slidably engages and maintains a tight seal with the internal wall surfaces 201IW of the syringe barrel cavity 207. This causes the air column in the bore or cavity 207 located behind the plunger piston 205P and adjacent the body of the plunger shaft 205 to be pushed into the elongated corrugated segment 203 of the syringe barrel 201. A vacuum is created in the space located between the forward end of the piston head 205HP and the tapered internal wall surface 201TIW of the syringe barrel 201 as the piston head 205HP is pulled away from the tapered internal walls 201TIW. The vacuum created causes the liquid medication or other material in the vial, or ampul, ampoule, ampule to be drawn into the syringe barrel cavity 207 through the needle 208, which is frictionally attached to the outer walls of the reduced diameter neck 201RDN, and the entrance/exit port 201EP. The needle 208 is then removed from the vial, or ampul, ampoule, ampule of medication or other material and positioned in the needle port of an appropriate bag or bottle of intravenous solution. The liquid medication is then injected into the bag or bottle of intravenous solution. The reduced diameter neck 201RDN is manufactured or molded to operate with any existing line of hypodermic needles, tubing, caps, closures, etc.

An advantage of using the syringe 200 having a corrugated segment 203 and a straight segment 202 is the protection provided to the plunger shaft 205 and the internal cavity wall surfaces 201IW in that contaminants deposited onto the external wall surfaces of the syringe barrel 201EW will not jeopardize the sterility of the inner cavity 207 of the syringe barrel 201 because the contaminants cannot penetrate the walls 201W of the syringe barrel 201. It is also noted that the peaks, pleats, valleys, and walls of the corrugations of the corrugated segment 203 can have any desired shape such as curved, triangular, square, etc., so long as the desired mechanical functioning of the corrugated segment as set forth above is not compromised.

Syringe Having Syringe Barrel and Plunger Member

A third embodiment of the instant invention, as shown by FIGS. 5, 6A and 6B, illustrates a new and improved syringe 300 formed of a cylindrical syringe barrel 301 and a cylindrical plunger member 302. The syringe barrel 301 and the plunger member 302 have mating concentric plunger member and syringe barrel walls 302W and 301W, respectively. The plunger member 302 has a wall 302W having an open-end 302OE and a closed end 302CE. The closed end 302CE of the plunger member 302 has a flat bottom floor structure 304 forming a cup-shaped inner cavity. It is noted that other shapes can be used for the bottom floor structure; and thus, the shapes are not restricted to flat. The flat bottom floor structure 304 has forward and rearward face surfaces 304FF and 304RF, respectively. The flat bottom floor structure 304 can be molded continuous with the plunger member cylindrical walls 302W. The inside diameter of the plunger member 302 is constant along its length. The forward face surface 304FF of the flat bottom floor structure 304 has molded thereto the rearward end terminus 305RT of a plunger shaft 305. The plunger shaft 305 is concentrically surrounded by the internal face wall surfaces 302IW of the plunger member 302 along its longitudinal length. The plunger shaft 305 extends centrally from the forward face surface 304FF of the flat bottom floor structure 304 along the length of the internal face wall surfaces 302IW of the plunger member 302 which concentrically surround, enclose, or house the plunger shaft 305. The plunger shaft 305 has a piston 305P attached to its forward end terminus 305FT by one or more of the methods of mounting, twisting, turning, rotating, or screwing onto threads located at the forward terminus of the plunger shaft; fusing; molding; adhesives; ultrasonic bonding or welding; thermal bonding; etc. The position of the piston rim 305PR of the piston head 305HP coincides with the open-end terminus 302OT of the plunger member wall 302W. The syringe barrel 301 is formed with two open ends at opposite ends of the syringe bore or cavity 301C—one having a smaller forward end diameter opening 301FO. The rearward end larger diameter opening 301RO is located at the rearward end terminus 301RT of the syringe barrel 301. The smaller forward end diameter opening 301FO has a reduced diameter neck 301RDN at the entrance/exit port 301EP. The forward end smaller diameter opening 301FO is located at the forward end terminus 301FT of the syringe barrel 301. The syringe barrel 301 has an outside wall diameter less than the inside wall diameter of the plunger member 302 along the entire length of the syringe barrel 301. The inside diameter of the syringe barrel 301 is equal to or slightly less than the diameter of the piston rim portion 305PR of the plunger piston 305P attached by one or more of the methods of mounting; twisting, turning, rotating, or screwing onto threads located at the forward terminus of the plunger shaft; fusing; molding; adhesives; ultrasonic bonding or welding; thermal bonding; etc., at the forward end terminus 305FT of the plunger shaft 305. The piston rim portion 305PR of the plunger piston 305P mates with and forms a seal with the internal wall surfaces 301IW of the bore or cavity 301C of the syringe barrel 301. The internal and external wall surfaces 301IW and 301EW of the syringe barrel 301 taper at the syringe barrel forward end forming the reduced diameter neck 301RDN having the smaller diameter forward end opening 301FO and an entrance/exit port 301EP through which fluid medications and other solutions or fluids enter and exit the cavity 301C of the syringe barrel 301. The external wall surface 301EW of the reduced diameter neck 301RDN forms a mating surface for the hub 307H of a needle 307. At a point rearward to the forward end small diameter opening 301FO of the syringe barrel 301, a handle member 301H of any desired design is provided for assisting the user in sliding of the plunger member 302 relative to the syringe barrel 301. The handle member 301H can be formed during the forming process of the syringe barrel 301, or formed in a separate molding or attachment operation.

The plunger member 302 is mated with the syringe barrel 301 by fitting the plunger piston 305P located at the forward end terminus of the plunger shaft 305FT into the central cavity or bore 301C of the syringe barrel 301. As the piston 305P and plunger shaft 305 are slid into the central cavity 301C of the syringe barrel 301, the internal wall surfaces 302IW of the plunger member 302 form a face-to-face relationship with the external wall surfaces 301EW of the syringe barrel 301. The full length of the plunger shaft 305 and piston 305P slide into the full length of the central cavity 301C of the syringe barrel 301 such that the head of the piston 305HP abuts the tapered internal walls 301TIW of the syringe barrel 301. The contour of the piston head 305HP of the piston 305P matches and follows the contours of the tapered internal wall 301TIW of the syringe barrel 301 to form a seal at the forward end opening 301FO which is the entrance/exit port 301EP. The terminus surfaces 301RT of the rearward larger diameter opening 301RO can abut with the forward face surface 304FF of the flat bottom floor structure 304 of the plunger member 302. In operation the plunger member wall 302W concentrically surrounds the syringe barrel wall 301W. Medication or other fluid or material is drawn up from a vial or ampoule, ampul, ampule, for example, by first introducing the needle 307, which is attached to the external walls of the reduced diameter neck 301RDN, into the vial or ampule, ampoule, ampul, ampule containing the medication or other material. Next, the internal wall surface of the plunger member 302IW is concentrically slid alongside the length of the external wall surface of the syringe barrel 301EW while maintaining a concentric glide space GS between the internal wall surface 302IW of the plunger member 302 and the external wall surface 301EW of the syringe barrel 301. Simultaneously, the piston rim 305PR of the plunger piston 305P, which is attached at the forward end terminus of the plunger shaft 305FT, slidably engages and maintains a tight seal with the internal wall surfaces 301IW of the syringe barrel cavity 301C while moving along the syringe barrel cavity 301C and away from the tapered internal walls 301TIW of the syringe barrel 301, as shown in FIG. 6A. This causes the air column in the bore or cavity 301C located behind the plunger piston 305P and adjacent the plunger shaft 305 to be expelled or pushed out of the cavity 301C. A vacuum is created in the space located between the forward end of the piston head 305HP and the tapered internal wall surfaces 301TIW of the syringe barrel 301. The vacuum causes the liquid medication or other fluid in the vial or ampoule, ampul, ampule, to be drawn into the syringe barrel cavity 301C through the needle 307, hub 307H, and entrance/exit port 301EP/301FO. The needle 307 is then removed from the vial or ampoule, ampul, ampule, and positioned in the needle port of an appropriate bag or bottle of intravenous or other type of solution. By applying pressure to the rearward face surface of the flat bottom floor structure 304RF, or along the plunger member 302 in the direction of the tapered internal wall surfaces 301TIW, the liquid medication or other material can then be injected into the bag or bottle of intravenous or other type of solution. This pressure causes the longitudinal length of the plunger shaft 305 and the plunger piston 305P to advance along the syringe barrel cavity 301C toward the tapered internal wall surfaces 301TIW of the syringe cavity 301C. The piston rim 305PR slidably engages and maintains a tight seal with the internal wall surfaces 301IW of the syringe cavity 301C as the piston 305P advances. The liquid medication or other material remains forward of the piston head 305HP during advancement and withdrawal of the plunger shaft 305 and piston 305P.

An advantage of using the syringe 300 having mating concentric plunger and syringe barrel walls 302W and 301W, respectively, is the protection provided to the plunger shaft 305 and the internal cavity wall surfaces 301IW of the syringe barrel 301 in that contaminants deposited onto the external wall surfaces 302EW of the plunger member 302 or external wall surfaces of the syringe barrel 301EW will not jeopardize the sterility of the syringe barrel cavity 301C because the design discourages entry of contaminants into the syringe barrel cavity 301C.

An added feature for the third embodiment, as shown by FIG. 6B, is to provide a first sealing ring 302SR projecting perpendicularly from the inner wall surface 302IW of the plunger member 302 at or near the open end terminus 302OT of its open end 302OE. The sealing ring 302SR is a continuous ring that follows the complete circumference of the internal wall 302IW of the plunger member 302. A second sealing ring 301SR is formed projecting perpendicularly from on the external wall surface 301EW of the syringe barrel 301 at or near its rearward end large diameter opening 301RO. The sealing rings 301SR and 302SR provide several advantages. When the walls 302W of the plunger member 302 are concentrically mated with the walls 301W of the syringe barrel 301, the sealing rings 302SR and 301SR project or extend into the glide space GS. First, the sealing rings 301SR and 302SR seal the glide space GS existing between the internal wall surface 302IW of the plunger member 302 and the external wall surface 301EW of the syringe barrel 301. This discourages entry of contaminants such as dirt, dust, microorganism, glass fragments, and pathogens carried by the air, hands, fingers, gloves, hair, clothing, etc., from becoming deposited onto the internal surfaces 301IW of the syringe barrel cavity 301C. Second, the sealing rings 302SR and 301SR function to prevent accidental separation of the plunger member 302 from the syringe barrel 301 through abutment of the sealing rings 301SR and 302SR as the walls of the plunger member 302W are moved relative to the walls of the syringe barrel 301W. Third, the sealing rings 301SR and 302SR function as a dam or barrier to fluids that collect or accumulate in the cup of the inner cavity 302C of the plunger member 302 due to piston failure. The sealing rings are continuous and follow the complete circumference or perimeter of the surface from which it projects.

The sealing rings 301SR and 302SR can be formed of a rigid, semi-rigid, or flexible material. The sealing ring flexible material has bendable characteristics and can provide a sweeping, wiping action to the surface for which it contacts.

Syringe Having Concentric Syringe Barrels and a Plunger Member

A fourth embodiment of the instant invention, as shown by FIGS. 7, 8A and 8B, illustrates a new and improved syringe 400 formed of cylindrical concentric syringe barrels 401OB and 401IB and a cylindrical plunger member 402. The plunger member 402 has a wall 402W with a forward open-end 402FO and a rearward closed end 402RC. The rearward closed end 402RC of the plunger member 402 has a flat bottom floor structure 403 forming a cup. It is noted that other shapes can be used for the bottom floor structure; and thus, the shapes are not restricted to flat. The flat bottom floor structure 403 has forward end and rearward end face surfaces 403FF and 403RF, respectively. The flat bottom floor structure 403 can be molded continuous with the walls of the plunger member 402W. The inside diameter of the plunger member walls 402W is constant along the length of the plunger member 402. The forward end face surface 403FF of the flat bottom floor structure 403 has molded thereto the rearward end terminus 404RT of a plunger shaft 404. The plunger shaft 404 can also be molded continuous with the flat bottom floor structure 403 during the molding operation. The plunger shaft 404 is centrally located within and surrounded by the internal face surfaces of the walls 402IW of the plunger member 402 which extend normal from the forward end face 403FF of the flat bottom floor structure 403. The plunger shaft 404 extends centrally and normal from the forward end face surface 403FF of the flat bottom floor structure 403 along the length of the internal wall face surfaces 402IW of the plunger member 402. The walls 402W of the plunger member 402 surround the plunger shaft 404. The plunger shaft 404 has a piston 404P attached to its forward end terminus 404FT by one or more of the methods of mounting; twisting, turning, rotating, or screwing onto threads located at the forward terminus of the plunger shaft; fusing; molding; adhesives; ultrasonic bonding or welding; thermal bonding; locking attachment; etc. The position of the piston rim 404PR of the plunger piston 404P substantially coincides with the forward end terminus 402FT of the wall of the plunger member 402W at its forward open-end 402FO. An inner concentric syringe barrel 401IB is formed with two open ends located at opposite ends of the inner concentric syringe barrel cavity 401C—the rearward end opening 401RO having a larger diameter opening than the forward end opening 401FO. The rearward end larger diameter opening 401RO is located at the rearward end terminus 401RT of the inner concentric syringe barrel 401IB. The forward end smaller diameter opening 401FO is located at the forward end terminus 401FT of the concentric syringe barrel 401OB and 401IB which has a reduced diameter neck 401RDN at the entrance/exit port 401FO/401EP. The concentric syringe barrel is formed with inner and outer syringe barrels 401IB and 401OB, respectively. The inner syringe barrel 401IB has an outside diameter less than the inside diameter of the plunger member walls 402W along the entire length of the inner syringe barrel 401IB. The inside diameter of the inner syringe barrel 401IB is equal to or slightly less than the diameter of the rim portion 404PR of the plunger piston 404P attached by one or more of the methods of mounting; twisting, turning, rotating, or screwing onto threads located at the forward terminus of the plunger shaft; fusing; molding; adhesives; ultrasonic bonding or welding; thermal bonding; locking attachment; etc., at the forward end terminus 404FT of the plunger shaft 404. The piston rim portion 404PR of the plunger piston 404P mates with and forms a seal with the inner barrel internal wall surfaces 401IBIW of the bore or cavity 401C of the inner syringe barrel 401IB. The internal and external wall surfaces of the inner syringe barrel 401IBIW and 401IBEW, respectively, taper at their forward ends forming the reduced diameter neck 401RDN having the forward end smaller diameter opening 401FO and an entrance/exit port 401EP through which fluid medications and other solutions or fluids enter and exit the cavity 401C. The external wall surface of the reduced diameter neck 401RDN forms a mating surface for the hub 405H of a needle 405. The outer syringe barrel 401OB concentrically encircles the inner syringe barrel 401IB forming concentric syringe barrels. The internal wall surfaces 401OBIW of the outer syringe barrel 401OB are in face-to-face relationship with the external wall surfaces 401IBEW of the inner syringe barrel 401IB and are separated by a distance which forms a second cavity or glide space 406/GS between the wall of the inner syringe barrel 401IB and the wall of the outer syringe barrel 401OB. This second cavity or space 406/GS is open at its rearward end 406R and closed at its forward end 406F forming a cup shape. The rearward open-end 406R receives the walls 402W of the plunger member 402. This second cavity or space 406/GS functions as a glide space for the walls 402W of the plunger member 402. At a point located on the external wall surface 401OBEW of the outer syringe barrel 401OB, a handle member 401H is provided for assisting the user in sliding the plunger member 402 relative to the inner and outer syringe barrels 401IB and 401OB, respectively. The handle member 401H can be formed during the forming process of the syringe barrels 401OB and 401IB, or formed in a separate molding or attachment operation.

The plunger member 402 is mated with the concentric syringe member 401IB, 401OB by fitting the plunger piston 404P, located at the forward end terminus of the plunger shaft 404FT, into the central cavity or bore 401C formed by the walls 401IBW of the inner syringe barrel 401IB. As the piston 404P and plunger shaft 404 are slid into the central cavity 401C of the inner syringe barrel 401IB, the internal wall surfaces 402IW of the plunger member 402 form a face-to-face relationship with the external wall surfaces 401IBEW of the inner syringe barrel 401IB. Also, the external wall surfaces 402EW of the plunger member 402 form a face-to-face relationship with the internal wall surfaces 401OBIW of the outer syringe barrel 401OB. The full length of the plunger shaft 404 and piston 404P slide into the full length of the central cavity 401C of the inner syringe barrel 401IB such that the head of the piston 404HP abuts the tapered internal walls 401TIW of the inner syringe barrel 401IB. The contour of the head of the piston 404HP matches and follows the contours of the tapered internal walls 401TIW of the inner syringe barrel 401IB to form a seal at the forward end opening 401FO of the entrance/exit port 401EP. The rearward terminus surfaces 401RT of the rearward end larger diameter opening 401RO of the inner syringe barrel 401IB can abut with the forward face surface 403FF of the flat bottom floor structure 403 of the plunger member 402 with full insertion of the plunger shaft 404 into the central cavity or bore 401C of the inner syringe barrel 401IB. In operation, the walls of the inner and outer concentric syringe barrels 401IBW and 401OBW concentrically sandwich the plunger member walls 402W. In operation, medication or other material is drawn up from a vial or ampoule, ampul, ampule, for example, by first introducing the needle 405, attached by the hub 405H to the reduced diameter neck 401RDN of the entrance/exit port 401EP, into the vial or ampoule, ampul, ampule. Next, the wall surfaces 402W of the plunger member 402 are slid within the glide space 406/GS existing between and along the length of the external wall surface 401IBEW of the inner syringe barrel 401IB and the internal wall surface 401OBIW of the outer syringe barrel 401OB, respectively, such that the walls 402W of the plunger member 402 slide along and out of the glide space 406/GS. Simultaneously, the piston rim 404PR of the piston 404P, attached at the forward end terminus 404FT of the plunger shaft 404, slidably engages and maintains a tight seal with the internal wall surfaces 401IBIW of the inner syringe barrel 401IB while moving along the inner syringe barrel cavity 401C and away from the tapered internal wall 401TIW of the inner syringe barrel 401IB. This causes the air column in the bore or cavity 401C located behind the piston 404P and adjacent the plunger shaft 404 to be pushed out of the syringe cavity 401C creating a vacuum in the space located between the forward end of the piston head 404HP and the tapered internal wall surfaces 401TIW of the inner syringe barrel cavity 401C. The vacuum causes the liquid medication or other material in the vial or ampoule, ampul, ampule, to be drawn into the inner syringe barrel cavity 401C through the needle 405, hub 405H, and entrance/exit port 401EP. The needle 405 is then removed from the medication vial or ampoule, ampul, ampule, and positioned in a needle port of an appropriate bag or bottle of intravenous solution. The liquid medication can then be injected into the bag or bottle of intravenous solution by applying pressure to the rearward face surface 403RF of the flat bottom floor structure 403. This pressure causes the longitudinal length of the plunger shaft 404 and the plunger piston 404P to advance within and along the inner syringe barrel cavity 401C toward the tapered internal wall surfaces 401TIW of the syringe cavity 401C. The piston rim 404PR slidably engages and maintains a tight seal with the internal wall surfaces of the inner barrel 401IBIW of the syringe cavity 401C as the piston 404P and plunger shaft 404 are advanced. The liquid medication or other material remains forward of the piston head 404HP in the space located between the forward end of the piston head 404HP and the tapered internal walls 401TIW of the syringe barrel cavity 401C during advancement and withdrawal of the plunger shaft 404 and piston 404P. The liquid medication or other material is ejected out of the entrance/exit port 401EP of the inner syringe barrel 401IB as the plunger shaft 404 is advanced.

An advantage of using a syringe having concentric inner and outer syringe barrels 401IB and 401OB, which functions concentrically with a plunger member 402, is the protection provided to the plunger shaft 404 and the internal wall surfaces 401IBIW of the syringe cavity 401C in that contaminants deposited onto the external wall surfaces 402EW of the plunger member 402 or the external wall surfaces 401OBEW of the outer syringe barrel 401OB will not jeopardize the sterility of the cavity 401C of the inner syringe barrel 401IB because the syringe design discourages and prevents entry of contaminants into the inner syringe barrel cavity 401C, ultimately protecting the medication or other materials.

An added feature for the fourth embodiment, as shown in FIG. 8B, is to provide a first sealing ring 401 SR projecting perpendicularly from the internal wall surface 401OBIW of the outer syringe barrel 401OB at or near the glide space 406/GS rearward end opening 406R. A second sealing ring 402EWSR can be formed projecting perpendicularly from the external wall surface 402EW of the plunger member 402 at or near the terminus of its forward open-end 402FO. A third sealing ring 402IWSR can be formed projecting perpendicularly from the internal wall surface 402IW of the plunger member 402 at or near the terminus of its open forward end 402FO. A fourth sealing ring 401IBSR can be formed projecting perpendicularly from the external wall 401IBEW surfaces of the inner syringe barrel 401IB at or near the rearward end terminus 401RT of its open-end 401RO. One or more of the above sealing rings can be formed or provided on the inner or outer barrel wall surfaces 401IB and 401OB of the syringe 400 or the plunger member walls 402W. The sealing rings provide several advantages. First the sealing rings seal the glide space 406/GS existing between the internal wall surface 401OBIW of the outer syringe barrel 401OB and the external wall surface 401IBEW of the inner syringe barrel 401IB. This discourages and prevents entry of contaminants such as dirt, dust, fibers, hair, glass fragments, foreign particles, microorganisms, pathogens, pyrogens, and any other type of contaminant, carried by air, hands, fingers, gloves, hair, clothing, etc., from becoming deposited onto the internal wall surfaces 401IBIW of the syringe barrel cavity 401C. Second, the sealing rings function to prevent accidental separation of the plunger member 402 from the concentric syringe barrels 401IB and 401OB through abutment of the sealing rings of the concentric syringe barrels 401IB and 401OB with the sealing rings of the plunger member 402 as the walls of the plunger member 402W are moved relative to the walls 401IBW and 401OBW of the inner and outer concentric syringe barrels 401IB and 401OB. Third, the sealing rings function as a dam or barrier to medications, fluids, or solutions that collect or accumulate in the cup of the plunger member 402 due to piston failure. The sealing rings can be formed of a rigid, semi-rigid, or flexible material. When flexible material is used for the sealing ring, a bendable characteristic is provided to the sealing ring that allows the sealing ring to perform a sweeping, wiping action to the surface for which it extends to and contacts during movement of the walls of the plunger member 402W to the walls 401IBW and 401OBW of the inner and outer concentric syringe barrels 401IB and 401OB. The sealing rings extend perpendicularly from the surface of a syringe barrel wall or a plunger member wall. The sealing ring is a continuous ring that follows and encircles the circumference or perimeter of the surface from which it projects.

Syringe Having Contaminant Shield or Barrier

In a fifth embodiment of the instant invention, it is an object to provide a new and improved syringe having a contaminant shield positioned at or near the rearward end opening of the syringe barrel. FIG. 9 shows a longitudinal cross-section of the syringe of the fifth embodiment of the instant invention. FIGS. 10A and 10B are views along the longitudinal axis of the syringe of FIG. 9 as viewed from a cross-section taken along the line 10—10. The contaminant shield 520 is formed on the rearward end section of the syringe barrel inner wall surfaces 502IW of syringe barrel 502 with a semi-rigid and flexible material and projects perpendicularly from the circumference or perimeter of the syringe barrel inner wall surfaces 502IW into the syringe barrel cavity 502C and surrounds and abuts the surfaces and walls of the ribs 501R which form the spine of the plunger shaft 501. It is noted that ribs are not required in the design feature for the plunger shaft and that any design shape or cross-section can be used for the plunger shaft. Such shapes include, but are not limited to, rectangular, triangular, cylindrical, hexagonal, etc. The contaminant shield 520 can be formed from, but is not limited to, a single material, a mixture of materials, one or more lamina of one or more materials, lamina composite having one or more materials, fiber composite having one or more materials, etc. which will provide a semi-rigid and flexible characteristic to the shield walls 508. The shield walls 508 have centrally formed therethrough an opening having the shape of the cross-section of the plunger shaft 501 used in conjunction with syringe 500. These cross-sectional shapes include, but are not limited to, square, triangular, cylindrical, hexagonal, etc. To facilitate attachment or molding of the contaminant shield walls 508 to the inner wall surface 502IW of the syringe barrel cavity 502C, a dovetail groove 504DT, or similar locking groove, can be formed on or in the surface of the inner wall 502IW, as shown in FIGS. 9 and 11, along the circumference or perimeter of the syringe cavity 502C at or near the rearward end opening 502RO of the syringe barrel 502. During the molding process, the dovetail groove 504DT formed in the inner wall surface 502IW of the syringe cavity 502C receives and anchors the material used to form the contaminant shield walls 508. The contaminant shield walls 508 have a forward end face surface 508FF facing into the syringe cavity 502C of the syringe barrel 502 and a rearward end face surface 508RF facing the plunger handle member 504. It is noted that the plunger shaft 501 can have any cross-sectional shape desired; such as cylindrical, ribs, triangular, square, etc. Accordingly, the periphery 508P of the opening formed in the contaminant shield walls 508 of contaminant shield 520 defines the cross-sectional shape of the plunger shaft 501.

Alternatively, the cover can be formed of two parts, as shown in FIG. 10B. The first part 506 is formed of a material providing a rigid or hard characteristic or quality to the contaminant shield 510. The first part 506 can be formed of the same material as, and molded continuous with the circumference inner wall surface 502IW of, the syringe barrel 502 at or near the rearward end opening 502RO of the syringe barrel 502. The first part 506, when formed, projects into the syringe barrel cavity 502C perpendicularly from the circumference or perimeter of the inner wall surface 502IW of the syringe barrel 502. The first part has a forward face surface (not shown) and a rearward face surface 506RF. The first part has centrally formed therethrough an opening having the shape of the cross-section of the plunger shaft 501 used in conjunction with the syringe 500. It is noted that the plunger shaft 501 can have any cross-sectional shape; such as ribbed, cylindrical, triangular, square, etc. Accordingly, the cross-section of the opening in the contaminant shield 510 corresponds to the plunger shaft cross-sectional shape. If the contaminant shield 510 is formed separately, or with a different material than that used to form the syringe barrel cavity 502C, then a dovetail groove 504DT, or any other similar locking groove, can be formed in the inner wall surface 502IW of the syringe barrel 502 along the circumference or perimeter of the barrel syringe inner wall surface 502IW at or near the rearward end opening 502RO of the syringe barrel 502. During the molding process, the dovetail groove 504DT receives and anchors the material used to form the first part 506 of the contaminant shield 510.

The second part 507 of the contaminant shield 510 is formed from a soft, flexible material that has a bendable characteristic. The second part 507 is formed within the cross-sectional opening and on the periphery of the first part 506. The second part 507 projects from the periphery 506P or edges of the first part and into the cross-sectional opening. The second part terminates as a flexible lip, edge, or periphery 507P that defines the cross-sectional opening. During operation or use, the lip, edge, or periphery 507P of the second part 507 is in contact with the surfaces of the ribs 501R of the plunger shaft 501, which fits within the cross-sectional opening and traverses the opening as the plunger shaft 501 exits and enters the syringe barrel cavity 502C. The second part 507 is formed on the cross-sectional periphery of the first part 506P as by providing a dovetailed shape, or other surface shape which provides a locking function, to the cross-sectional periphery 506P of the first part 506 during its forming operation to which the second part 507 can be subsequently formed about. This can be accomplished by providing the external surface of the first part at its edge or periphery 506P with a dovetailed shape, or other surface shape such as slits or holes, which would provide a locking mechanism or function to the cross-sectional periphery of the first part 506 during its forming operation to which the second part 507 can be formed about. Alternatively, a dovetailed groove, or similar locking groove, can be provided at and within the cross-sectional periphery 506P or edge of the first part 506 to receive and anchor the material used to form the second part 507 of the contaminant shield 510. Thus, the material used to form the second part 507 can be molded directly to the periphery of the first part 506, or the first part 506 and second part 507 can be molded separately and then interlocked, attached, or bonded together. The rearward end terminus 501RT of the plunger shaft 501 is centrally molded to the forward face surface 504FF of a plunger handle member 504 with the body of the plunger shaft 501 extending through the cross-sectional opening formed in the contaminant shield 510. The forward end terminus 501FT of the plunger shaft 501 has a piston 501P attached or formed thereto by one or more of the methods of mounting; twisting, turning, rotating, or screwing onto threads located at the forward terminus of the plunger shaft; fusing; molding; adhesives; ultrasonic bonding or welding; thermal bonding; locking attachment; etc., and, along with the plunger shaft, is movably fitted into the cavity, fluid reservoir, or hollow portion 502C of the syringe barrel 502. The syringe barrel 502 is formed with two open ends 502RO and 502FO located at opposite ends of the syringe cavity 502C. The rearward end of the syringe barrel 502 has a plunger shaft cross-sectional opening as described above and the forward end terminus of the syringe barrel 502 has a small diameter opening 502FO. The small diameter opening 502FO has a reduced diameter neck 502RDN having tapered internal walls forming the entrance/exit port for the syringe cavity 502C. The needle hub 505H of a needle 505 is attached to the reduced diameter neck 502RDN of the syringe 500. In operation, the plunger shaft 501 can be manually withdrawn from the syringe barrel cavity 502C by grasping the outer syringe barrel surface 502OW with one hand and the plunger shaft handle member 504 with the other hand and pulling the plunger shaft handle member 504 such that the plunger shaft 501 emerges from the hollow or cavity 502C of the syringe barrel 502 through the rearward end plunger shaft cross-sectional opening formed in the contaminant shield 510 or 520 exposing the plunger shaft 501 to the external environment. It is noted that the above manual operation can be performed with one hand, or with machinery. During withdrawal, the piston 501P at the forward end terminus 501FT of the plunger shaft 501 slidably engages and maintains a tight seal with the internal wall surfaces 502IW of the syringe barrel cavity 502C while moving along the syringe barrel cavity 502C and away from the tapered internal walls 502TIW of the syringe barrel 502. This causes the air column in the syringe bore or cavity 502C behind the piston 501P and adjacent the plunger shaft 501 to be expelled or pushed out of the syringe cavity 502C through the plunger shaft cross-sectional opening creating a vacuum in the space located between the forward end of the piston head 501HP and the internal tapered wall surfaces 502TIW of the syringe barrel 502. The plunger shaft 501 remains in a withdrawn position until a force is applied along the longitudinal axis of the plunger shaft 501 in a direction toward the forward end terminus 501FT of the plunger shaft 501 and tapered internal wall surfaces 502TIW to cause the plunger shaft 501 to pass through the plunger shaft cross-sectional opening formed in the contaminant shield 510 or 520 and cause the plunger shaft 501 and piston 501P to advance along the longitudinal axis of the syringe barrel cavity 502C toward the tapered internal wall surfaces 502TIW and entrance/exit port forward end opening 502FO of the reduced diameter neck 502RDN of the syringe barrel 502. The inside diameter of the syringe barrel 502 is equal to or slightly less than the diameter of the rim portion 501PR of the piston 501P such that the piston rim 501PR slidably engages and maintains a tight seal with the internal wall surfaces 502IW of the syringe barrel cavity 502C as the piston 501P is advanced and withdrawn to maintain liquid medication or other fluid or material in the cavity 502C forward of the piston head 501HP during advancement and withdrawal of the plunger 501 and piston 501P such that the medication or other liquid or material in the syringe barrel cavity 502C is ejected from the syringe cavity 502C through the entrance/exit port/ forward end opening 502FO. As the plunger shaft 501 and piston 501P advance along the internal wall surfaces 502IW of the syringe barrel cavity 502C toward the forward opening 502FO, the semi-rigid flexible material 508 or the flexible second part 507, depending on which contaminant shield 510 or 520 design is used, contacts the rib surfaces 501R of the plunger shaft 501 while it is advanced through the plunger shaft cross-section of the contaminant shield 510 or 520 providing a wiping and sweeping action to the rib surfaces 501R of the plunger shaft 501 in a direction away from the forward end terminus 501FT of the plunger shaft 501 as the plunger shaft 501 and piston 501P are caused to traverse the syringe cavity 502C toward the forward end terminus of the syringe barrel 502 thereby aiding in preventing entry of contaminants into the syringe barrel cavity 502C. The sweeping and wiping action functions to push contaminants such as dirt, dust, fibers, hair, glass fragments, foreign particles, microorganisms, pyrogens, and pathogens, and any other types of contaminant carried by the air, hands, fingers, gloves, hair, clothing, etc, that are deposited onto the exposed portion of the plunger shaft 501, in a direction away from the forward end of the plunger shaft 501FT and ultimately restricting the contaminants from entering the syringe barrel cavity 502C by way of the plunger shaft 501. The contaminant shield 510 or 520 also functions to prevent deposition of dirt, lint, viral components, bacteria, germs, dust, microorganisms, pathogens, pyrogens, glass fragments, paper fibers, cloth fibers, hair, foreign particles, and any other type of contaminant, etc., carried by the air, hands, fingers, gloves, hair, clothing, etc., from falling into the rearward end opening 502RO of the syringe barrel 502 and becoming deposited onto the internal wall surfaces 502IW of the syringe barrel cavity 502C. The contaminant shield 510 or 520 of the instant invention provides protection to the plunger shaft 501 and the internal cavity wall surfaces 502IW of the syringe barrel 502 in that contaminants deposited onto the outer surfaces 508RF and 506RF or the environmentally exposed surfaces of the second part 507 of the contaminant shield 510 or 520 will not jeopardize the sterility of the inner cavity 502C of the syringe barrel 502 holding the medication, solution, or other fluids, etc., because the contaminants cannot penetrate rearward face surfaces 506RF or 508RF of the contaminant shields 510 and 520, respectively. It is noted that the handle member 503 of syringe barrel 530 can also be provided with an extension forming a tab, knob, or handle 503T that functions as a wall for leverage to assist the user in drawing the plunger shaft 501 from the syringe cavity 502C. In operation, medication or other material is drawn up from a vial or ampoule, ampul, ampule, for example, by first introducing the needle 505, which is attached to the reduced diameter neck 502RDN of the entrance/exit port/forward end opening 502FO, into the vial or ampoule, ampul, ampule, containing the medication or other material. Next, the plunger handle member 504 and/or plunger shaft 501 in a direction away from the contaminant shield 510 or 520. This also causes the plunger shaft 501 and piston 501P to travel-se the syringe barrel cavity 502C away from the tapered internal walls 502TIW of the syringe barrel cavity 502C and toward the rearward end opening 502RO and contaminant shield 510 or 520. As the plunger piston 501P traverses the syringe barrel cavity 502C, the piston rim 501PR slidably engages and maintains a tight seal with the internal wall surfaces 502IW of the syringe barrel cavity 502C. A vacuum is created in the space located between the forward end of the piston head 501HP and the tapered internal wall surface 502TIW of the syringe barrel 502 as the piston head 501HP is pulled away from the tapered internal walls 502TIW. The vacuum created causes the liquid medication or other material in the vial, or ampul, ampoule, ampule to be drawn into the syringe barrel cavity 502C through the needle 505, which is frictionally attached by a hub 505H to the outer walls of the reduced diameter neck 502RDN, and the entrance/exit port forward end opening 502FO. The needle 505 is then removed from the vial, or ampul, ampoule, ampule of medication or other material and positioned in the needle port of an appropriate bag or bottle of intravenous solution. The liquid medication is then injected into the bag or bottle of intravenous solution. The reduced diameter neck 502RDN can be manufactured or molded to operate with any existing line of hypodermic needles, tubing, caps, closures, etc.

As an alternative to forming or molding the contaminant shield 510 and 520 onto the inner wall surface 502IW of the syringe barrel 502, the contaminant shield 620, as shown in FIG. 12, can be formed separately from the syringe barrel 600 and attached in a separate operation. Syringe barrel 600 has an outer wall surface 602OW and an inner wall surface 602IW. For example, the contaminant shield 620 could be formed with at least one male extending wall 607 extending perpendicularly from the forward face surface 606FF of the contaminant shield 620 with the outer surface of the at least one male wall 607 having threads and/or grooves 608T formed thereon which mate with threads and/or grooves 605TG, formed on or in the inner wall surfaces 602IW at or near the rearward end opening 602RO of the syringe barrel 600, by screwing, turning, twisting, or rotating the threaded and/or grooved end cap contaminant shield 620 with the threads and/or grooves 605TG on the syringe barrel 600 inner wall surface 602IW. The contaminant shield also has a rearward end face 606RF that faces the forward face surface 612 of plunger handle member 630. As an alternative, the threads and/or grooves can be formed in the outer surfaces of the extending male walls 607 of the end cap contaminant shield 620 and the threads and/or grooves 608T formed on the inner wall surfaces 602IW at the rearward end opening 602RO of the syringe barrel 600. That is, the threads and/or grooves are cut or formed in the outer surface of the at least one extending male wall 607. In a further alternative, the threads and/or grooves 608T can be formed on or in the inside wall surfaces of the at least one extending male walls 607 of the end cap contaminant shield 620 and threads and/or grooves 605TG can be formed on or in the outer wall 602OW surface of the syringe barrel 600 at or near the rearward terminus 602RT. The at least one extending male wall 607 has an appropriate inside wall diameter that forms a receiving cavity that allows the threads and/or grooves 608T formed on or in the inside wall surfaces of the at least one male wall 607 to receive and mate with the threads and/or grooves 605TG formed on or in the outer wall surface 602OW of the syringe barrel 600 at the rearward end terminus 602RT. Alternatively, the at least one extending male wall 607 has an inside wall diameter equal to or slightly greater than the outside wall 602OW diameter at the rearward end terminus 602RT of the syringe barrel 600, such that the inside wall surfaces of the at least one extending male wall 607 form a receiving cavity for receiving the rearward end terminus 602RT and mate with and form a frictional fit with the outside wall surfaces 602OW of the syringe barrel rearward end terminus 602RT. Alternatives to frictional fitting include: fusing; molding; ultrasonic bonding or welding; thermal bonding or welding; locking attachment, etc., and combinations thereof can be used. FIG. 12 shows the plunger shaft 604PS positioned within the syringe barrel cavity 602C. The piston 604P is attached by one or more of the methods of mounting; twisting, turning, rotating, or screwing onto threads located at the forward terminus of the plunger shaft; fusing; molding; adhesives; ultrasonic bonding or welding; thermal bonding; locking attachment; etc., on the forward end terminus of the plunger shaft 604FT. The piston 604P has a rim 604R and a piston head 604HP. The plunger shaft 604PS has plunger shaft ribs 604PSR. It is noted that ribs are not required in the design feature for the plunger shaft and that any design shape or cross-section can be used for the plunger shaft. Such shapes include, but are not limited to, rectangular, triangular, cylindrical, hexagonal, etc. The rearward terminus 604RT of the plunger shaft 604PS extends out of the rearward opening 602RO of the syringe barrel cavity 602C. One method of manufacture includes separately molding the end cap contaminant shield 620, syringe barrel 600, plunger handle member 630, and plunger shaft 604PS and piston 604P by any desired method or methods. The next steps involve assembling the syringe components. The rearward terminus 604RT of the plunger shaft 604PS is threaded through the cavity or hollow formed by the walls 607 extending from the forward face surface 606FF of the end cap contaminant shield 620 and then through the cross-sectional opening 610CSO. Upon threading of the plunger shaft 604PS through the cross-sectional opening 610CSO, the periphery of the flexible second part 609 contacts the rib surfaces 604PSR of the plunger shaft 604PS. The next step involves attachment of the plunger handle member 630 to the rear terminus 604RT of the plunger shaft 604PS. Alternatively, the plunger handle member 630 can be formed and molded directly to the rearward terminus 604RT of the plunger shaft 604PS following the threading operation such that the forward face 612 of the plunger handle member 630 is facing the rearward face surface 606RF of the end cap contaminant shield 620. The rearward face surface 611 of the plunger handle member 630 faces away from the rearward face surface 606RF of the end cap contaminant shield 620 after molding or attachment of the plunger handle member 630 to the rearward end terminus 604RT of the plunger shaft 604PS. Next, the piston 604P is attached to the plunger shaft 604PS. Alternatively, the piston 604P can be formed or molded to the plunger shaft 604PS forward end terminus 604FT prior to the threading operation or after the threading operation. Also, the piston attachment operation can occur prior to attachment or molding of the plunger handle member 630 to the rearward terminus 604RT of the plunger shaft 604PS. Next, the plunger shaft 604PS and attached piston 604P are inserted into the syringe cavity 602C. The end cap contaminant shield 620 can then be slid along the plunger shaft 604PS such that the threads and/or grooves 608T mate with the threads and/or grooves 605TG of the syringe barrel 600 inner wall 602IW. The piston 604P, plunger shaft 604PS, end cap contaminant shield 620, and plunger handle member 630, are rotated, screwed, twisted, or turned in a clockwise direction to mate the threads and/or grooves 608T with the threads and/or grooves 605TG and cause the end cap contaminant shield 620 to be inserted into the rearward end opening 602RO of the syringe barrel 600. However, rotation of all components may not be necessary depending on the cross-section of the plunger shaft, i.e., cylindrical. These assembly steps can also be used with the previously described end cap contaminant shield alternative designs. A sealant or gasket material can be provided on the forward face surface 606FF of the end cap contaminant shield 620 which mates with the rear terminus 602RT surface to enhance the seal between the rear terminus wall 602RT of the syringe barrel 600 and the forward face surface 606FF of the end cap contaminant shield 620. A further alternative for attachment of the plunger shaft handle member 630 includes attaching by one or more of the methods of mounting; fusing; molding; adhesives; ultrasonic bonding or welding; thermal bonding; etc., the plunger shaft handle member 630 to the plunger shaft rear terminus 604RT following insertion, thread mating, and attachment of the end cap contaminant shield 620 to the syringe barrel 600. It is noted that the end cap contaminant shield 620 can also be provided with an extension forming a tab, knob, or handle 606 that functions as a wall for leverage to assist the user in drawing the plunger shaft 604PS from the syringe cavity 602C.

Further modifications, as shown in FIGS. 13A and 13B, include providing contaminant shields 640 and 650. End cap contaminant shield 640 is shown having at least one wall 607 extending perpendicularly from the forward face surface 606FF such that the outer surface of the at least one extended walls 607 mates with the inner wall surfaces 602IW of the syringe barrel 600 at the rearward end opening 602RO through frictional fitting, snap fitting, locking, etc., and any combination thereof. End cap contaminant shield 640 has a lip or flange 613 extending perpendicularly from the at least one wall 607 to facilitate fitting of the end cap contaminant shield 640 into the rearward end opening 602RO. The flange 613 mates and locks with a complementary groove or lip extension formed on the inner wall surface 602IW of the syringe barrel cavity 602C. The flange 613 can be formed of any desirable material and can be flexible or stiff or hard. The flange 613 can be bendable and flexible such that it allows a tight fit between the walls 607 and inner wall surfaces 602IW. The flange 613 also functions as a seal and barrier to contaminants. The flange 613 may encircle the entire circumference of the wall 607 and the lip extension may encircle the entire circumference of the inner wall surface 602IW. Alternatively, the flange 613 may encircle the entire outer circumference of the at least one male wall 607, or one or more flanges 613 can be formed that encircle less than the entire outer circumference of the at least one male wall 607. If more than one flange 613 is used, they can be staggered at different longitudinal lengths along the wall 607 in an alternating fashion to facilitate a locking capability with one or more lip extensions formed on the inner wall surface 602IW of the syringe barrel cavity 602C. Such a design allows the at least one flange 613 to form a keyed fit with the lip extensions formed on inner walls 602IW of the syringe barrel cavity 602C following insertion of the at least one male extending walls 607 and at least one flange 613 into the rearward end opening 602RO of the syringe barrel 600. The contaminant shield 640 is turned, twisted, etc. to lock the flange walls 613 behind or between the lip extensions formed on the inner walls 602IW of the syringe barrel cavity 602C. The contaminant shield member 650 of FIG. 13B is a contaminant shield structure having all of the components of end cap contaminant shield structure 620 except for the extending walls 607 and threads and/or grooves 608T. The contaminant shield member 650 has a forward face surface 606FF and a rearward face surface 606RF. After molding of the contaminant shield 650, the forward face surface 606FF is bound or attached to the rearward end terminus 602RT of syringe barrel 600 by one or more of the methods of mounting; fusing, molding; adhesives; ultrasonic bonding or welding; thermal bonding; etc. The contaminant shield member 650 is formed of a first part material 606, which can be the same or different from the material used to form the syringe 600, and a second part material 609 having a flexible characteristic. The first part 606 is formed or molded to have a cross-sectional opening therethrough having the shape of the plunger shaft cross-section. The second part material 609 is molded or formed to the periphery of the first part 606 cross-sectional opening to form a cross-sectional opening 610CSO also having the cross-sectional shape of the plunger shaft 604PS. The second part 609 of the contaminant shield is formed on the cross-sectional edge or periphery of the first part 606. A dovetailed shape, grooves, holes, slits, projections, other shapes, and combination thereof, is formed in or on the periphery of the first part 606 during the forming or molding process. These dovetail shapes, grooves, holes, slits, projections, or other shapes, provide a locking function to the cross-sectional periphery of the first part 606 for anchoring the material used to form the second part 609 of the contaminant shield 650. Thus, the material used to form the second part 609 can be molded directly to the periphery of the first part 606 or the first part 606 and second part 609 can be molded separately and then interlocked, attached, or bonded together. The contaminant shield member 650 is threaded over the plunger shaft 604PS prior to attachment, by one or more of the methods of molding; bonding as by adhesives; ultrasonic bonding or welding; thermal bonding; etc., of the forward face surface 606FF of contaminant shield member 650 to the rearward end terminus 602RT of syringe barrel 600. The plunger handle member 630 can be molded, formed, or attached to the rearward end terminus 604RT of the plunger shaft 604PS prior to or following attachment or bonding of contaminant shield member 650 to the rearward end terminus 602RT of the syringe barrel 600. The plunger shaft 604PS and attached piston 604P can be inserted into the syringe barrel 600 prior to or subsequent to any attachment, threading, or forming step.

An advantage of using the contaminant shield designs of the fifth embodiment is the protection provided by the shield to the internal cavity wall surfaces of the syringe in that contaminants deposited onto the rearward end wall surfaces of the shield will not jeopardize the sterility of the inner cavity of the syringe barrel because the contaminants cannot penetrate the shield.

An added function and benefit of the fifth embodiment is that the shield functions to prevent accidental separation of the plunger member from the syringe barrel by abutment of the forward face surface of the shield or the extended wall of the end cap with the forward end terminus of the plunger shaft. Second, the shield functions as a temporary dam or barrier to medications, fluids, and other types of materials that may escape the syringe cavity due to piston failure.

CONCLUSION

Accordingly, the reader will see that the syringes of the instant invention can be used for accomplishing many tasks requiring the use of a syringe. Because of the design of the syringes of the instant invention, entry of contaminants such as dirt, dust, fibers, microorganisms, pathogens, pyrogens, hair, glass fragments, foreign particles, and any other type of contaminants, carried by air, hands, fingers, hair, clothing, etc., which may become deposited onto the internal surfaces of the syringe barrel cavity, is discouraged and prevented. Additionally, using the syringes of the instant invention provides protection to the plunger shaft and the internal cavity wall surfaces in that contaminants deposited onto the external wall surfaces of the syringe barrel will not jeopardize the sterility of the inner cavity of the syringe barrel holding the medication, solutions, etc., or other fluid or materials because the contaminants cannot penetrate the walls of the syringe barrel, the seals, the corrugated sheath, non-corrugated sheath, plunger shafts, plunger members, handle members, or the shield walls, etc.

The syringes of the instant invention can be disposable or be reusable following an acceptable sterilization process.

The syringe barrels, plungers, plunger shafts, pistons, syringe caps, corrugated sheaths, non-corrugated sheaths, shields, sealing rings, syringe and plunger shaft handle members, etc., of the instant invention can also have any desired geometrical and/or cross-sectional shape such as cylindrical, triangular, square, hexagonal, octagonal, etc.

The syringes and/or separate syringe components of the invention are manufactured and provided with sterile inner and outer surfaces and packaged in sterile packaging. All components are manufactured in clean room environments.

Sterilization of components can be accomplished by irradiation, gamma irradiation, ethylene oxide (ETO) sterilization, formaldehyde, steam, dry-heat, thermal, gas, ionizing radiation, autoclaving, filtration, etc.

The syringes, components, and materials of the instant invention are selected to meet the requirements and regulations for use, disposal, and incineration of medical devices when used in that capacity.

The syringes of the instant invention can be of any desired shape, size, length, diameter, etc.

The syringes, sheaths, and other components of the instant invention may also be manufactured having any desired color or tint, as long as the barrel retains some degree of transparency or other means to afford the user the ability to inspect the contents and read the volume of the liquid or other material in the syringe barrel cavity using the volume measuring indicia printed on the syringe barrel walls. The printed indicia on the syringe barrel walls provides incremental markings used to accurately measure the volume of the medication, solution, or other material drawn into the syringe barrel cavity. If the coloring or tinting used for the syringe barrels is intended to provide a completely darkened or opaque result, such that light penetration through the syringe barrel is obstructed in order to protect the contents of the syringe barrel from light and/or other decomposing entities, a clear or colorless window or inspection site having any desired design or shape can be provided on or in the syringe barrel for measuring and viewing the solution, suspension, fluid, etc., or other material being drawn into and ejected out of the syringe barrel cavity. The inspection site window can run the longitudinal length of the syringe barrel. If the material being drawn into the syringe is particularly prone to degradation due to light exposure, the inspection site or window may also be tinted or colored to have a lighter color or tint than the syringe barrel. The volume measuring indicia can be printed over or adjacent to the inspection window. The inspection window can also be provided with a sliding or hinged door, which can be slid or pivoted open to expose the inspection window. The door functions to cover the inspection window and aids in protecting the contents of the syringe from light exposure by way of the inspection window. This is particularly important for materials, such as medications, that are sensitive to light exposure and are being exposed to light for an extended period of time—such as when the syringe carrying the material is being used in a syringe pump for delivering medication. As an alternative, adhesive foil or tape material that functions to block light and other degrading or decaying components or constituents can be used to cover the inspection window after the appropriate amount of material has been drawn into the syringe. The adhesive foil or tape material functions to cover the inspection window and aids in protecting the contents of the syringe from light exposure by way of the inspection window. Such adhesive foils or tapes can be permanent or removable, once applied. Alternatively, volume measuring indicia can be printed on the plunger shaft such that as the plunger shaft is withdrawn from the syringe barrel, the indicia on the plunger shaft allows the user of the syringe to measure the volume of the material being drawn into or ejected from the syringe barrel cavity. Indicia can be printed on the plunger shaft in both directions that allows the user to measure the volume that has been ejected from the syringe. The inspection window designs of the instant invention can be used with the corrugated sheaths, non-corrugated sheaths, and shield syringe designs of the instant invention.

The design and features of the syringes of the instant invention can be used with any volume syringe, i.e. 0.5 mL, 1 mL, 3 mL, 5 mL, 10 mL, 20 mL, 30 mL, 35 mL, 50 mL, 60 mL, etc., and any type needle, i.e., subcutaneous, tuberculin, filter, vented, intravenous, etc., and any size gauge needle, i.e., 18 G, 19 G, 20 G, 22 G, 21 G, 25 G, 28 G, 30 G, 32 G, etc. and transfer sets, tubing, etc. The needle can have any length, i.e., ½, inch ⅝ inch, ⅜ inch, 1 inch, 1½ inch, etc.

The materials used for constructing the syringes barrels, plunger members, plunger shafts, pistons, sealing rings, corrugated sheaths, non-corrugated sheaths, gaskets, needles, needle caps, handle members, contaminant shields, brace means, locking components, bars, tamper-evident components, inspection windows, inspection window doors, coloring materials, printing materials, packaging materials, and other components of the instant invention include, but are not limited to, plastic materials, polymers, rubber materials, metals, alloys, glass materials, and combinations thereof, and any other additives necessary or desired, etc., such that the desired mechanical characteristics as disclosed herein are achieved. Glass syringe barrels may be coated with plastic, polymers, and rubber materials, to increase durability and decrease breakage. Also, the materials used to form the syringe components will not interact physically or chemically with the preparation, liquid, medication, etc., being drawn, injected, stored, or placed into or ejected from the syringe. Some polymer materials for manufacturing the components of the instant syringes include, but are not limited to, plastics, ethylene vinyl acetates, acrylonitrile-butadiene-styrenes, high impact polystyrenes, acrylics, polyethylenes, polystyrenes, nylons, polypropylenes, phenolics, polymethyl methacrylate, polybutadienes, polyvinyl chlorides, polyvinyl alcohols, polycarbonates, isoprenes, polyvinyl acetates, plasticizers, silicones, etc., and combinations thereof; short or long fibers of glass, Kevlar®, polyamides, graphite, polyacrylonitrile, silicone, etc., and combinations thereof, can be used for reinforcement of the materials used in forming the syringe components.

The design and features of the syringes of the instant invention can be used with any type of syringe such as tuberculin, insulin, hypodermic, oral, rectal, urethral, ear, nasal, vaginal, etc.

The diameter, radius, length, taper, etc., of the reduced diameter neck portions of the instant syringe designs is manufactured or molded to operate with or fit any existing needles, caps, closures, etc., or can be any diameter, radius, length, taper, curvature, etc.

The syringes of the instant invention can be used for withdrawing blood from patients, injecting intravenous medications into patients, operating in pump devices for delivering or administering medications to patients, as devices for delivering or administering medications and functioning as douches or enemas, preparing and administering radioactive pharmaceuticals or radiopharmaceuticals, preparing pre-filled syringes with medications for injection or oral delivery, preparing and administering intramuscular medications for injection, preparing irrigation solutions, preparing hyperalimentations, Total Parenteral Nutrition admixtures, Total Nutrition Admixtures, All-in-One or 3-in-1 Parenteral Nutrition Preparations, Peripheral Parenteral Nutrition, preparing and administering dialysis fluids, preparing intravenous pushes, preparing IV piggy-backs, preparing and administering bolus fluids, preparing and administering intravenous fluids, preparing large volume parenterals for intravenous injection, and preparing and administering oral dose medications, etc. Also, the syringes of the instant invention can be pre-filled or pre-dosed with medications or other materials and function as pre-filled syringes or pre-dosed syringes, single-use syringes, etc., and multi-dose syringes containing injectable or oral medications such as vaccines, antitoxins, antibiotics, biologicals, toxoids, vaccines, immune serums, etc., and their combinations, can be manufactured and administered using the syringes of the instant invention. Also, the syringes of the instant invention can be: pre-dosed with medications or other materials; used for drawing up and ejecting, manufacturing, making, preparing, delivering, administering medications or other materials for use in procedures such as, intracutaneous or intradermal, intracameral, subconjunctival, retrobulbar, subcutaneous, intramuscular, intravenous, epicutaneous, intraspinal, intracardiac, intraarterial, intraarticular, intradermal, intraosseous, intrasynovial, intrathecal, intrauterine, intravaginal, intracisternal, peridural, epidurals, conjunctival, transdermal, intrarespiratory, intraocular, intranasal, ophthalmics, otics, inhalants, enemas, rectals, vaginals, douches, urethrals, in vivo and in vitro procedures, pharmaceuticals, drugs, excipients, etc., and combinations thereof. The syringes can also be pre-dosed with, used for drawing up, ejecting, or used in the compounding or manufacture of, lotions, ointments, ointment and suppository bases, cocoa butter, PEG bases, creams, emulsions, gargles, buccals, transdermals, foams, mixtures, wafers, aromatic waters, vitamin waters, herbal waters, herbals, medication waters, acids, caustics, cytotoxic agents, chemotherapy agents, glycerin, glycols, ketones, ethers, chloroform, bases, salts, pH adjusting agents, preservatives, waters for injection, waxes, paraffins, bleaching agents, topical jellies, surfactants, wetting agents, detergents, chelating agents, thickening agents, polymers, polysaccharides, antipyretics, polypeptides, humectants, propellants, emulsifiers, emulsifying agents, plasticizers, liposomes, water, acidifying agents, tonicity adjusters, alkalinizing agents, adsorbents, absorbents, antifungals, antimicrobials, antibodies, RNA, DNA, proteins, peptides, oligonucleotides, viruses, retroviral vectors, adenoviral vectors, electrolytes, anesthetics, waters for inhalation, bacteriostatic waters, nutrients, viscosity inducing agents, amino acids, nucleic acids, supplements, phytochemicals, dispersions, steroids, hormones, alkaloids, minerals, medicinal herbs, homeopathics, polymers, lipids, fat emulsions, fats, biotechnology products, blood, blood products, plasma, blood precursors, genes and their products and precursors, antioxidants, dispersing agents, antieczema, soaps, detergents, buffers, colorants, clarifying agents, encapsulating agents, flavorants, levigating agents, stiffening agents, surfactants, suspending agents, suspending mediums, sweeteners, scents, binders, antiadherents, diluents, astringents, coatings, disintegrants, glidants, lubricants, irrigating solutions, gums, plasters, glycerogelatins, protectives, occlusives, elixirs, solvents, syrups, tinctures, antiseptics, analgesics, disinfectants, drying agents, antibacterials, keratolytics, sprays, antisebbhoraics, antipsoriatics, demulcents, aerosols, liniments, oils, spirits, fluidextracts, extracts, pastes, suspensions, vitamins, trace elements, solutions, aqueous solutions, cleansers, emollients, pluronic lecithin organogel (plo's), foams, troches, lozenges, suppositories, gels, magmas, colloids and colloidals, coatings, alcohols, capsules, tablets, pills, powders, liquids, pellets, solvents, granules, beads, microspheres, transdermal delivery systems, implants, inserts, parenterals, biologicals, radiopharmaceuticals, radiochemicals, etc., and combinations thereof. Also, pre-filled or pre-dosed syringes for use in delivering chemicals, plasters, caulks, paints, dyes, pigments, stains, glue materials, chemicals that interact to cure or harden when mixed, and combinations thereof, etc. The syringes of the instant invention can also be used in automated syringe filling processes and in medication pump devices, etc., and combinations thereof. The syringes of the instant invention can also be used for holding and dispensing food products such as juices, cheeses, sauces, marinades, glazes, jellies, ketchup or catsup, mustard, mayonnaise, barbecue sauce, dips, toppings, icings, gravies, syrups, butters, honey, peanut butter, sandwich and cracker spreads, whipped creams, oils, seasonings, etc., and combinations thereof. While the description of uses above provides many examples for use of the syringes of the instant invention, these examples should not be construed as limiting the scope of the functionality or capacity of use of the syringe designs of this invention. That is, in addition to the uses indicated above, the syringes of the instant invention can be used in any capacity that requires the use of a syringe.

The design of the sealing rings can be of any desired shape such as, circular, triangular, square, etc. The periphery forming the sealing ring can have any desired shape such as blocked, apexed, rounded, etc. The sealing rings can also be designed as flexible flaps extending from the surface of the syringe barrel and plunger member wall surfaces. Any shaped locking groove, such as dovetail, etc., can be formed on the syringe barrel and plunger member walls and fitted with preformed sealing rings. Additionally, the preformed sealing rings can be formed by fusion, injection molding, extrusion molding, compression molding, or any other type of molding process, etc., or combination of processes. Alternatively, forming of the sealing rings and their attachment process or method to the syringe barrel walls and plunger member walls can be performed by injection molding, blow molding, extrusion molding, compression molding, etc., or any type of molding process or combination of processes, the plunger member and syringe-barrel against preformed sealing rings; or injection molding sealing rings to a preformed plunger member and/or syringe barrel; or compression molding sealing rings to a preformed plunger member and/or syringe barrel; or, simultaneously fusing, by performing injection molding, blow molding or blow extrusion of the syringe barrel or plunger member against injection or compression molded sealing rings, or combinations thereof.

As an alternative, or in addition to the sealing rings, prongs or projections having any desired shape can be molded or formed on the syringe barrel internal wall at a desired location such that they protrude into the rib cavities or syringe barrel cavities and abut with the forward end terminus of the plunger shaft during its withdrawal along the syringe barrel cavity such that the prongs or projections prevent complete withdrawal or separation of the plunger shaft from the syringe barrel cavity. As an alternative, bars can be molded or formed across the diameter of the rearward end opening of the syringe barrel that function to abut with the forward terminus of the plunger shaft as the plunger shaft exits the rearward end opening of the syringe barrel cavity and prevent separation of the plunger shaft and piston from the syringe barrel cavity.

The corrugated and non-corrugated sheaths of the instant invention can be manufactured to have any desired length, radius, diameter, shape, color or tint. The corrugated sheaths may have any desired number of corrugations. The corrugated sheaths of the instant invention may also be designed to have alternating straight segments and corrugated segments along the length of the sheath.

I claim:

1. A syringe comprising:
   a) a syringe barrel;
   b) said syringe barrel having inner walls defining a syringe barrel cavity; wherein said syringe barrel cavity is provided with a forward end port such that materials enter and exit said syringe barrel cavity only through said forward end port;
   c) a plunger member comprising a plunger shaft and piston, said plunger member positioned within said syringe barrel cavity, said piston of said plunger member contacting said inner walls of said syringe barrel cavity; and
   d) a sheath positioned within said inner walls of said syringe barrel cavity between the rear terminus of said syringe barrel and the forward terminus of said plunger shaft, said sheath enclosing a portion of said plunger shaft.

2. The syringe of claim 1, wherein inner walls of said sheath are in an unobstructed face-to-face relationship with said inner walls of said syringe barrel cavity between the forward terminus and the rear terminus of said sheath.

3. The syringe of claim 1, wherein outer walls of said sheath are in an unobstructed face-to-face relationship with the plunger shaft between the forward terminus and the rear terminus of said sheath.

4. The syringe of claim 1, wherein said plunger shaft having a rearward terminus centrally molded and normal to the forward face surface of a plunger handle member, said plunger handle member further having an unobstructed rear face surface.

5. The syringe of claim 1, wherein said sheath is adapted to shorten when withdrawing said plunger shaft from said syringe barrel cavity and elongate when advancing said plunger shaft into said syringe barrel cavity.

6. The syringe of claim 1, wherein said syringe is provided with coloring, tinting, or opaqueness.

7. The syringe of claim 6, wherein said syringe barrel is provided with an inspection window.

8. The syringe of claim 7, wherein said inspection window is provided with a hinged or sliding door for exposing (revealing) and concealing said inspection window.

9. The syringe of claim 1, wherein said syringe barrel or said plunger shaft is provided with measuring indicia.

10. A syringe comprising:
    a) a syringe barrel having a rear terminus; wherein said rear terminus of said syringe barrel comprises a syringe barrel handle member integrally molded therewith;
    b) a syringe barrel cavity;
    c) a plunger member comprising a plunger shaft and piston; and
    d) a corrugated sheath having inner walls and outer walls positioned within said syringe barrel cavity; said corrugated sheath having a forward terminus and a rear terminus; wherein said rear terminus of said corrugated sheath is molded to said syringe barrel handle member.

11. The syringe of claim 10, wherein said outer walls of said corrugated sheath are in an unobstructed face-to-face relationship with said plunger shaft from said syringe barrel rear terminus to said corrugated sheath forward terminus.

12. The syringe of claim 10, wherein said inner walls of said corrugated sheath are in an unobstructed face-to-face relationship with the inner walls of said syringe barrel cavity between the forward terminus and the rear terminus of said corrugated sheath.

13. The syringe of claim 10, wherein said corrugated sheath is adapted to shorten when withdrawing the plunger shaft from the syringe barrel cavity and elongate when advancing the plunger shaft into the syringe barrel cavity.

14. The syringe of claim 10, wherein said corrugated sheath is molded to said plunger shaft.

15. The syringe of claim 10, wherein said corrugated sheath encloses a portion of said plunger shaft.

16. A syringe comprising:
    a) a syringe barrel;
    b) a syringe barrel cavity having inner walls;
    c) a plunger member comprising a plunger shaft and piston; said piston comprising a piston head; wherein materials that enter or exit said syringe barrel cavity physically contact only said piston head and said inner walls of said syringe barrel cavity; and
    d) a corrugated sheath having a forward terminus and a rear terminus positioned within said syringe barrel cavity and attached to said plunger shaft.

17. The syringe of claim 16, wherein said corrugated sheath is adapted to elongate when advancing said plunger shaft into said syringe barrel cavity and shorten when withdrawing said plunger shaft from said syringe barrel cavity.

18. The syringe of claim 16, wherein said syringe barrel having a forward terminus and a rear terminus, outer walls of said corrugated sheath are in an unobstructed face-to-face relationship with said plunger shaft from said syringe barrel rear terminus to said corrugated sheath forward terminus.

19. The syringe of claim 16, wherein said syringe barrel having a forward terminus and a rear terminus, said plunger shaft having a forward terminus, said corrugated sheath positioned within said inner walls of said syringe barrel cavity between the rear terminus of said syringe barrel and the forward terminus of said plunger shaft, said corrugated sheath enclosing a portion of said plunger shaft.

20. A syringe comprising:
    a) a syringe barrel defining a syringe barrel cavity and forward end port; said port adapted for entry and exit of materials;
    b) a plunger member positioned in said syringe barrel cavity, said plunger member comprising a plunger shaft and piston; said piston comprising a piston head adapted to abut said forward end port to impede introduction of material into said syringe barrel through said port while said piston head abuts said forward end port; and
    c) a sheath positioned within said syringe barrel cavity and attached to said plunger shaft, said sheath is adapted to shorten when withdrawing the plunger shaft from the syringe barrel cavity and elongate when advancing the plunger shaft into the syringe barrel cavity.

21. The syringe of claim 20, wherein said sheath is adapted to elongate and shorten within said syringe barrel cavity and along a longitudinal length of a portion of said plunger shaft.

22. The syringe of claim 20, wherein said sheath having a forward terminus and a rear terminus, inner walls of said sheath are in an unobstructed face-to-face relationship with inner walls of said syringe barrel cavity between the forward terminus and the rear terminus of said sheath.

* * * * *